US009408831B2

(12) United States Patent
Zeldis

(10) Patent No.: US 9,408,831 B2
(45) Date of Patent: Aug. 9, 2016

(54) METHODS FOR TREATING RESPIRATORY VIRAL INFECTION

(75) Inventor: Jerome B. Zeldis, Princeton, NJ (US)

(73) Assignee: Celgene Corporation, Summit, NJ (US)

(*) Notice: Subject to any disclaimer, the term of this patent is extended or adjusted under 35 U.S.C. 154(b) by 684 days.

(21) Appl. No.: 13/639,848

(22) PCT Filed: Apr. 5, 2011

(86) PCT No.: PCT/US2011/031190
§ 371 (c)(1),
(2), (4) Date: Jan. 4, 2013

(87) PCT Pub. No.: WO2011/127019
PCT Pub. Date: Oct. 13, 2011

(65) Prior Publication Data
US 2013/0136770 A1    May 30, 2013

Related U.S. Application Data

(60) Provisional application No. 61/321,802, filed on Apr. 7, 2010, provisional application No. 61/435,726, filed on Jan. 24, 2011.

(51) Int. Cl.
*A61K 31/4035*  (2006.01)
*A61K 45/06*  (2006.01)
*A61K 31/454*  (2006.01)

(52) U.S. Cl.
CPC ........... *A61K 31/4035* (2013.01); *A61K 31/454* (2013.01); *A61K 45/06* (2013.01)

(58) Field of Classification Search
CPC .. A61K 31/4035; A61K 31/454; A61K 45/06
USPC ................. 514/416, 417; 424/278.1
See application file for complete search history.

(56) References Cited

U.S. PATENT DOCUMENTS

| 6,436,971 B2 * | 8/2002 | DeMarsh | A61K 31/277 514/285 |
| 2001/0041739 A1 | 11/2001 | Demarsh et al. | |
| 2004/0167199 A1 * | 8/2004 | Muller | A61K 31/4035 514/417 |
| 2010/0272706 A1 * | 10/2010 | Mercer | A61K 31/407 424/130.1 |

FOREIGN PATENT DOCUMENTS

| WO | 2001/003681 A2 | 1/2001 |
| WO | WO 2006/065814 | 6/2006 |
| WO | WO 2010/095041 | 8/2010 |

OTHER PUBLICATIONS

Ikemura et al., "Type 4 Phosphodiesterase Inhibitors Attenuate Respiratory Syncytial Virus-Induced Airway Hyper-Responsiveness and Lung Eisinophila," J. Pharm. and Experim. Ther., Williams and Wilkins Co., 294(2):701-706 (2000).

Ohta et al., "In Vivo Anti-Influenza Virus Activity of an Immunomodulatory Acidic Polysaccharide Isolated from Cordyceps Militaris Grown on Germinated Soybeans," J. Agric. and Food Chem., 55(25):10194-10199 (2007).

* cited by examiner

*Primary Examiner* — Jennifer M Kim
(74) *Attorney, Agent, or Firm* — Jones Day

(57) ABSTRACT

Provided herein are methods for modulating immune responses to a respiratory viral infection (e.g., influenza, rhinovirus, coronavirus, or paramyxovirus) in a subject, wherein the methods comprise administering to the subject a compound (e.g., a PDE4 modulator or an immunomodulatory compound), or a pharmaceutically acceptable salt, solvate, hydrate, or stereoisomer thereof. Also provided herein are methods for treating, preventing, ameliorating, and/or delaying the onset of one or more symptoms associated with or resulting from a respiratory viral infection (e.g., influenza, rhinovirus, coronavirus, or paramyxovirus) in a subject, wherein the methods comprise administering to the subject a compound (e.g., a PDE4 modulator or an immunomodulatory compound), or a pharmaceutically acceptable salt, solvate, hydrate, or stereoisomer thereof.

24 Claims, 9 Drawing Sheets

METHODS FOR TREATING RESPIRATORY VIRAL INFECTION

Figure 1:
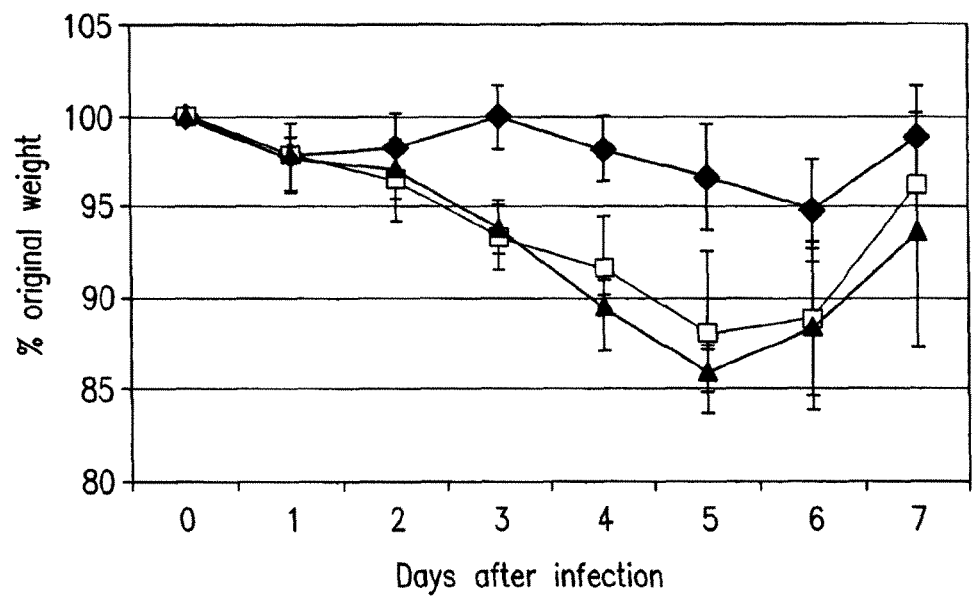

This application is the national phase entry pursuant to 35 U.S.C. §371 of International Application No. PCT/US2011/031190, which claims priority to U.S. Provisional Application Nos. 61/321,802, filed Apr. 7, 2010 and 61/435,726, filed Jan. 24, 2011, all of which are incorporated herein in their entireties.

I. FIELD

Provided herein are pharmaceutical compositions and methods for modulating immune responses to a respiratory viral infection in a subject. Also provided herein are pharmaceutical compositions and methods for treating, preventing, ameliorating, and/or delaying the onset of one or more symptoms associated with or resulting from a respiratory viral infection in a subject. In one embodiment, the respiratory viral infection includes, but is not limited to, influenza viral infection (e.g., seasonal flu), rhinovirus infection (e.g., common cold), coronavirus infection (e.g., Severe Acute Respiratory Syndrome and common cold), and/or paramyxovirus infection (e.g., measles). In one embodiment, the methods provided herein comprise administering a PDE4 modulator, or a pharmaceutically acceptable salt, solvate, hydrate, and/or stereoisomer thereof. In one embodiment, the methods provided herein comprise administering an immunomodulatory compound, or a pharmaceutically acceptable salt, solvate, hydrate, and/or stereoisomer thereof. In certain embodiments, the methods provided herein comprise administering a combination of two or more active agents, wherein at least one of the active agents is a PDE4 modulator or an immunomodulatory compound. In certain embodiments, the methods provided herein comprise administering a PDE4 modulator or an immunomodulatory compound with a secondary medication, wherein the secondary medication is an antibiotics or anti-viral compound. In certain embodiments, the methods provided herein comprise administering a PDE4 modulator or an immunomodulatory compound with an anti-viral vaccine.

II. BACKGROUND

Influenza remains a major health concern and an important disease of humans and animals. Influenza virus infection causes widespread morbidity and mortality worldwide, for example, in young children, the elderly, and the chronically ill. An estimated 5-15% of the global population is infected by influenza annually, causing severe illness in 3-5 million people and 250,000-500,000 deaths worldwide. In the United States, about 36,000 people die each year from influenza infection. Moreover, there have been about three influenza pandemics in each century for the last 300 years. The 1918 Spanish flu pandemic caused by Influenza A virus subtype H1N1 resulted in about 40 million deaths in a single year. The 1957 Asian flu caused by Influenza A virus subtype H2N2 and the 1968 Hong Kong flu caused by Influenza A virus subtype H3N2 also resulted in about 2 million and about 1 million deaths, respectively. The 2009 H1N1 influenza outbreak (the swine flu) is the most recent pandemic, causing substantial economic burdens globally (e.g., hospitalization, loss of productivity, disruption of travel). As of February 2010, more than 213 countries and overseas territories or communities have reported laboratory confirmed cases of pandemic H1N1 influenza, including at least 16,455 deaths worldwide. In addition, highly lethal and virulent influenza viral strains, such as the Influenza A virus subtype H5N1 (also known as avian influenza or bird flu), pose a serious threat of a potential pandemic in humans in the event that the viral mutation and reassortment lead to a strain that can be efficiently transmitted between humans.

Influenza viruses are segmented negative-strand ribonucleic acid (RNA) viruses. It consists of an internal core of segmented RNA associated with nucleoprotein, surrounded by a viral envelope with a lipid bilayer structure and external glycoproteins. The segmented nature of the viral genome allows the genetic reassortment (exchange of genome segments) to take place during mixed infection of a cell with different viral strains. In contrast to other infections, influenza undergoes continuous antigenic change and reassortment with animal reservoir strains. The inner layer of the viral envelope is composed predominantly of matrix proteins and the outer layer mostly of host-derived lipid material. The surface glycoproteins neuraminidase (NA) and hemagglutinin (HA) appear as spikes at the surface of the viral particles. These surface proteins, particularly the HA protein, determine the antigenic specificity of the influenza virus.

Influenza viruses are divided into three types, type A, B and C, based upon differences in internal antigenic proteins. The Influenza A virus may be further classified into various subtypes according to the different HA and NA viral proteins displayed on the surface of the virus. Each subtype of virus can mutate into a variety of strains with differing pathogenic profiles. Currently, there are 16 known HA antigen subtypes (H1 to H16) and 9 known NA antigen subtypes (N1 to N9). Influenza A viruses can infect humans, birds, pigs, horses, and other animals. A subset of Influenza A virus subtypes, including but not limited to, H1N1, H2N2, H3N2, H5N1, H7N7, H1N2, H9N2, H7N2, H7N3, and H10N7 subtypes, have been confirmed to infect humans. All combinations of the 16 HA and 9 NA subtypes have been identified in avian species. In addition, Influenza B virus and Influenza C virus can also infect humans.

Due to viral recombination, prior immunity to one strain does not necessarily confer protection to the next. Upon infection, a new virus replicates unchecked, while the host mounts a highly inflammatory primary immune response. An influenza infection produces an acute set of symptoms including headache, cough, sore throat, rhinitis, fever and general malaise. In severe cases or situations involving pre-existing pulmonary or cardiovascular disease, hospitalization is required. Pneumonia due to direct viral infection or due to secondary bacterial or viral invasion is the most frequent complication.

The outcome of influenza infection is dependent on both the virus and the host. The genetic makeup of the HA and NA genes confers virulence. For example, introduction of HA and NA genes from pandemic H5N1 strains to a relatively mild virus transforms the virus into a highly virulent strain in mice. During replication, Influenza virus utilizes host protein production machinery and as a result, causes death of the infected cell (cytopathology). Such respiratory epithelial cell destruction produces an array of alarm signals initiating an inflammatory reaction (cytokine cascade) that promotes the recruitment of inflammatory cells (e.g., neutrophils and CD4+/CD8+ T cells) to the delicate surface of the lung, leading to consolidation of air spaces and a decline in arterial oxygen saturation. In eliminating the virus, the host response causes further respiratory cell death, and the responding inflammatory cells (e.g., T cells) produce an additional battery of inflammatory mediators (e.g., TNFα and IFNγ), which in excess lead to a cytokine storm, causing capillary leak and resulting in pulmonary edema and leukocyte transudation into the airspaces, thereby initiating the acute respiratory distress syndrome (ARDS). More chronic symptoms of disease, such as cachexia, fever and appetite suppression, are directly linked to the concentration of systemic mediators/cytokines that accumulate. Therefore, the whole cascade is initiated by virus-induced cytopathology, but mortality is ultimately determined by the magnitude of the inflammation that results from the immune response. Finally, both the viral-induced cytopathology and the host inflammatory response can predispose the infected subject to secondary bacterial infection, further increasing morbidity and mortality. There is evidence that a reduction of inflammation can in some circumstances have a beneficial effect, but if the immune suppression is too great then viral induced cytopathology overwhelms the host.

Flu vaccination has been a somewhat effective measure to limit influenza morbidity. However, a vaccine against one type or subtype of influenza virus confers limited or no protection against another type or subtype of influenza. Because the influenza virus undergoes continuous mutation, antigenic drift, antigenic shift, and reassortment with animal reservoir strains, creating new combinations of HA and/or NA proteins on the viral surface, yearly reformulation of the vaccine is required. There can be a mismatch between the viral strain present in the vaccine and that circulating, thereby reducing the effectiveness of flu vaccines. Furthermore, although current vaccines based on inactivated viruses are generally able to prevent illness in approximately 70-80% of healthy individuals under age 65, this percentage is far lower in the elderly or immuno-compromised subjects.

Currently, two classes of antiviral drugs are approved to treat influenza, neuraminidase inhibitors (e.g., Tamiflu® and Relenza®) and adamantane derivatives (e.g., amantadine and rimantadine). The neuraminidase inhibitors block the activity of neuraminidase (NA) surface protein and halt viral egress. The adamantane derivatives target the viral M2 protein and prevent the virus from uncoating and releasing its genetic material into the cell. However, there are increasing reports of emerging viral resistance to both classes of antivirals. Due to large scale resistance, the Centers for Disease Control and Prevention and others have recommended against using adamantane derivatives for the treatment or prophylaxis of Influenza virus. Many of the current anti-viral therapies are directed towards targeting viral components and are therefore prone to compensatory viral escape/mutation mechanisms.

Thus, there is an urgent need for alternative therapies to treat influenza and reduce the morbidity and morality associated with influenza infections.

PDE4 modulators potently inhibit TNF-α and IL-12 production, and exhibit modest inhibitory effects on LPS induced IL1β. See, e.g., L. G. Corral, et al., *J. Immunol.*, 163: 380-386 (1999). PDE4 is one of the major phosphodiesterase isoenzymes found in human myeloid and lymphoid lineage cells. The enzyme plays a crucial part in regulating cellular activity by degrading the ubiquitous second messenger cAMP and maintaining it at low intracellular levels Inhibition of PDE4 activity results in increased cAMP levels leading to the modulation of LPS induced cytokines including inhibition of TNF-α production in monocytes as well as in lymphocytes.

A number of studies have been conducted with the aim of providing compounds that can safely and effectively be used to treat diseases associated with abnormal production of TNF-α. See, e.g., Marriott, J. B., et al., *Expert Opin. Biol. Ther.* 1(4):1-8 (2001); G. W. Muller, et al., *Journal of Medicinal Chemistry*, 39(17): 3238-3240 (1996); and G. W. Muller, et al., *Bioorganic & Medicinal Chemistry Letters*, 8: 2669-2674 (1998). Some studies have focused on a group of compounds selected for their capacity to potently inhibit TNF-α production by LPS stimulated PBMC. L. G. Corral, et al., *Ann. Rheum. Dis.*, 58 (suppl I): 1107-1113 (1999). These compounds, often referred to as immunomodulatory compounds, show not only potent inhibition of TNF-α but also marked inhibition of LPS induced monocyte IL1β and IL12 production. LPS induced IL6 is also inhibited by immuno-modulatory compounds, albeit partially. These compounds are potent stimulators of LPS induced IL10. Particular examples include, but are not limited to, the substituted 2-(2,6-dioxopiperidin-3-yl)phthalimides and substituted 2-(2,6-dioxopiperidin-3-yl)-1-oxoisoindoles as described in U.S. Pat. Nos. 6,281,230 and 6,316,471. Monocyte/macrophage function is part of the Innate Immune System that serves as a first line of defense against an infection. By modulating the host's monocytes and macrophages, PDE4 modulators and immuno-modulatory compounds can change the dynamics of the response to a viral infection, such as influenza.

In addition, the innate immune system plays a critical role in the body's response to the influenza virus. The innate immune system relies on germline-encoded invariant pattern recognition receptors (PRR), such as Toll-Like Receptors (TLR), Nucleotide-binding domain and Leucine-rich-repeat Receptors (NLR), and Retinoic acid-inducible gene-1 Like Receptors (RLR). Activation of RLR, including the RIG-1-like receptors, by the signatures of influenza virus replication within the cytosol results in downstream activation of many nuclear transcription factors and the host's antiviral response. Dysregulation of the innate immune response by biological processes, or by a direct effect of the influenza virus, results in a poor immunological response by the host to the influenza virus. See, e.g., Samit R. Joshi, et al., *Yale J. Biol. Med.*, 82(4): 143-51 (2009). The compounds provided herein may have an effect on the innate immune system in general, and on the RIG-1-like receptors specifically. See, e.g., M. R. Barber, et al., *Proc. Natl. Acad. Sci. U.S.A.*, 107(13): 5913-18 (2010).

III. SUMMARY

In one embodiment, provided herein is a compound for use in the modulation of immune responses to a respiratory viral infection in a subject. In one embodiment, provided herein is a pharmaceutical composition for use in the modulation of immune responses to a respiratory viral infection in a subject. In one embodiment, provided herein is a single unit dosage form or a kit for use in the modulation of immune responses to a respiratory viral infection in a subject. In one embodiment, provided herein is a pharmaceutical composition, a single unit dosage form, or a kit for modulating immune responses to a respiratory viral infection in a subject. In one embodiment, provided herein is a method for modulating immune responses to a respiratory viral infection in a subject.

In one embodiment, provided herein is a compound for use in the treatment, prevention, amelioration, and/or delay of the onset of one or more symptoms associated with or resulting from a respiratory viral infection in a subject. In one embodiment, provided herein is a pharmaceutical composition for use in the treatment, prevention, amelioration, and/or delay of the onset of one or more symptoms associated with or resulting from a respiratory viral infection in a subject. In one embodiment, provided herein is a single unit dosage form for use in the treatment, prevention, amelioration, and/or delay of the onset of one or more symptoms associated with or resulting from a respiratory viral infection in a subject. In one embodiment, provided herein is a kit for use in the treatment, prevention, amelioration, and/or delay of the onset of one or more symptoms associated with or resulting from a respiratory viral infection in a subject. In one embodiment, provided herein is a pharmaceutical composition, a single unit dosage form, or a kit for treating, preventing, ameliorating, and/or delaying the onset of one or more symptoms associated with or resulting from a respiratory viral infection in a subject. In one embodiment, provided herein is a method for treating, preventing, ameliorating, and/or delaying the onset of one or more symptoms associated with or resulting from a respiratory viral infection in a subject.

In one embodiment, the respiratory viral infection includes, but is not limited to, influenza viral infection (e.g., seasonal flu), rhinovirus infection (e.g., common cold), coronavirus infection (e.g., Severe Acute Respiratory Syndrome and common cold), and/or paramyxovirus infection (e.g., measles). In one embodiment, the respiratory viral infection is an influenza viral infection (e.g., seasonal flu), including but not limited to, Influenza A, Influenza B, and Influenza C viral infections. In one embodiment, the respiratory viral infection is a rhinovirus infection (e.g., common cold). In one embodiment, the respiratory viral infection is a coronavirus infection (e.g., Severe Acute Respiratory Syndrome and common cold). In one embodiment, the respiratory viral infection is a paramyxovirus infection (e.g., measles).

In one embodiment, the respiratory viral infection is the infection by a certain subtype of Influenza A virus. In one embodiment, the respiratory viral infection is the infection by a certain subtype of Influenza B virus. In one embodiment, the respiratory viral infection is the infection by a certain subtype of Influenza C virus. In one embodiment, the respiratory viral infection is the infection by a certain serotype of rhinovirus. In one embodiment, the respiratory viral infection is the infection by a certain type of coronavirus. In one embodiment, the respiratory viral infection is the infection by a certain type of paramyxovirus (e.g., measles virus).

In one embodiment, provided herein is a method for treating, preventing, ameliorating, and/or delaying the onset of one or more symptoms associated with or resulting from an Influenza A viral infection in a subject. In one embodiment, provided herein is a method for treating, preventing, ameliorating, and/or delaying the onset of one or more symptoms associated with or resulting from viral infection by one or more subtype(s) of Influenza A virus. In one embodiment, the subtype of Influenza A virus includes, but is not limited to, H1N1, H2N2, H3N2, H5N1, H7N7, H1N2, H9N2, H7N2, H7N3, and H10N7 subtypes. In one embodiment, the subtype of Influenza A virus includes, but is not limited to, all combinations of H1 to H16 and N1 to N9 subtypes. In one embodiment, the subtype of Influenza A virus includes, but is not limited to, a new strain of Influenza A virus derived from viral mutation, antigenic shift, antigenic drift, and/or viral reassortment.

In one embodiment, provided herein is a method for treating, preventing, ameliorating, and/or delaying the onset of one or more symptoms associated with or resulting from the primary infection of a respiratory viral infection in a subject. In one embodiment, provided herein is a method for treating, preventing, ameliorating, and/or delaying the onset of one or more symptoms associated with or resulting from the secondary infection of a respiratory viral infection in a subject. In one embodiment, the secondary infection is caused by a virus of the same or a virus of the different type as the virus causing the primary infection. In one embodiment, the secondary infection is a bacterial infection. In one embodiment, the secondary infection is a fungal infection. In one embodiment, the symptom associated with or resulting from the respiratory viral infection includes, but is not limited to, one or more symptoms associated with or resulting from the viral infection itself and one or more symptoms associated with or resulting from complications caused by the viral infection in the infected subject.

In one embodiment, provided herein is a method for treating, preventing, ameliorating, and/or delaying the onset of one or more symptoms associated with or resulting from a respiratory viral infection in a subject, comprising administering a compound provided herein within one, two, three, four, five, six, seven, eight, nine, ten, eleven, twelve, thirteen, fourteen, fifteen, sixteen, seventeen, eighteen, nineteen, twenty, or greater than twenty days from the initial onset or diagnosis of the viral infection. In one embodiment, provided herein is a method for treating, preventing, ameliorating, and/or delaying the onset of one or more symptoms associated with or resulting from a respiratory viral infection in a subject, comprising administering a compound provided herein prior to the appearance of the initial signs of viral infection. In one embodiment, provided herein is a method for treating, preventing, ameliorating, and/or delaying the onset of one or more symptoms associated with or resulting from a respiratory viral infection in a subject, wherein the subject belongs to a high-risk sub-population, including but not limited to, very young children, school-age children, the elderly, the immuno-compromised (e.g., HIV patients), and/or the chronically ill (e.g., those diagnosed with or suffering from chronic obstructive pulmonary disease, asthma, bronchitis, or emphysema, among others).

In one embodiment, the method provided herein comprises administering a compound provided herein, or a pharmaceutically acceptable salt, solvate, hydrate, and/or stereoisomer thereof. In one embodiment, the pharmaceutical composition provided herein comprise a compound provided herein, or a pharmaceutically acceptable salt, solvate, hydrate, and/or stereoisomer thereof. In one embodiment, the single unit dosage form provided herein comprise a compound provided herein, or a pharmaceutically acceptable salt, solvate, hydrate, and/or stereoisomer thereof. In one embodiment, the kit provided herein comprise a compound provided herein, or a pharmaceutically acceptable salt, solvate, hydrate, and/or stereoisomer thereof.

In one embodiment, the method provided herein comprises administering a PDE4 modulator, or a pharmaceutically acceptable salt, solvate, hydrate, and/or stereoisomer thereof. In one embodiment, the pharmaceutical composition provided herein comprises a PDE4 modulator, or a pharmaceutically acceptable salt, solvate, hydrate, and/or stereoisomer thereof. In one embodiment, the single unit dosage form provided herein comprises a PDE4 modulator, or a pharmaceutically acceptable salt, solvate, hydrate, and/or stereoisomer thereof. In one embodiment, the kit provided herein comprises a PDE4 modulator, or a pharmaceutically acceptable salt, solvate, hydrate, and/or stereoisomer thereof.

In one embodiment, provided herein is the use of one or more PDE4 modulators in combination with other therapeutics presently used to treat, prevent, ameliorate, and/or delay the onset of one or more symptoms associated with or resulting from a respiratory viral infection in a subject. In another embodiment, provided herein is the use of one or more PDE4 modulators in combination with conventional therapies used to treat, prevent, ameliorate, and/or delay the onset of one or more symptoms associated with or resulting from a respiratory viral infection in a subject.

In one embodiment, the method provided herein comprises administering an immunomodulatory compound, or a pharmaceutically acceptable salt, solvate, hydrate, and/or stereoisomer thereof. In one embodiment, the pharmaceutical composition provided herein comprises an immunomodulatory compound, or a pharmaceutically acceptable salt, solvate, hydrate, and/or stereoisomer thereof. In one embodiment, the single unit dosage form provided herein comprises an immunomodulatory compound, or a pharmaceutically acceptable salt, solvate, hydrate, and/or stereoisomer thereof. In one embodiment, the kit provided herein comprises an immunomodulatory compound, or a pharmaceutically acceptable salt, solvate, hydrate, and/or stereoisomer thereof.

In one embodiment, provided herein is the use of one or more immuno-modulatory compounds in combination with other therapeutics presently used to treat, prevent, ameliorate, and/or delay the onset of one or more symptoms associated with or resulting from a respiratory viral infection in a subject. In another embodiment, provided herein is the use of one or more immunomodulatory compounds in combination with conventional therapies used to treat, prevent, ameliorate, and/or delay the onset of one or more symptoms associated with or resulting from a respiratory viral infection in a subject.

In one embodiment, the methods provided herein comprise administration of a compound provided herein, or a pharmaceutically acceptable salt, solvate, hydrate, and/or stereoisomer thereof, by, e.g., oral, intranasal (IN), intravenous (IV), and/or subcutaneous (SC) routes of administration. In one embodiment, the methods provided herein comprise co-administration of a compound provided herein, or a pharmaceutically acceptable salt, solvate, hydrate, and/or stereoisomer thereof, with one or more additional active agents to provide a synergistic therapeutic effect in subjects in need thereof. In one embodiment, the co-administered agent(s) may be an agent to treat, manage, prevent, and/or delay the onset of one or more symptoms associated with or resulting from the respiratory viral infection, as described herein elsewhere. In certain embodiments, the co-administered agent(s) may be dosed, e.g., orally, intranasally, intravenously, and/or subcutaneously.

In certain embodiments, the methods provided herein comprise administering a combination of two or more active agents, wherein at least one of the active agents is a PDE4 modulator or an immunomodulatory compound. In one embodiment, the second active agent includes, but is not limited to, an anti-viral compound (e.g., Tamiflu® and Relenza®), an antibiotics (e.g., antibiotics used to treat or prevent bacterial pneumonitis), a decongestant, an antihistamine, a pain reliever, a fever reducer, and/or a cough suppressant. In certain embodiments, the methods provided herein comprise administering a PDE4 modulator or an immunomodulatory compound in conjunction with an anti-viral vaccine.

IV. BRIEF DESCRIPTION OF THE DRAWINGS

FIG. 1 represents percent body weight change from day 0 to day 7 in mice infected with 50 HA units of Influenza X31 (H3N2) on day 0. The diamonds represent the mice treated with Compound 1. The squares represent the mice treated with vehicle control. The triangles represent the untreated mice.

Figure 2:
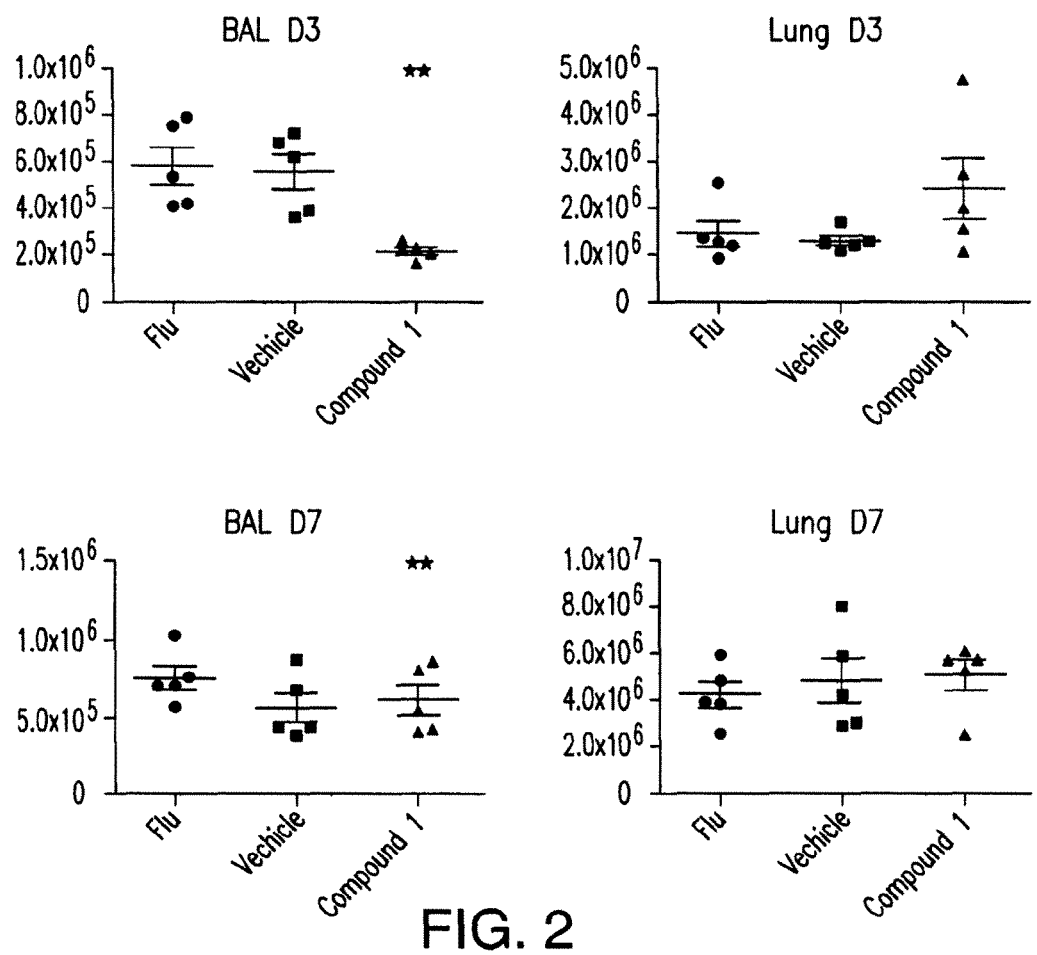
Figure 3A:
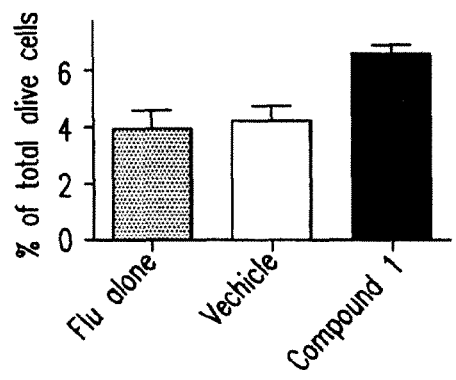
Figure 3B:
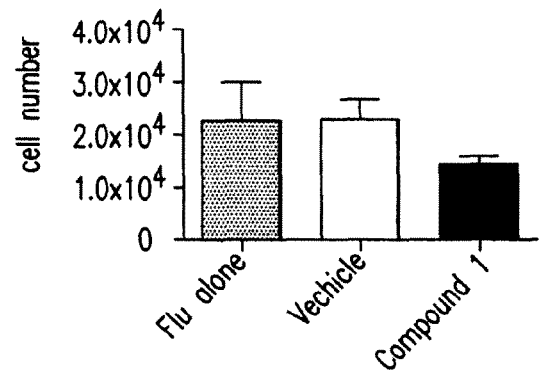
Figure 3C:
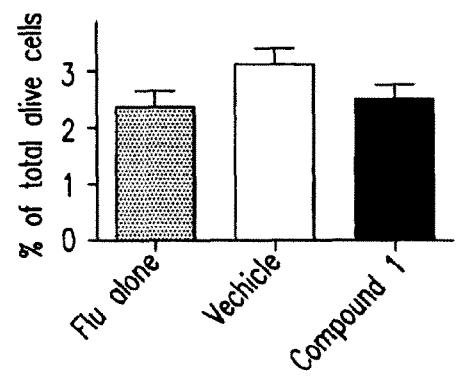
Figure 3D:
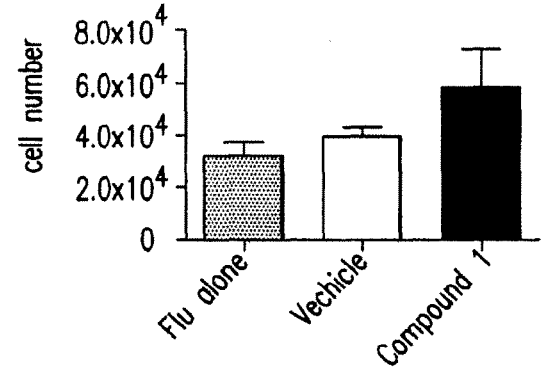

FIG. 2 represents total viable cell counts on day 3 and day 7 in the airway (BAL) and lung tissues of mice infected with 50 HA units of Influenza X31 (H3N2) on day 0. The triangles represent the mice treated with Compound 1. The squares represent the mice treated with vehicle control. The circles represent untreated mice.

FIG. 3 represents macrophage responses on day 3 in the airway (BAL) and the lung of mice infected with 50 HA units of Influenza X31 (H3N2) on day 0. FIG. 3 displays percents (A and C) and total numbers (B and D) of macrophages in the airway (A, B) and the lung (C, D) of mice, untreated, treated with vehicle control, or treated with Compound 1.

Figure 4:
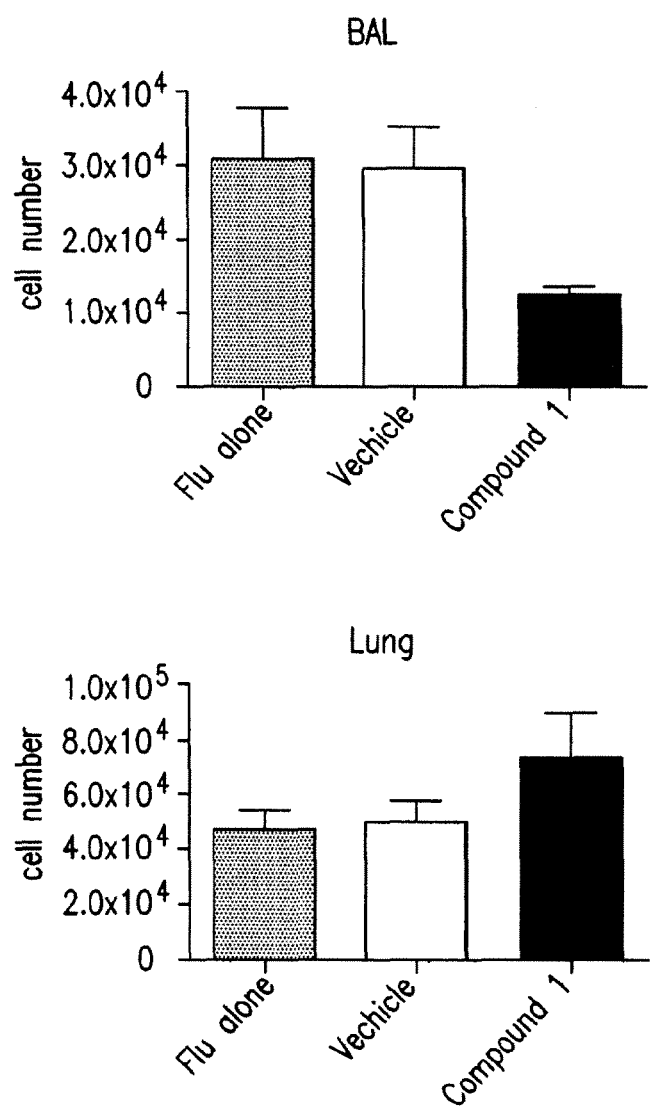
Figure 5A:
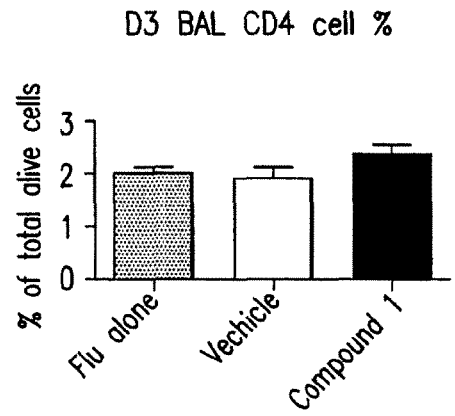
Figure 5B:
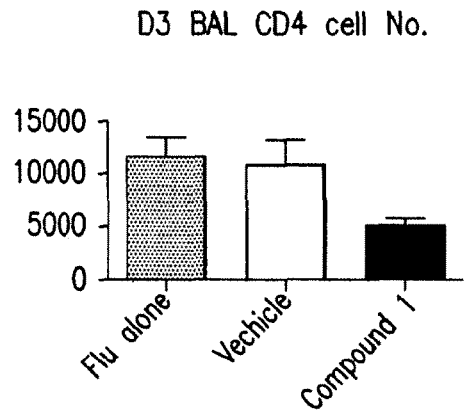
Figure 5C:
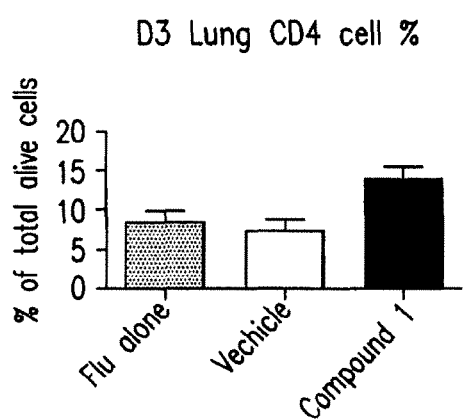
Figure 5D:
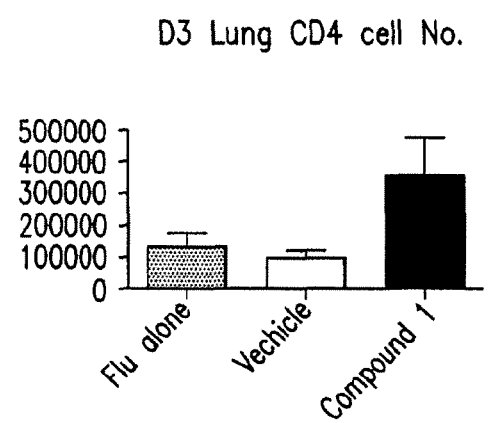
Figure 6A:
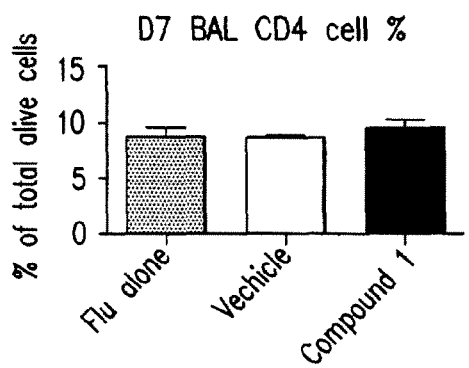
Figure 6B:
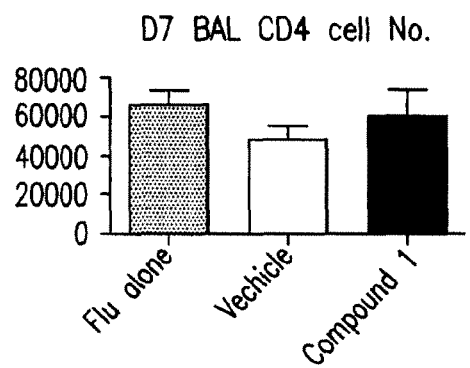
Figure 6C:
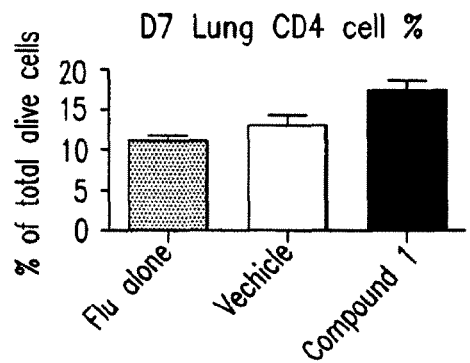
Figure 6D:
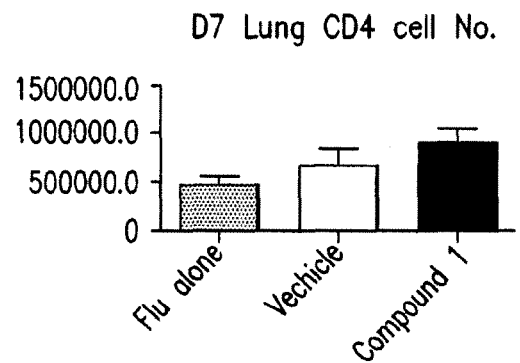
Figure 7A:
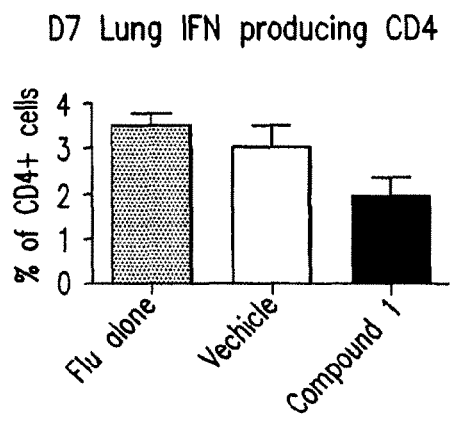
Figure 7B:
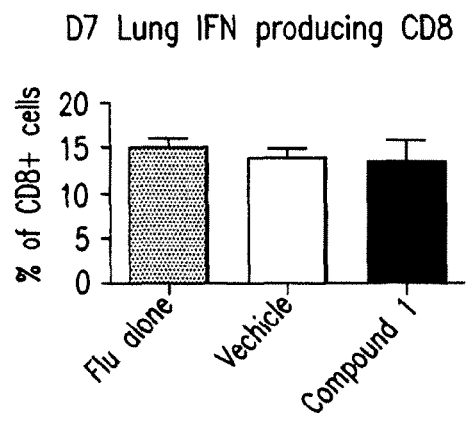
Figure 7C:
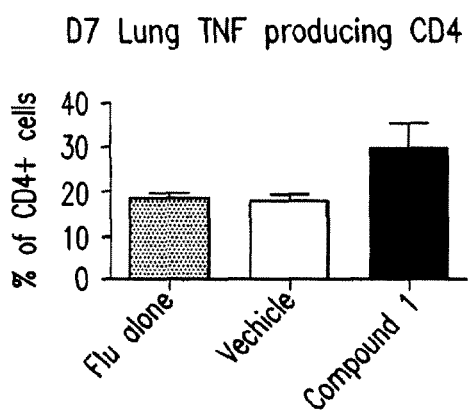
Figure 7D:
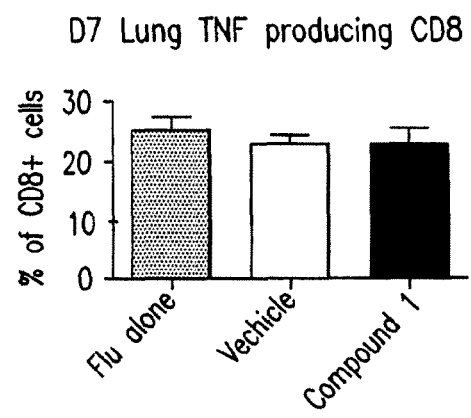

FIG. 4 represents the total cell number of neutrophils on day 3 in the airway (BAL) and the lung of mice infected with 50 HA units of Influenza X31 (H3N2) on day 0. The mice were untreated, treated with vehicle control, or treated with Compound 1.

FIG. 5 represents the percentage of CD4 cells and the total number of CD4 cells on day 3 in the airway (BAL) and the lung of mice infected with 50 HA units of Influenza X31 (H3N2) on day 0. FIG. 5 displays percents (A and C) and total numbers (B and D) of CD4 cells in the airway (A, B) and the lung (C, D) of mice, untreated, treated with vehicle control, or treated with Compound 1.

FIG. 6 represents the percentage of CD4 cells and the total number of CD4 cells on day 7 in the airway (BAL) and the lung of mice infected with 50 HA units of Influenza X31 (H3N2) on day 0. FIG. 6 displays percents (A and C) and total numbers (B and D) of CD4 cells in the airway (A, B) and the lung (C, D) of mice, untreated, treated with vehicle control, or treated with Compound 1.

FIG. 7 represents percentages of IFN or TFN producing CD4 or CD8 cells on day 7 in the lung of mice infected with 50 HA units of Influenza X31 (H3N2) on day 0. FIG. 7 displays percents of CD4 positive IFN or TNF producing T cells (A) and CD8 positive IFN or TNF producing T cells (B) in the lung of mice, untreated, treated with vehicle control, or treated with Compound 1.

Figure 8A:
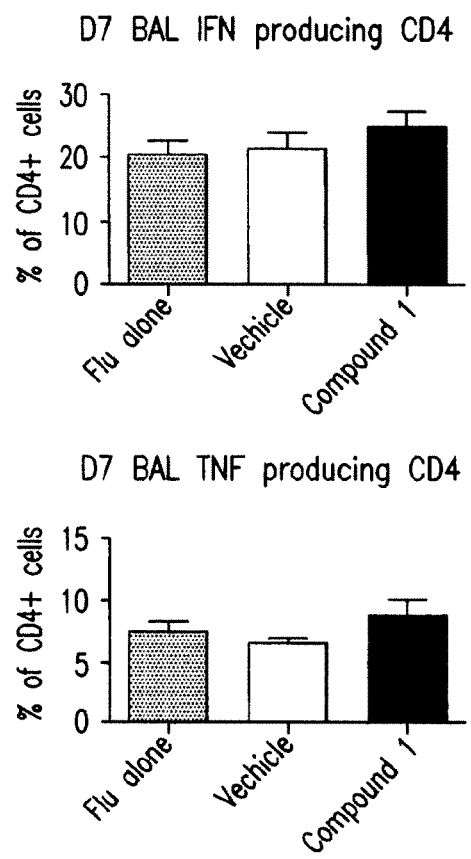
Figure 8B:
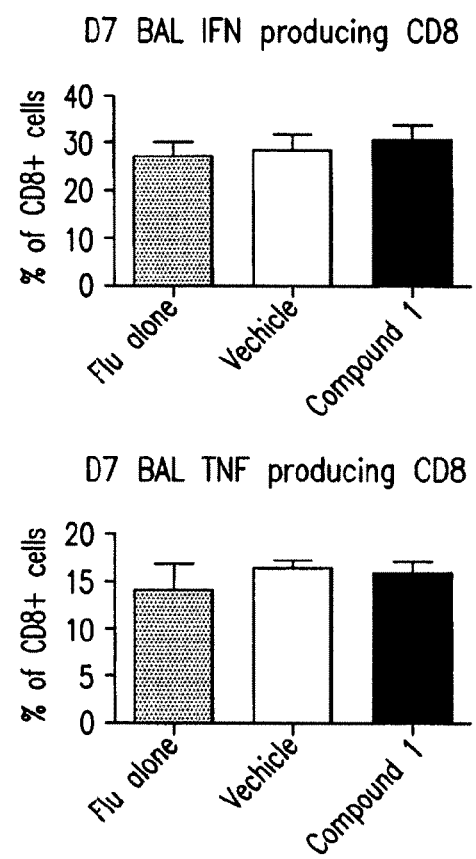

FIG. 8 represents percentages of IFN or TFN producing CD4 or CD8 cells on day 7 in the airway (BAL) of mice infected with 50 HA units of Influenza X31 (H3N2) on day 0. FIG. 8 displays percents of CD4 positive IFN or TNF producing T cells (A) and CD8 positive IFN or TNF producing T cells (B) in the airway (BAL) of mice, untreated, treated with vehicle control, or treated with Compound 1.

Figure 9A:
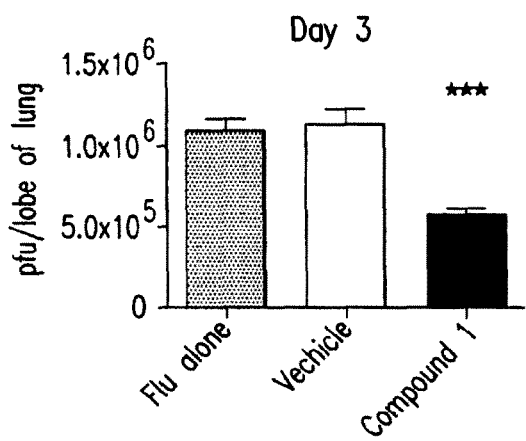
Figure 9B:
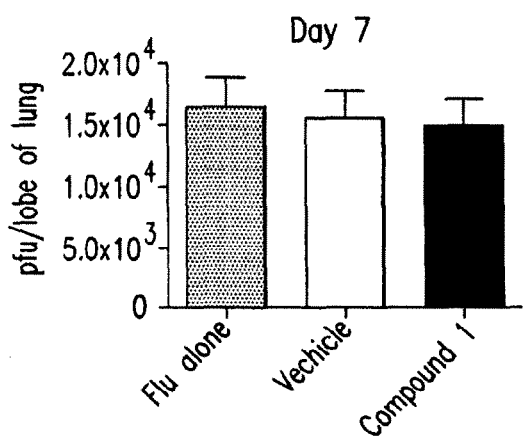

FIG. 9 represents the viral titers on day 3 and day 7 characterized by plaque assay on lung homogenates of mice infected with 50 HA units of Influenza X31 (H3N2) on day 0. The mice were untreated, treated with vehicle control, or treated with Compound 1.

V. DETAILED DESCRIPTION

Unless defined otherwise, all technical and scientific terms used herein have the same meaning as commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat," "treating" and "treatment" refer to the eradication or amelioration of a disease or disorder, or of one or more symptoms associated with or resulting from the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the diagnosis or the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with certain medical history of a disease are potential candidates for preventive regimens. In certain embodiments, subjects who have a history of recurring symptoms are potential candidates for prevention. In certain embodiments, subjects within certain social groups (e.g., medical doctors and nurses) are potential candidates for preventive regimens. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, and unless otherwise specified, the terms "ameliorate," "ameliorating" and "amelioration" of the symptoms of a particular disorder by administration of a particular compound or pharmaceutical composition refers to any lessening, whether permanent or temporary, lasting or transient, that can be attributed to or associated with the administration of the compound or composition. In one embodiment, the terms "ameliorate," "ameliorating" and "amelioration" may be used interchangeably with the terms "manage," "managing" and "management."

As used herein, and unless otherwise specified, the term "therapeutically effective amount" or "effective amount" of a compound means an amount sufficient to provide a therapeutic benefit in the treatment or management of a disease or disorder, or to delay or minimize one or more symptoms associated with the disease or disorder. A "therapeutically effective amount" or "effective amount" of a compound means an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces, delays, or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, pigs, sheep, goats, horses, dogs, cats, rabbits, rats, mice, birds, chicken, and the like. In specific embodiments, the subject is a human. In one embodiment, the terms "subject" and "patient" are used interchangeably herein in reference, for example, to a mammalian subject, such as a human.

As used herein, and unless otherwise specified, the term "modulator" encompasses both inhibitor and stimulator. Thus, a modulator of a certain receptor may inhibit or stimulate the activity of the receptor. In one embodiment, a modulator of a certain receptor is an inhibitor that inhibits the activity of the receptor. In one embodiment, a modulator of a certain receptor is a stimulator that stimulates the activity of the receptor. In one embodiment, the potency of the modulator may be measured in terms of percentage inhibition or stimulation of the activity of the receptor in the presence of a given concentration of the modulator. In one embodiment, when the modulator is an inhibitor, the potency of the modulator may be expressed as percentage inhibition of the activity of the receptor in the presence of a given concentration of the modulator. In one embodiment, at a certain concentration of an inhibitor (e.g., at about 0.001 $\mu$M, about 0.01 $\mu$M, about 0.1 $\mu$M, about 1 $\mu$M, about 3 $\mu$M, about 10 $\mu$M, or about 30 $\mu$M), the potency of the inhibitor is about 5%, about 10%, about 20%, about 30%, about 40%, about 50%, about 60%, about 70%, about 80%, about 90%, about 95%, or about 100% inhibition. In one embodiment, when the modulator is a stimulator, the potency of the modulator may be measured as percentage stimulation of the activity of the receptor in the presence of a given concentration of the modulator. In one embodiment, at a certain concentration of a stimulator (e.g., at about 0.001 $\mu$M, about 0.01 $\mu$M, about 0.1 $\mu$M, about 1 $\mu$M, about 3 $\mu$M, about 10 $\mu$M, or about 30 $\mu$M), the potency of the stimulator is about 10%, about 20%, about 30%, about 40%, about 50%, about 60%, about 70%, about 80%, about 90%, about 100%, or greater than about 100% stimulation. In one embodiment, the potency or efficacy of the modulator (e.g., an inhibitor or a stimulator) may be measured in terms of $EC_{50}$, which refers to the concentration of the compound at which 50% of the maximal response is achieved.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the terms "co-administration" and "in combination with" include the administration of two or more therapeutic agents simultaneously, concurrently or sequentially within no specific time limits unless otherwise indicated. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, and unless otherwise specified, the terms "composition," "formulation," and "dosage form" are intended to encompass products comprising the specified ingredient(s) (in the specified amounts, if indicated), as well as any product(s) which result, directly or indirectly, from combination of the specified ingredient(s) in the specified amount(s).

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. In one embodiment, by "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. See, e.g., Remington, *The Science and Practice of Pharmacy*, 21st Edition; Lippincott Williams & Wilkins: Philadelphia, Pa., 2005; *Handbook of Pharmaceutical Excipients*, 5th Edition; Rowe et al., ed., The Pharmaceutical Press and the American Pharmaceutical Association: 2005; and *Handbook of Pharmaceutical Additives*, 3rd Edition; Ash and Ash ed., Gower Publishing Company: 2007; *Pharmaceutical Preformulation and Formulation*, Gibson ed., CRC Press LLC: Boca Raton, Fla., 2004.

As used herein, and unless otherwise specified, the term "hydrate" means a compound provided herein or a salt thereof, which further includes a stoichiometric or non-stoichiometric amount of water bound by non-covalent intermolecular forces.

As used herein, and unless otherwise specified, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

B. Compounds

In one embodiment, provided herein is a compound for use in the modulation of immune responses to a respiratory viral infection in a subject. In one embodiment, provided herein is a compound for use in the treatment, prevention, amelioration, and/or delay of the onset of one or more symptoms associated with or resulting from a respiratory viral infection in a subject.

In one embodiment, the compounds provided herein include racemic, stereomerically pure, stereomerically enriched, or enantiomerically pure PDE4 modulators. In one embodiment, the compounds provided herein include racemic, stereomerically pure, stereomerically enriched, or enantiomerically pure compounds that have selective cytokine inhibitory activities, and pharmaceutically acceptable salts, solvates, hydrates, stereoisomers, and prodrugs thereof. In one embodiment, the compounds used herein are known PDE4 modulators of Celgene Corporation, NJ.

In one embodiment, provided herein is the pharmaceutically acceptable salt, solvate, hydrate, stereoisomer, and prodrug of a compound provided herein. In one embodiment, provided herein is the pharmaceutically acceptable salt, solvate, hydrate, and stereoisomer of a compound provided herein.

As used herein and unless otherwise indicated, the term "PDE4 modulators" encompasses small-molecule drugs, e.g., small organic molecules which are not peptides, proteins, nucleic acids, oligosaccharides or other macromolecules. In one embodiment, the compounds inhibit TNF-$\alpha$ production. In one embodiment, the compounds may also have a modest inhibitory effect on LPS induced IL1$\beta$ and IL12. In one embodiment, the compounds provided herein are potent PDE4 modulators. Without being limited by theory, PDE4 modulators are believed to exert the anti-inflammatory effects by elevating intracellular cAMP levels in various leukocytes, including T cells, B cells, NK cells, neutrophils, macrophages, basophils, eosinophils, and mast cells. PDE4 is also expressed in non-leukocytes such as endothelial cells, smooth muscle cells, fibroblasts, and neurons, which are also believed to contribute to inflammation.

In one embodiment, specific examples of PDE4 modulators include, but are not limited to, the cyclic imides disclosed in U.S. Pat. Nos. 5,605,914 and 5,463,063; the cycloalkyl amides and cycloalkyl nitriles of U.S. Pat. Nos. 5,728,844, 5,728,845, 5,968,945, 6,180,644 and 6,518,281; the aryl amides (for example, one embodiment being N-benzoyl-3-amino-3-(3',4'-dimethoxyphenyl)-propanamide) of U.S. Pat. Nos. 5,801,195, 5,736,570, 6,046,221 and 6,284,780; the imide/amide ethers and alcohols (for example, 3-phthalimido-3-(3',4'-dimethoxyphenyl)propan-1-ol) disclosed in U.S. Pat. No. 5,703,098; the succinimides and maleimides (for example methyl 3-(3',4',5'6'-petrahydrophthalimdo)-3-(3",4"-dimethoxyphenyl)propionate) disclosed in U.S. Pat. No. 5,658,940; imido and amido substituted alkanohydroxamic acids disclosed in U.S. Pat. No. 6,214,857 and WO 99/06041; substituted phenethylsulfones disclosed in U.S. Pat. Nos. 6,011,050 and 6,020,358; fluoroalkoxy-substituted 1,3-dihydro-isoindolyl compounds disclosed in U.S. patent application Ser. No. 10/748,085 filed on Dec. 29, 2003; substituted imides (for example, 2-phthalimido-3-(3',4'-dimethoxyphenyl)propane) disclosed in U.S. Pat. No. 6,429,221; substituted 1,3,4-oxadiazoles (for example, 2-[1-(3-cyclopentyloxy-4-methoxyphenyl)-2-(1,3,4-oxadiazole-2- yl)ethyl]-5-methylisoindoline-1,3-dione) disclosed in U.S. Pat. No. 6,326,388; cyano and carboxy derivatives of substituted styrenes (for example, 3,3-bis-(3,4-dimethoxyphenyl) acrylonitrile) disclosed in U.S. Pat. Nos. 5,929,117, 6,130,226, 6,262,101 and 6,479,554; isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606 and U.S. Pat. No. 6,667,316, for example, cyclopropyl-N-{2-[1-(3-ethoxy-4-methoxyphenyl)-2-(methylsulfonyl)ethyl]-3-oxoisoindolin-4-yl}carboxamide, cyclopropyl-N-{2-[1(S)-(3-ethoxy-4-methoxyphenyl)-2-(methylsulfonyl)ethyl]-3-oxoisoindolin-4-yl}carboxamide, and cyclopropyl-N-{2-[1(R)-(3-ethoxy-4-methoxyphenyl)-2-(methylsulfonyl)ethyl]-3-oxoisoindolin-4-yl}carboxamide; and imido and amido substituted acylhydroxamic acids (for example, (3-(1,3-dioxoisoindoline-2-yl)-3-(3-ethoxy-4-methoxyphenyl)propanoylamino)propanoate disclosed in WO 01/45702 and U.S. Pat. No. 6,699,899. Other PDE4 modulators include diphenylethylene compounds disclosed in U.S. provisional application No. 60/452,460, filed Mar. 5, 2003, the contents of which are incorporated by reference herein in their entirety. Other PDE4 modulators include isoindoline compounds disclosed in U.S. patent application Ser. Nos. 10/900,332 and 10/900,270, both filed on Jul. 28, 2004. Other PDE4 modulators include compounds disclosed in U.S. patent application Ser. No. 11/299,702, filed on Dec. 13, 2005. Other specific PDE4 modulators include 2-[1-(3-ethoxy-4-methoxyphenyl)-2-methylsulfonylethyl]-4-acetylaminoisoindoline-1,3-dione, and stereoisomers thereof (+)-2-[1-(3-ethoxy-4-methoxyphenyl)-2-methylsulfonylethyl]-4-acetylaminoisoindoline-1,3-dione was disclosed in WO 03/080049. The entireties of each of the patents and patent applications identified herein are incorporated herein by reference.

In one embodiment, additional PDE4 modulators belong to a family of synthesized chemical compounds of which typical embodiments include 3-(1,3-dioxobenzo-[f]isoindol-2-yl)-3-cyclopentyloxy-4-methoxyphenyl)propionamide and 3-(1,3-dioxo-4-azaisoindol-2-yl)-3-(3,4-dimethoxyphenyl)-propionamide.

In one embodiment, other specific PDE4 modulators belong to a class of non-polypeptide cyclic amides disclosed in U.S. Pat. Nos. 5,698,579, 5,877,200, 6,075,041 and 6,200,987, and WO 95/01348, each of which is incorporated herein by reference. Representative cyclic amides include compounds of the formula:

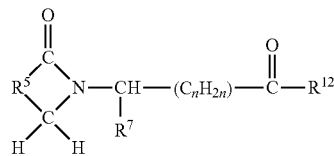

wherein n is 1, 2, or 3;

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, and halo;

$R^7$ is (i) phenyl or phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (ii) benzyl unsubstituted or substituted with 1 to 3 substituents selected from the group consisting of nitro, cyano, trifluoromethyl, carboxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (iii) naphthyl, or (iv) benzyloxy;

$R^{12}$ is —OH, alkoxy of 1 to 12 carbon atoms, or

$R^8$ is hydrogen or alkyl of 1 to 10 carbon atoms; and
$R^9$ is hydrogen, alkyl of 1 to 10 carbon atoms, —COR$^{10}$, or —SO$_2$R$^{10}$, wherein R$^{10}$ is hydrogen, alkyl of 1 to 10 carbon atoms, or phenyl.

In one embodiment, specific compounds of this class include, but are not limited to:
3-phenyl-2-(1-oxoisoindolin-2-yl)propionic acid;
3-phenyl-2-(1-oxoisoindolin-2-yl)propionamide;
3-phenyl-3-(1-oxoisoindolin-2-yl)propionic acid;
3-phenyl-3-(1-oxoisoindolin-2-yl)propionamide;
3-(4-methoxyphenyl)-3-(1-oxisoindolin-yl)propionic acid;
3-(4-methoxyphenyl)-3-(1-oxisoindolin-yl)propionamide;
3-(3,4-dimethoxyphenyl)-3-(1-oxisoindolin-2-yl)propionic acid;
3-(3,4-dimethoxy-phenyl)-3-(1-oxo-1,3-dihydroisoindol-2-yl)propionamide;
3-(3,4-dimethoxyphenyl)-3-(1-oxisoindolin-2-yl)propionamide;
3-(3,4-diethoxyphenyl)-3-(1-oxoisoindolin-yl)propionic acid;
methyl 3-(1-oxoisoindolin-2-yl)-3-(3-ethoxy-4-methoxyphenyl)propionate;
3-(1-oxoisoindolin-2-yl)-3-(3-ethoxy-4-methoxyphenyl) propionic acid;
3-(1-oxoisoindolin-2-yl)-3-(3-propoxy-4-methoxyphenyl) propionic acid;
3-(1-oxoisoindolin-2-yl)-3-(3-butoxy-4-methoxyphenyl) propionic acid;
3-(1-oxoisoindolin-2-yl)-3-(3-propoxy-4-methoxyphenyl) propionamide;
3-(1-oxoisoindolin-2-yl)-3-(3-butoxy-4-methoxyphenyl) propionamide;
methyl 3-(1-oxoisoindolin-2-yl)-3-(3-butoxy-4-methoxyphenyl)propionate; and
methyl 3-(1-oxoisoindolin-2-yl)-3-(3-propoxy-4-methoxyphenyl)propionate.

In one embodiment, other representative cyclic amides include compounds of the formula:

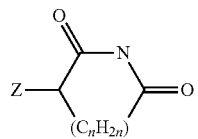

in which Z is:

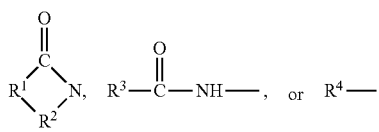

in which:

R$^1$ is the divalent residue of (i) 3,4-pyridine, (ii) pyrrolidine, (iii) imidazole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, wherein the divalent bonds of said residue are on vicinal ring carbon atoms;

R$^2$ is —CO— or —SO$_2$—;

R$^3$ is (i) phenyl substituted with 1 to 3 substituents each selected independently from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (ii) pyridyl, (iii) pyrrolyl, (iv) imidazolyl, (iv) naphthyl, (vi) thienyl, (vii) quinolyl, (viii) furyl, or (ix) indolyl;

R$^4$ is alanyl, arginyl, glycyl, phenylglycyl, histidyl, leucyl, isoleucyl, lysyl, methionyl, prolyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl; and n is 1, 2, or 3.

In one embodiment, other representative cyclic amides include compounds of the formula:

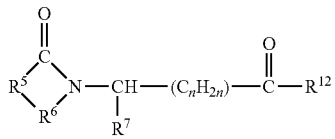

in which R$^5$ is (i) o-phenylene, unsubstituted or substituted with 1 to 4 substituents each selected independently from nitro, cyano, trifluoromethyl, carbethoxy, carbomethoxy, carbopropoxy, acetyl, carbamyl, acetoxy, carboxy, hydroxy, amino, alkylamino, dialkylamino, acylamino, alkyl of 1 to 10 carbon atoms, alkoxy of 1 to 10 carbon atoms, or halo, or (ii) the divalent residue of pyridine, pyrrolidine, imidazole, naphthalene, or thiophene, wherein the divalent bonds are on vicinal ring carbon atoms;

R$^6$ is —CO—, —CH$_2$—, or —SO$_2$—;

R$^7$ is (i) hydrogen if R$^6$ is —SO$_2$—, (ii) straight, branched, or cyclic alkyl of 1 to 12 carbon atoms, (iii) pyridyl, (iv) phenyl or phenyl substituted with one or more substituents each selected independently of the other from nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, (v) alkyl of 1 to 10 carbon atoms, (vi) benzyl unsubstituted or substituted with 1 to 3 substituents selected from the group consisting of nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, (vii) naphthyl, (viii) benzyloxy, or (ix) imidazol-4-yl methyl;

R$^{12}$ is —OH, alkoxy of 1 to 12 carbon atoms, or

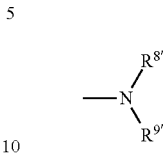

n is 0, 1, 2, or 3;

R$^{8'}$ is hydrogen or alkyl of 1 to 10 carbon atoms; and

R$^{9'}$ is hydrogen, alkyl of 1 to 10 carbon atoms, —COR$^{10}$, or —SO$_2$R$^{10}$ in which R$^{10}$ is hydrogen, alkyl of 1 to 10 carbon atoms, or phenyl.

In one embodiment, other representative imides include compounds of the formula:

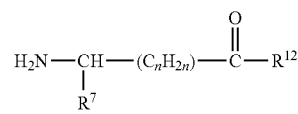

in which R$^7$ is (i) straight, branched, or cyclic alkyl of 1 to 12 carbon atoms, (ii) pyridyl, (iii) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (iv) benzyl unsubstituted or substituted with one to three substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo, (v) naphthyl, (vi) benzyloxy, or (vii) imidazol-4-ylmethyl;

R$^{12}$ is —OH, alkoxy of 1 to 12 carbon atoms, —O—CH$_2$-pyridyl, —O-benzyl or

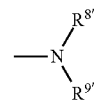

where n is 0, 1, 2, or 3;

R$^{8'}$ is hydrogen or alkyl of 1 to 10 carbon atoms; and

R$^{9'}$ is hydrogen, alkyl of 1 to 10 carbon atoms, —CH$_2$-pyridyl, benzyl, —COR$^{10}$, or —SO$_2$R$^{10}$ in which R$^{10}$ is hydrogen, alkyl of 1 to 4 carbon atoms, or phenyl.

In one embodiment, other specific PDE4 modulators include the imido and amido substituted alkanohydroxamic acids disclosed in WO 99/06041 and U.S. Pat. No. 6,214,857, each of which is incorporated herein by reference. In one embodiment, examples of such compound include, but are not limited to:

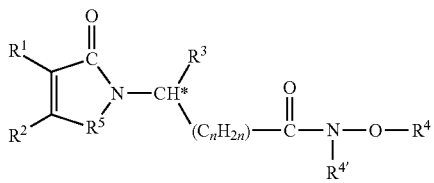

wherein each of $R^1$ and $R^2$, when taken independently of each other, is hydrogen, lower alkyl, or $R^1$ and $R^2$, when taken together with the depicted carbon atoms to which each is bound, is o-phenylene, o-naphthylene, or cyclohexene-1,2-diyl, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo;

$R^3$ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$-$C_6$-cycloalkylidenemethyl, $C_3$-$C_{10}$-alkylidenemethyl, indanyloxy, and halo;

$R^4$ is hydrogen, alkyl of 1 to 6 carbon atoms, phenyl, or benzyl;

$R^{4'}$ is hydrogen or alkyl of 1 to 6 carbon atoms;

$R^5$ is —$CH_2$—, —$CH_2$—CO—, —$SO_2$—, —S—, or —NHCO—; and n is 0, 1, or 2.

In one embodiment, additional specific PDE4 modulators provided herein include, but are not limited to:
3-(3-ethoxy-4-methoxyphenyl)-N-hydroxy-3-(1-oxoisoindolinyl)propionamide;
3-(3-ethoxy-4-methoxyphenyl)-N-methoxy-3-(1-oxoisoindolinyl)propionamide;
N-benzyloxy-3-(3-ethoxy-4-methoxyphenyl)-3-phthalimidopropionamide;
N-benzyloxy-3-(3-ethoxy-4-methoxyphenyl)-3-(3-nitrophthalimido)propionamide;
N-benzyloxy-3-(3-ethoxy-4-methoxyphenyl)-3-(1-oxoisoindolinyl)propionamide;
3-(3-ethoxy-4-methoxyphenyl)-N-hydroxy-3-phthalimidopropionamide;
N-hydroxy-3-(3,4-dimethoxyphenyl)-3-phthalimidopropionamide;
3-(3-ethoxy-4-methoxyphenyl)-N-hydroxy-3-(3-nitrophthalimido)propionamide;
N-hydroxy-3-(3,4-dimethoxyphenyl)-3-(1-oxoisoindolinyl)propionamide;
3-(3-ethoxy-4-methoxyphenyl)-N-hydroxy-3-(4-methyl-phthalimido)propionamide;
3-(3-cyclopentyloxy-4-methoxyphenyl)-N-hydroxy-3-phthalimidopropionamide;
3-(3-ethoxy-4-methoxyphenyl)-N-hydroxy-3-(1,3-dioxo-2,3-dihydro-1H-benzo[f]isoindol-2-yl)propionamide;
N-hydroxy-3-{3-(2-propoxy)-4-methoxyphenyl}-3-phthalimidopropionamide;
3-(3-ethoxy-4-methoxyphenyl)-3-(3,6-difluorophthalimido)-N-hydroxypropionamide;
3-(4-aminophthalimido)-3-(3-ethoxy-4-methoxyphenyl)-N-hydroxypropionamide;
3-(3-aminophthalimido)-3-(3-ethoxy-4-methoxyphenyl)-N-hydroxypropionamide;
3-(3-acetoamidophthalimido)-3-(3-ethoxy-4-methoxyphenyl)-N-hydroxypropionamide;
N-hydroxy-3-(3,4-dimethoxyphenyl)-3-(1-oxoisoindolinyl)propionamide;
3-(3-cyclopentyloxy-4-methoxyphenyl)-N-hydroxy-3-(1-oxoisoindolinyl)propionamide; and
N-benzyloxy-3-(3-ethoxy-4-methoxyphenyl)-3-(3-nitrophthalimido)propionamide.

In one embodiment, additional PDE4 modulators provided herein include the substituted phenethylsulfones substituted on the phenyl group with a oxoisoindine group. In one embodiment, examples of such compounds include, but are not limited to, those disclosed in U.S. Pat. No. 6,020,358, which is incorporated herein by reference, which include the following:

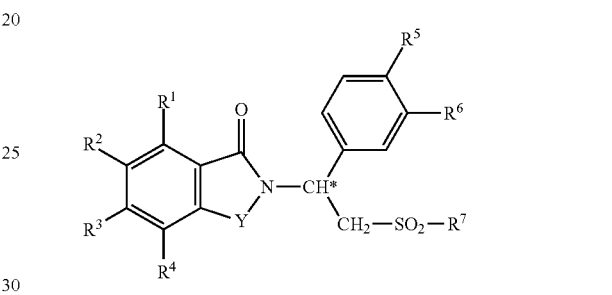

wherein the carbon atom designated * constitutes a center of chirality;

Y is C=O, $CH_2$, $SO_2$, or $CH_2C$=O; each of $R^1$, $R^2$, $R^3$, and $R^4$, independently of the others, is hydrogen, halo, alkyl of 1 to 4 carbon atoms, alkoxy of 1 to 4 carbon atoms, nitro, cyano, hydroxy, or —$NR^8R^9$; or any two of $R^1$, $R^2$, $R^3$, and $R^4$ on adjacent carbon atoms, together with the depicted phenylene ring are naphthylidene;

each of $R^5$ and $R^6$, independently of the other, is hydrogen, alkyl of 1 to 4 carbon atoms, alkoxy of 1 to 4 carbon atoms, cyano, or cycloalkoxy of up to 18 carbon atoms;

$R^7$ is hydroxy, alkyl of 1 to 8 carbon atoms, phenyl, benzyl, or $NR^{8'}R^{9'}$;

each of $R^8$ and $R^9$ taken independently of the other is hydrogen, alkyl of 1 to 8 carbon atoms, phenyl, or benzyl, or one of $R^8$ and $R^9$ is hydrogen and the other is —$COR^{10}$ or —$SO_2R^{10}$, or $R^8$ and $R^9$ taken together are tetramethylene, pentamethylene, hexamethylene, or —$CH_2CH_2X^1CH_2CH_2$— in which $X^1$ is —O—, —S— or —NH—; and each of $R^{8'}$ and $R^{9'}$ taken independently of the other is hydrogen, alkyl of 1 to 8 carbon atoms, phenyl, or benzyl, or one of $R^{8'}$ and $R^{9'}$ is hydrogen and the other is —$COR^{10'}$ or —$SO_2R^{10'}$, or $R^{8'}$ and $R^{9'}$ taken together are tetramethylene, pentamethylene, hexamethylene, or —$CH_2CH_2X^2CH_2CH_2$— in which $X^2$ is —O—, —S—, or —NH—.

It will be appreciated that while for convenience the above compounds are identified as phenethylsulfones, they include sulfonamides when $R^7$ is $NR^{8'}R^{9'}$.

In one embodiment, specific groups of such compounds are those in which Y is C=O or $CH_2$.

In one embodiment, a further specific group of such compounds are those in which each of $R^1$, $R^2$, $R^3$, and $R^4$ independently of the others, is hydrogen, halo, methyl, ethyl, methoxy, ethoxy, nitro, cyano, hydroxy, or —$NR^8R^9$ in which each of $R^8$ and $R^9$ taken independently of the other is hydrogen or methyl or one of $R^8$ and $R^9$ is hydrogen and the other is —COCH$_3$.

In one embodiment, provided herein are compounds in which one of $R^1$, $R^2$, $R^3$, and $R^4$ is —NH$_2$ and the remaining of $R^1$, $R^2$, $R^3$, and $R^4$ are hydrogen.

In one embodiment, provided herein are compounds in which one of $R^1$, $R^2$, $R^3$, and $R^4$ is —NHCOCH$_3$ and the remaining of $R^1$, $R^2$, $R^3$, and $R^4$ are hydrogen.

In one embodiment, provided herein are compounds in which one of $R^1$, $R^2$, $R^3$, and $R^4$ is —N(CH$_3$)$_2$ and the remaining of $R^1$, $R^2$, $R^3$, and $R^4$ are hydrogen.

In one embodiment, a further group of such compounds are those in which one of $R^1$, $R^2$, $R^3$, and $R^4$ is methyl and the remaining of $R^1$, $R^2$, $R^3$, and $R^4$ are hydrogen.

In one embodiment, provided herein are compounds in which one of $R^1$, $R^2$, $R^3$, and $R^4$ is fluoro and the remaining of $R^1$, $R^2$, $R^3$, and $R^4$ are hydrogen.

In one embodiment, provided herein are compounds in which each of $R^5$ and $R^6$, independently of the other, is hydrogen, methyl, ethyl, propyl, methoxy, ethoxy, propoxy, cyclopentoxy, or cyclohexoxy.

In one embodiment, provided herein are compounds in which $R^5$ is methoxy and $R^6$ is monocycloalkoxy, polycycloalkoxy, and benzocycloalkoxy.

In one embodiment, provided herein are compounds in which $R^5$ is methoxy and $R^6$ is ethoxy.

In one embodiment, provided herein are compounds in which $R^7$ is hydroxy, methyl, ethyl, phenyl, benzyl, or $NR^{8'}R^{9'}$ in which each of $R^{8'}$ and $R^{9'}$ taken independently of the other is hydrogen or methyl.

In one embodiment, provided herein are compounds in which $R^7$ is methyl, ethyl, phenyl, benzyl or $NR^{8'}R^{9'}$ in which each of $R^{8'}$ and $R^{9'}$ taken independently of the other is hydrogen or methyl.

In one embodiment, provided herein are compounds in which $R^7$ is methyl.

In one embodiment, provided herein are compounds in which $R^7$ is $NR^{8'}R^{9'}$ in which each of $R^{8'}$ and $R^{9'}$ taken independently of the other is hydrogen or methyl.

In one embodiment, additional PDE4 modulators include fluoroalkoxy-substituted 1,3-dihydro-isoindolyl compounds disclosed in U.S. patent application Ser. No. 10/748,085 filed on Dec. 29, 2003, which is incorporated herein by reference. In one embodiment, representative compounds are of formula:

wherein:
Y is —C(O)—, —CH$_2$, —CH$_2$C(O)—, —C(O)CH$_2$—, or SO$_2$;
Z is —H, —C(O)R$^3$, —(C$_{0-1}$-alkyl)-SO$_2$—(C$_{1-4}$-alkyl), —C$_{1-8}$-alkyl, —CH$_2$OH, CH$_2$(O)(C$_{1-8}$-alkyl) or —CN;
R$_1$ and R$_2$ are each independently —CHF$_2$, —C$_{1-8}$-alkyl, —C$_{3-18}$-cycloalkyl, or —(C$_{1-10}$-alkyl)(C$_{3-18}$-cycloalkyl), and at least one of R$_1$ and R$_2$ is CHF$_2$;

R$^3$ is —NR$^4$R$^5$, -alkyl, —OH, —O-alkyl, phenyl, benzyl, substituted phenyl, or substituted benzyl;
R$^4$ and R$^5$ are each independently —H, —C$_{1-8}$-alkyl, —OH, —OC(O)R$^6$;
R$^6$ is —C$_{1-8}$-alkyl, -amino(C$_{1-8}$-alkyl), -phenyl, -benzyl, or -aryl;
X$_1$, X$_2$, X$_3$, and X$_4$ are each independently —H, -halogen, -nitro, —NH$_2$, —CF$_3$, —C$_{1-6}$-alkyl, —(C$_{0-4}$-alkyl)-(C$_{3-6}$-cycloalkyl), (C$_{0-4}$-alkyl)-NR$^7$R$^8$, (C$_{0-4}$-alkyl)-N(H)C(O)—(R$^8$), (C$_{0-4}$-alkyl)-N(H)C(O)N(R$^7$R$^8$), (C$_{0-4}$-alkyl)-N(H)C(O)O(R$^8$), (C$_{0-4}$-alkyl)-OR$^8$, (C$_{0-4}$-alkyl)-imidazolyl, (C$_{0-4}$-alkyl)-pyrrolyl, (C$_{0-4}$-alkyl)-oxadiazolyl, or (C$_{0-4}$-alkyl)-triazolyl, or two of X$_1$, X$_2$, X$_3$, and X$_4$ may be joined together to form a cycloalkyl or heterocycloalkyl ring, (e.g., X$_1$ and X$_2$, X$_2$ and X$_3$, X$_3$ and X$_4$, X$_1$ and X$_3$, X$_2$ and X$_4$, or X$_1$ and X$_4$ may form a 3, 4, 5, 6, or 7 membered ring which may be aromatic, thereby forming a bicyclic system with the isoindolyl ring); and
R$^7$ and R$^8$ are each independently H, C$_{1-9}$-alkyl, C$_{3-6}$-cycloalkyl, (C$_{1-6}$-alkyl)-(C$_{3-6}$-cycloalkyl), (C$_{1-6}$-alkyl)-N(R$^7$R$^8$), (C$_{1-6}$-alkyl)-OR$^8$, phenyl, benzyl, or aryl.

In one embodiment, additional PDE4 modulators include the enantiomerically pure compounds disclosed in U.S. patent application Ser. No. 10/392,195 filed on Mar. 19, 2003; international patent application nos. PCT/US03/08737 and PCT/US03/08738, filed on Mar. 20, 2003; U.S. provisional patent application Nos. 60/438,450 and 60/438,448 to G. Muller et al., both of which were filed on Jan. 7, 2003; U.S. provisional patent application No. 60/452,460 to G. Muller et al. filed on Mar. 5, 2003; and U.S. patent application Ser. No. 10/715,184 filed on Nov. 17, 2003, all of which are incorporated herein by reference. In one embodiment, the compounds provided herein include an enantiomer of 2-[1-(3-ethoxy-4-methoxyphenyl)-2-methylsulfonylethyl]-4-acetylaminoisoindoline-1,3-dione and an enantiomer of 3-(3,4-dimethoxy-phenyl)-3-(1-oxo-1,3-dihydro-isoindol-2-yl)-propionamide.

In one embodiment, the PDE4 modulators provided herein are 3-(3,4-dimethoxy-phenyl)-3-(1-oxo-1,3-dihydro-isoindol-2-yl)-propionamide and cyclopropanecarboxylic acid {2-[1-(3-ethoxy-4-methoxy-phenyl)-2-methanesulfonylethyl]-3-oxo-2,3-dihydro-1H-isoindol-4-yl}-amide, which are available from Celgene Corp., Warren, N.J. 3-(3,4-Dimethoxy-phenyl)-3-(1-oxo-1,3-dihydro-isoindol-2-yl)-propionamide has the following chemical structure:

In one embodiment, other specific PDE4 modulators include, but are not limited to, the cycloalkyl amides and cycloalkyl nitriles of U.S. Pat. Nos. 5,728,844, 5,728,845, 5,968,945, 6,180,644 and 6,518,281, and WO 97/08143 and WO 97/23457, each of which is incorporated herein by reference. In one embodiment, representative compounds are of formula:

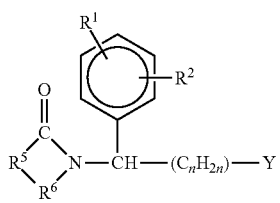

wherein:

one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl, bicycloalkyl, or benzocycloalkyl of up to 18 carbon atoms;

X is a carbon-carbon bond, —$CH_2$—, or —O—;

$R^5$ is (i) o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, or lower alkoxy; (ii) a vicinally divalent residue of pyridine, pyrrolidine, imidazole, naphthalene, or thiophene, wherein the divalent bonds are on vicinal ring carbon atoms; (iii) a vicinally divalent cycloalkyl or cycloalkenyl of 4-10 carbon atoms, unsubstituted or substituted with 1 to 3 substituents each selected independently from the group consisting of nitro, cyano, halo, trifluoromethyl, carbo(lower)alkoxy, acetyl, carbamoyl, acetoxy, carboxy, hydroxy, amino, lower alkylamino, lower alkyl, lower alkoxy, or phenyl; (iv) vinylene di-substituted with lower alkyl; or (v) ethylene, unsubstituted or monosubstituted or disubstituted with lower alkyl;

$R^6$ is —CO—, —$CH_2$—, or —$CH_2CO$—;

Y is —COZ, —C≡N, —$OR^8$, lower alkyl, or aryl;

Z is —$NH_2$, —OH, —$NHR^9$, —$R^9$, or —$OR^9$ $R^8$ is hydrogen or lower alkyl;

$R^9$ is lower alkyl or benzyl; and, n is 0, 1, 2, or 3.

In another embodiment, one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl of up to 10 carbon atoms, polycycloalkyl of up to 10 carbon atoms, or benzocyclic alkyl of up to 10 carbon atoms;

X is —$CH_2$—, or —O—;

$R^5$ is (i) the vicinally divalent residue of pyridine, pyrrolidine, imidazole, naphthalene, or thiophene, wherein the two bonds of the divalent residue are on vicinal ring carbon atoms;

(ii) a vicinally divalent cycloalkyl of 4-10 carbon atoms, unsubstituted or substituted with 1 to 3 substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl;

(iii) di-substituted vinylene, substituted with nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

(iv) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

$R^6$ is —CO—, —$CH_2$—, or —$CH_2CO$—;

Y is —COX, —C≡N, —$OR^8$, alkyl of 1 to 5 carbon atoms, or aryl;

X is —$NH_2$, —OH, —NHR, —$R^9$, —$OR^9$, or alkyl of 1 to 5 carbon atoms;

$R^8$ is hydrogen or lower alkyl;

$R^9$ is alkyl or benzyl; and, n is 0, 1, 2, or 3.

In another embodiment, one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, $HF_2CO$, $F_3CO$, or $R^3$—X—;

$R^3$ is monocycloalkyl, bicycloalkyl, benzocyclo alkyl of up to 18 carbon atoms, tetrahydropyran, or tetrahydrofuran;

X is a carbon-carbon bond, —$CH_2$—, —O—, or —N=;

$R^5$ is (i) o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, or lower alkoxy; (ii) a vicinally divalent residue of pyridine, pyrrolidine, imidazole, naphthalene, or thiophene, wherein the divalent bonds are on vicinal ring carbon atoms; (iii) a vicinally divalent cycloalkyl or cycloalkenyl of 4-10 carbon atoms, unsubstituted or substituted with 1 or more substituents each selected independently from the group consisting of nitro, cyano, halo, trifluoromethyl, carbo(lower)alkoxy, acetyl, carbamoyl, acetoxy, carboxy, hydroxy, amino, lower alkylamino, lower alkyl, lower alkoxy, or phenyl; (iv) vinylene di-substituted with lower alkyl; or (v) ethylene, unsubstituted or monosubstituted or disubstituted with lower alkyl;

$R^6$ is —CO—, —$CH_2$—, or —$CH_2CO$—;

Y is —COX, —C≡N, —$OR^8$, alkyl of 1 to 5 carbon atoms, or aryl;

X is —$NH_2$, —OH, —NHR, —$R^9$, —$OR^9$, or alkyl of 1 to 5 carbon atoms;

$R^8$ is hydrogen or lower alkyl;

$R^9$ is alkyl or benzyl; and, n is 0, 1, 2, or 3.

In one embodiment, other representative compounds are of formula:

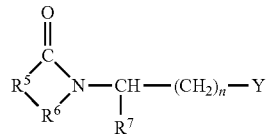

wherein:

Y is —C≡N or $CO(CH_2)_mCH_3$;

m is 0, 1, 2, or 3;

$R^5$ is (i) o-phenylene, unsubstituted or substituted with 1 to 3 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; (ii) the divalent residue of pyridine, pyrrolidine, imidazole, naphthalene, or thiophene, wherein the divalent bonds are on vicinal ring carbon atoms; (iii) a divalent cycloalkyl of 4-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo; (iv) di-substituted vinylene, substituted with nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or (v) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

$R^6$ is —CO—, —CH$_2$—, —CH$_2$CO—, or —SO$_2$—;

$R^7$ is (i) straight or branched alkyl of 1 to 12 carbon atoms; (ii) cyclic or bicyclic alkyl of 1 to 12 carbon atoms; (iii) pyridyl; (iv) phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight, branched, cyclic, or bicyclic alkyl of 1 to 10 carbon atoms, straight, branched, cyclic, or bicyclic alkoxy of 1 to 10 carbon atoms, CH$_2$R where R is a cyclic or bicyclic alkyl of 1 to 10 carbon atoms, or halo; (v) benzyl substituted with one to three substituents each selected independently from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 10 carbon atoms, or halo; (vi) naphthyl; or (vii) benzyloxy; and n is 0, 1, 2, or 3.

In another embodiment, specific PDE4 modulators are of formula:

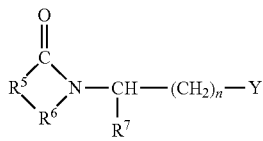

wherein:

$R^5$ is (i) the divalent residue of pyridine, pyrrolidine, imidazole, naphthalene, or thiophene, wherein the divalent bonds are on vicinal ring carbon atoms; (ii) a divalent cycloalkyl of 4-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo; (iii) di-substituted vinylene, substituted with nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or (iv) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

$R^6$ is —CO—, —CH$_2$—, —CH$_2$CO—, or —SO$_2$—;

$R^7$ is (i) cyclic or bicyclic alkyl of 4 to 12 carbon atoms; (ii) pyridyl; (iii) phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight, branched, cyclic, or bicyclic alkyl of 1 to 10 carbon atoms, straight, branched, cyclic, or bicyclic alkoxy of 1 to 10 carbon atoms, CH$_2$R where R is a cyclic or bicyclic alkyl of 1 to 10 carbon atoms, or halo; (iv) benzyl substituted with one to three substituents each selected independently from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 10 carbon atoms, or halo; (v) naphthyl; or (vi) benzyloxy;

Y is COX, —C≡N, OR$^8$, alkyl of 1 to 5 carbon atoms, or aryl;

X is —NH$_2$, —OH, —NHR, —R$^9$, —OR$^9$, or alkyl of 1 to 5 carbon atoms;

$R^8$ is hydrogen or lower alkyl;

$R^9$ is alkyl or benzyl; and n is 0, 1, 2, or 3.

In one embodiment, other specific PDE4 modulators include, but are not limited to, the aryl amides (for example, an embodiment being N-benzoyl-3-amino-3-(3',4'-dimethoxyphenyl)-propanamide) of U.S. Pat. Nos. 5,801,195, 5,736,570, 6,046,221 and 6,284,780, each of which is incorporated herein by reference. Representative compounds are of formula:

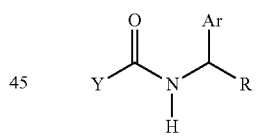

wherein:

Ar is (i) straight, branched, or cyclic, unsubstituted alkyl of 1 to 12 carbon atoms; (ii) straight, branched, or cyclic, substituted alkyl of 1 to 12 carbon atoms; (iii) phenyl; (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or halo; (v) heterocycle; or (vi) heterocycle substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo;

R is —H, alkyl of 1 to 10 carbon atoms, CH$_2$OH, CH$_2$CH$_2$OH, or CH$_2$COZ where Z is alkoxy of 1 to 10 carbon atoms, benzyloxy, or NHR$^1$ where R$^1$ is H or alkyl of 1 to 10 carbon atoms; and Y is i) a phenyl or heterocyclic ring, unsubstituted or substituted one or more substituents each selected independently one from the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo or ii) naphthyl. In one embodiment, specific examples of the compounds are of formula:

wherein:

Ar is 3,4-disubstituted phenyl where each substituent is selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

Z is alkoxy of 1 to 10 carbon atoms, benzyloxy, amino, or alkylamino of 1 to 10 carbon atoms; and Y is (i) a phenyl, unsubstituted or substituted with one or more substituents each selected, independently one from the other, from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, or (ii) naphthyl.

In one embodiment, other specific PDE4 modulators include, but are not limited to, the imide/amide ethers and alcohols (for example, 3-phthalimido-3-(3',4'-dimethoxyphenyl)propan-1-ol) disclosed in U.S. Pat. No. 5,703,098, which is incorporated herein by reference. In one embodiment, representative compounds have the formula:

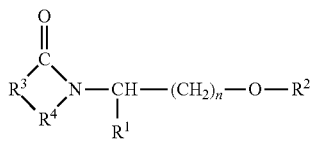

wherein:

$R^1$ is (i) straight, branched, or cyclic, unsubstituted alkyl of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, acylamino, alkylamino, di(alkyl)amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, and halo;

$R^2$ is hydrogen, alkyl of 1 to 8 carbon atoms, benzyl, pyridylmethyl, or alkoxymethyl;

$R^3$ is (i) ethylene, (ii) vinylene, (iii) a branched alkylene of 3 to 10 carbon atoms, (iv) a branched alkenylene of 3 to 10 carbon atoms, (v) cycloalkylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vi) cycloalkenylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vii) o-phenylene unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (viii) naphthyl, or (ix) pyridyl;

$R^4$ is —CX—, —CH$_2$— or —CH$_2$CX—;

X is O or S; and n is 0, 1, 2, or 3.

In one embodiment, other specific PDE4 modulators include, but are not limited to, the succinimides and maleimides (for example methyl 3-(3',4',5'6'-petrahydrophthalimdo)-3-(3",4"-dimethoxyphenyl)propionate) disclosed in U.S. Pat. No. 5,658,940, which is incorporated herein by reference. In one embodiment, representative compounds are of formula:

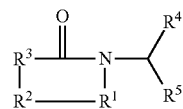

wherein:

$R^1$ is —CH$_2$—, —CH$_2$CO—, or —CO—;

$R^2$ and $R^3$ taken together are (i) ethylene unsubstituted or substituted with alkyl of 1-10 carbon atoms or phenyl, (ii) vinylene substituted with two substituents each selected, independently of the other, from the group consisting of alkyl of 1-10 carbon atoms and phenyl, or (iii) a divalent cycloalkyl of 5-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl unsubstituted or substituted with alkyl of 1-3 carbon atoms, acetoxy, carboxy, hydroxy, amino, substituted amino, alkyl of 1 to 10 carbon atoms, alkoxy of 1 to 10 carbon atoms, norbornyl, phenyl or halo;

$R^4$ is (i) straight or branched unsubstituted alkyl of 4 to 8 carbon atoms, (ii) cycloalkyl or bicycloalkyl of 5-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, branched, straight or cyclic alkyl of 1 to 10 carbon atoms, alkoxy of 1 to 10 carbon atoms, phenyl or halo, (iii) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, cycloalkyl or bicycloalkyl of 3 to 10 carbon atoms, cycloalkoxy or bicycloalkoxy of 3 to 10 carbon atoms, phenyl or halo, (iv) pyridine or pyrrolidine, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo, $R^5$ is —COX, —CN, —CH$_2$COX, alkyl of 1 to 5 carbon atoms, aryl, —CH$_2$OR, —CH$_2$ aryl, or —CH$_2$OH, X is NH$_2$, OH, NHR, or OR$^6$, R is lower alkyl; and $R^6$ is alkyl or benzyl.

In one embodiment, other specific PDE4 modulators include, but are not limited to, substituted imides (for example, 2-phthalimido-3-(3',4'-dimethoxyphenyl) propane) disclosed in U.S. Pat. No. 6,429,221, which is incorporated herein by reference. In one embodiment, representative compounds have the formula:

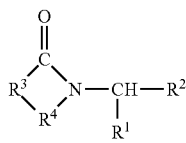

wherein:

$R^1$ is (i) straight, branched, or cyclic alkyl of 1 to 12 carbon atoms, (ii) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight or branched alkyl of 1 to 10 carbon atoms, alkoxy of 1 to 10 carbon atoms, or halo, (iii) benzyl or benzyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, or (iv)-Y-Ph where Y is a straight, branched, or cyclic alkyl of 1 to 12 carbon atoms and Ph is phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo;

$R^2$ is —H, a branched or unbranched alkyl of 1 to 10 carbon atoms, phenyl, pyridyl, heterocycle, —CH$_2$-aryl, or —CH$_2$-heterocycle;

$R^3$ is i) ethylene, ii) vinylene, iii) a branched alkylene of 3 to 10 carbon atoms, iv) a branched alkenylene of 3 to 10 carbon atoms, v) cycloalkylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo, yl)cycloalkenylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo, or vii) o-phenylene unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy 1 to 4 carbon atoms, or halo;

$R^4$ is —CX, or —CH$_2$—; and

X is O or S.

In one embodiment, other specific PDE4 modulators include, but are not limited to, substituted 1,3,4-oxadiazoles (for example, 2-[1-(3-cyclopentyloxy-4-methoxyphenyl)-2-(1,3,4-oxadiazole-2-yl)ethyl]-5-methylisoindoline-1,3-dione) disclosed in U.S. Pat. No. 6,326,388, which is incorporated herein by reference. In one embodiment, representative compounds are of formula:

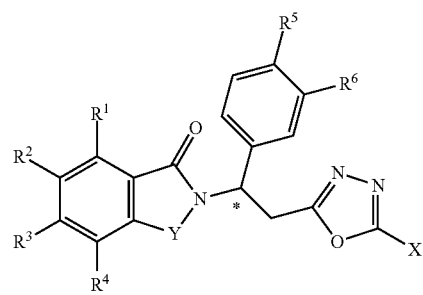

wherein:

the carbon atom designated * constitutes a center of chirality;

Y is C=O, CH$_2$, SO$_2$ or CH$_2$C=O;

X is hydrogen, or alkyl of 1 to 4 carbon atoms;

each of $R^1$, $R^2$, $R^3$, and $R^4$, independently of the others, is hydrogen, halo, trifluoromethyl, acetyl, alkyl of 1 to 8 carbon atoms, alkoxy of 1 to 4 carbon atoms, nitro, cyano, hydroxy, —CH$_2$NR$^8$R$^9$, —(CH$_2$)$_2$NR$^8$R$^9$, or —NR$^8$R$^9$ or any two of $R^1$, $R^2$, $R^3$, and $R^4$ on adjacent carbon atoms, together with the depicted benzene ring are naphthylidene, quinoline, quinoxaline, benzimidazole, benzodioxole or 2-hydroxybenzimidazole;

each of $R^5$ and $R^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;

each of $R^8$ and $R^9$, taken independently of the other is hydrogen, straight or branched alkyl of 1 to 8 carbon atoms, phenyl, benzyl, pyridyl, pyridylmethyl, or one of $R^8$ and $R^9$ is hydrogen and the other is —COR$^{10}$, or —SO$_2$R$^{10}$, or $R^8$ and $R^9$ taken together are tetramethylene, pentamethylene, hexamethylene, —CH=NCH=CH—, or —CH$_2$CH$_2$X$^1$CH$_2$CH$_2$— in which X$^1$ is —O—, —S—, or —NH—, $R^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, NR$^{11}$R$^{12}$, CH$_2$R$^{14}$R$^{15}$, or NR$^{11}$R$^{12}$, wherein $R^{14}$ and $R^{15}$, independently of each other, are hydrogen, methyl, ethyl, or propyl, and wherein $R^{11}$ and $R^{12}$, independently of each other, are hydrogen, alkyl of 1 to 8 carbon atoms, phenyl, or benzyl.

In one embodiment, specific examples of the compounds are of formula:

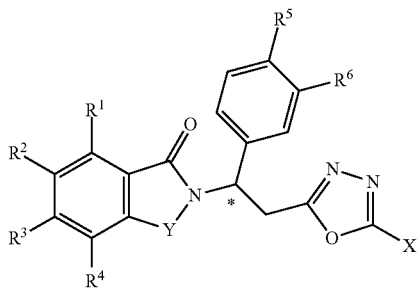

wherein:

the carbon atom designated * constitutes a center of chirality;

Y is C=O, CH$_2$, SO$_2$ or CH$_2$C=O;

X is hydrogen, or alkyl of 1 to 4 carbon atoms;

(i) each of R$^1$, R$^2$, R$^3$, and R$^4$, independently of the others, is hydrogen, halo, trifluoromethyl, acetyl, alkyl of 1 to 8 carbon atoms, alkoxy of 1 to 4 carbon atoms, nitro, cyano, hydroxy, —CH$_2$NR$^8$R$^9$, —(CH$_2$)$_2$NR$^8$R$^9$, or —NR$^8$R$^9$ or (ii) any two of R$^1$, R$^2$, R$^3$, and R$^4$ on adjacent carbon atoms, together with the depicted benzene ring to which they are bound are naphthylidene, quinoline, quinoxaline, benzimidazole, benzodioxole or 2-hydroxybenzimidazole;

each of R$^5$ and R$^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;

(i) each of R$^8$ and R$^9$, independently of the other, is hydrogen, alkyl of 1 to 8 carbon atoms, phenyl, benzyl, pyridyl, pyridylmethyl, or (ii) one of R$^8$ and R$^9$ is hydrogen and the other is —COR$^{10}$, or —SO$_2$R$^{10}$, in which R$^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, NR$^{11}$R$^{12}$, or CH$_2$NR$^{14}$R$^{15}$, wherein R$^{11}$ and R$^{12}$, independently of each other, are hydrogen, alkyl of 1 to 8 carbon atoms, phenyl, or benzyl and R$^{14}$ and R$^{15}$, independently of each other, are hydrogen, methyl, ethyl, or propyl; or (iii) R$^8$ and R$^9$ taken together are tetramethylene, pentamethylene, hexamethylene, —CH=NCH=CH—, or —CH$_2$CH$_2$X$^1$CH$_2$CH$_2$— in which X$^1$ is —O—, —S—, or —NH—.

In one embodiment, other specific PDE4 modulators include, but are not limited to, cyano and carboxy derivatives of substituted styrenes (for example, 3,3-bis-(3,4-dimethoxyphenyl)acrylonitrile) disclosed in U.S. Pat. Nos. 5,929,117, 6,130,226, 6,262,101 and 6,479,554, each of which is incorporated herein by reference. In one embodiment, representative compounds are of formula:

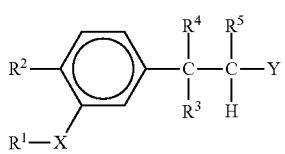

wherein:

(a) X is —O— or —(C$_n$H$_{2n}$)— in which n is 0, 1, 2, or 3, and R$^1$ is alkyl of one to 10 carbon atoms, monocycloalkyl of up to 10 carbon atoms, polycycloalkyl of up to 10 carbon atoms, or benzocyclic alkyl of up to 10 carbon atoms, or (b) X is —CH= and R$^1$ is alkylidene of up to 10 carbon atoms, monocycloalkylidene of up to 10 carbon atoms, or bicycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

R$^3$ is (i) phenyl, unsubstituted or substituted with 1 or more substituents each selected independently from nitro, cyano, halo, trifluoromethyl, carbethoxy, carbomethoxy, carbopropoxy, acetyl, carbamoyl, carbamoyl substituted with alkyl of 1 to 3 carbon atoms, acetoxy, carboxy, hydroxy, amino, amino substituted with an alkyl of 1 to 5 carbon atoms, alkyl of up to 10 carbon atoms, cycloalkyl of up to 10 carbon atoms, alkoxy of up to 10 carbon atoms, cycloalkoxy of up to 10 carbon atoms, alkylidenemethyl of up to 10 carbon atoms, cycloalkylidenemethyl of up to 10 carbon atoms, phenyl, or methylenedioxy; (ii) pyridine, substituted pyridine, pyrrolidine, imidazole, naphthalene, or thiophene; (iii) cycloalkyl of 4-10 carbon atoms, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl;

each of R$^4$ and R$^5$ taken individually is hydrogen or R$^4$ and R$^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$; R$^6$ is hydrogen or lower alkyl; and R$^7$ is alkyl or benzyl.

In one embodiment, specific examples of the compounds are of formula:

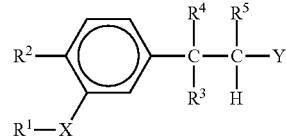

wherein:

(a) X is —O— or —(C$_n$H$_{2n}$)— in which n is 0, 1, 2, or 3, and R$^1$ is alkyl of one to 10 carbon atoms, monocycloalkyl of up to 10 carbon atoms, polycycloalkyl of up to 10 carbon atoms, or benzocyclic alkyl of up to 10 carbon atoms, or (b) X is —CH= and R$^1$ is alkylidene of up to 10 carbon atoms, monocycloalkylidene of up to 10 carbon atoms, or bicycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

R$^3$ is pyrrolidine, imidazole or thiophene unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl;

each of R$^4$ and R$^5$ taken individually is hydrogen or R$^4$ and R$^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$; R$^6$ is hydrogen or lower alkyl; and R$^7$ is alkyl or benzyl.

In one embodiment, provided herein are nitrile compounds of the formula:

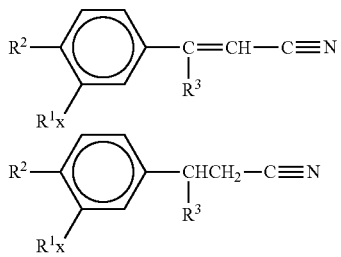

wherein:

(a) X is —O— or —(C$_n$H$_{2n}$)— in which n is 0, 1, 2, or 3, and R$^1$ is alkyl of up to 10 carbon atoms, monocycloalkyl of up to 10 carbon atoms, polycycloalkyl of up to 10 carbon atoms, or benzocyclic alkyl of up to 10 carbon atoms, or (b) X is —CH═, and R$^1$ is alkylidene of up to 10 carbon atoms or monocycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, or halo; and R$^3$ is (i) phenyl or naphthyl, unsubstituted or substituted with 1 or more substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 5 carbon atoms, alkoxy or cycloalkoxy of 1 to 10 carbon atoms; or (ii) cycloalkyl of 4 to 10 carbon atoms, unsubstituted or substituted with one or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl.

In one embodiment, provided herein is a nitrile of formula:

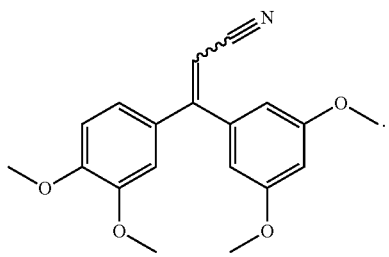

In one embodiment, other specific PDE4 modulators include, but are not limited to, isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606 and U.S. Pat. No. 6,667,316, which are incorporated herein by reference. In one embodiment, representative compounds are of formula:

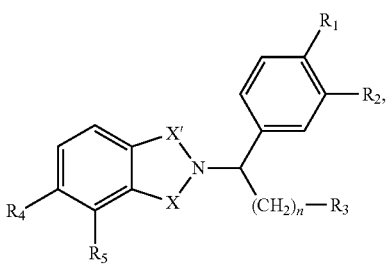

wherein:

one of X and X' is ═C═O or ═SO$_2$, and the other of X and X' is ═C═O, ═CH$_2$, ═SO$_2$ or ═CH$_2$C═O;

n is 1, 2 or 3;

R$_1$ and R$_2$ are each independently (C$_1$-C$_4$)alkyl, (C$_1$-C$_4$) alkoxy, cyano, (C$_3$-C$_{18}$)cycloalkyl, (C$_3$-C$_{18}$)cycloalkoxy or (C$_3$-C$_{18}$)cycloalkyl-methoxy;

R$_3$ is SO$_2$—Y, COZ, CN or (C$_1$-C$_6$)hydroxyalkyl, wherein:

Y is (C$_1$-C$_6$)alkyl, benzyl or phenyl;

Z is —NR$_6$R$_7$, (C$_1$-C$_6$)alkyl, benzyl or phenyl;

R$_6$ is H, (C$_1$-C$_4$)alkyl, (C$_3$-C$_{18}$)cycloalkyl, (C$_2$-C$_5$)alkanoyl, benzyl or phenyl, each of which can be optionally substituted with halo, amino or (C$_1$-C$_4$)alkyl-amino;

R$_7$ is H or (C$_1$-C$_4$)alkyl;

R$_4$ and R$_5$ are taken together to provide —NH—CH$_2$—R$_8$—, NH—CO—R$_8$—, or —N═CH—R$_8$—, wherein:

R$_8$ is CH$_2$, O, NH, CH═CH, CH═N, or N═CH; or one of R$_4$ and R$_5$ is H, and the other of R$_4$ and R$_5$ is imidazoyl, pyrrolyl, oxadiazolyl, triazolyl, or a structure of formula (A),

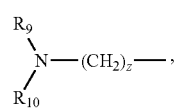

(A)

wherein:

z is 0 or 1;

R$_9$ is: H; (C$_1$-C$_4$)alkyl, (C$_3$-C$_{18}$)cycloalkyl, (C$_2$-C$_5$)alkanoyl, or (C$_4$-C$_6$)cycloalkanoyl, optionally substituted with halo, amino, (C$_1$-C$_4$)alkyl-amino, or (C$_1$-C$_4$)dialkyl-amino; phenyl; benzyl; benzoyl; (C$_2$-C$_5$)alkoxycarbonyl; (C$_3$-C$_5$) alkoxyalkylcarbonyl; N-morpholinocarbonyl; carbamoyl; N-substituted carbamoyl substituted with (C$_1$-C$_4$)alkyl; or methylsulfonyl; and R$_{10}$ is H, (C$_1$-C$_4$)alkyl, methylsulfonyl, or (C$_3$-C$_5$)alkoxyalkylcarbonyl; or R$_9$ and R$_{10}$ are taken together to provide —CH═CH—CH═CH—, —CH═CH—N═CH—, or (C$_1$-C$_2$)alkylidene, optionally substituted with amino, (C$_1$-C$_4$)alkyl-amino, or (C$_1$-C$_4$)dialkyl-amino; or R$_4$ and R$_5$ are both structures of formula (A).

In one embodiment, z is not 0 when (i) R$^3$ is —SO$_2$—Y, —COZ, or —CN and (ii) one of R$^4$ or R$^5$ is hydrogen. In another embodiment, R$^9$ and R$^{10}$, taken together, is —CH═CH—CH═CH—, —CH═CH—N═CH—, or (C$_1$-C$_2$)alkylidene substituted by amino, (C$_1$-C$_4$)alkyl-amino, or (C$_1$-C$_4$)dialkyl-amino. In another embodiment, R$_4$ and R$_5$ are both structures of formula (A).

In one embodiment, specific compounds are of formula:

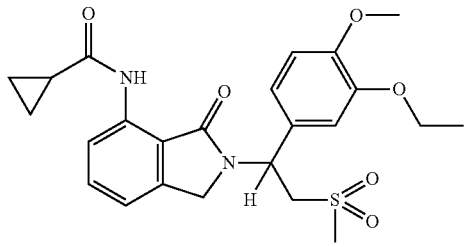 [SMILES: CCOc1cc(C(CS(C)(=O)=O)N2Cc3cccc(NC(=O)C4CC4)c3C2=O)ccc1OC]

and the enantiomers thereof.

In another embodiment, specific compounds are of formulas:

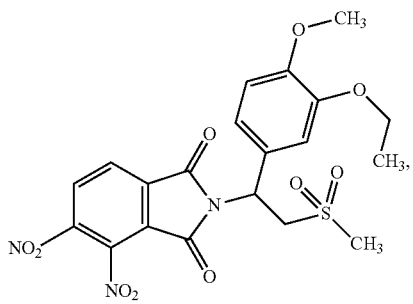

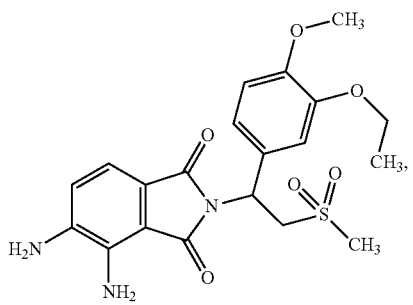

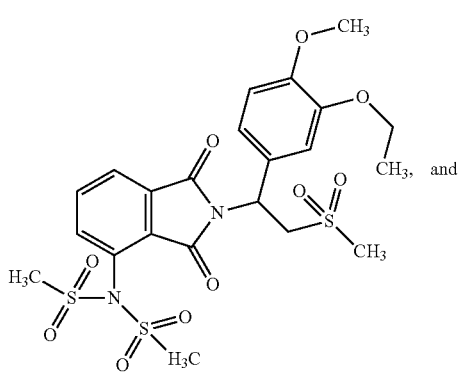

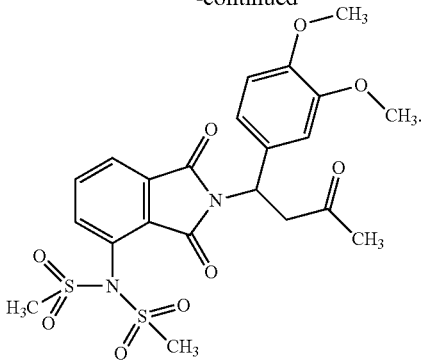

In one embodiment, further examples include, but are not limited to: 2-[1-(3-Ethoxy-4-methoxyphenyl)-2-methylsulfonylethyl]-4,5-dinitroisoindoline-1,3-dione; 2-[1-(3-Ethoxy-4-methoxyphenyl)-2-methylsulfonylethyl]-4,5-diaminoisoindoline-1,3-dione; 7-[1-(3-Ethoxy-4-methoxyphenyl)-2-methylsulfonylethyl]-3-pyrrolino[3,4-e]benzimidazole-6,8-dione; 7-[1-(3-Ethoxy-4-methoxyphenyl)-2-methylsulfonylethyl]hydro-3-pyrrolino[3,4-e]benzimidazole-2,6,8-trione; 2-[1-(3-Ethoxy-4-methoxyphenyl)-2-methylsulfonylethyl]-3-pyrrolino[3,4-f]quinoxaline-1,3-dione; Cyclopropyl-N-{2-[1-(3-ethoxy-4-methoxyphenyl)-2-methylsulfonylethyl]-1,3-dioxoisoindolin-4-yl}carboxamide; 2-Chloro-N-{2-[1-(3-ethoxy-4-methoxyphenyl)-2-methylsulfonylethyl]-1,3-dioxoisoindolin-4-yl}acetamide; 2-Amino-N-{2-[1-(3-ethoxy-4-methoxyphenyl)-2-methylsulfonylethyl]-1,3-dioxoisoindolin-4-yl}acetamide; 2-N,N-Dimethylamino-N-{2-[-(3-ethoxy-4-methoxyphenyl)-2-methylsulfonylethyl]-1,3-dioxoisoindolin-4-yl}acetamide; N-{2-[1-(3-ethoxy-4-methoxyphenyl)-2-methylsulfonylethyl]-1,3-dioxoisoindolin-4-yl}-2,2,2-trifluoroacetamide; N-{2-[1-(3-Ethoxy-4-methoxyphenyl)-2-methylsulfonylethyl]-1,3-dioxoisoindolin-4-yl}methoxycarboxamide; 4-[1-Aza-2-(dimethylamino)vinyl]-2-[1-(3-ethoxy-4-methoxyphenyl)-2-methylsulfonylethyl]isoindoline-1,3-dione; 4-[1-Aza-2-(dimethylamino)prop-1-enyl]-2-[1-(3-ethoxy-4-methoxyphenyl)-2-methylsulfonylethyl]isoindoline-1,3-dione; 2-[1-(3-Ethoxy-4-methoxyphenyl)-2-methylsulfonylethyl]-4-(5-methyl-1,3,4-oxadiazol-2-yl)isoindoline-1,3-dione; 2-[1-(3-Ethoxy-4-methoxyphenyl)-2-methylsulfonylethyl]-4-pyrrolylisoindoline-1,3-dione; 4-(Aminomethyl)-2-[1-(3-ethoxy-4-methoxyphenyl)-2-methylsulfonylethyl]-isoindoline-1,3-dione; 2-[1-(3-Ethoxy-4-methoxyphenyl)-2-methylsulfonylethyl]-4-(pyrrolylmethyl)isoindoline-1,3-dione; N-{2-[1-(3-ethoxy-4-methoxyphenyl)-3-hydroxybutyl]-1,3-dioxoisoindolin-4-yl}acetamide; N-{2-[1-(3-Ethoxy-4-methoxyphenyl)-3-oxobutyl]-1,3-dioxoisoindolin-4-yl}acetamide; N-{2-[1R-(3-ethoxy-4-methoxyphenyl)-3-hydroxybutyl]-1,3-dioxoisoindolin-4-yl}acetamide; N-{2-[1R-(3-ethoxy-4-methoxyphenyl)-3-oxobutyl]-1,3-dioxoisoindolin-4-yl}acetamide; N-{2-[1S-(3-Ethoxy-4-methoxyphenyl)-3-hydroxybutyl]-1,3-dioxoisoindolin-4-yl}acetamide; N-{2-[1S-(3-ethoxy-4-methoxyphenyl)-3-oxobutyl]-1,3-dioxoisoindolin-4-yl}acetamide; 4-Amino-2-[1-(3-ethoxy-4-methoxyphenyl)-3-hydroxybutylisoindoline-1,3-dione; 4-Amino-2-[1-(3-ethoxy-4-methoxyphenyl)-3-oxobutyl]isoindoline-1,3-dione; 2-[1-(3-Ethoxy-4-methoxyphenyl)-3-oxobutyl]-4-pyrrolylisoindoline-1,3-dione; 2-Chloro-N-{2-[1-(3-ethoxy-4-methoxyphenyl)-3-oxobutyl]-1,3-dioxoisoindol-4-yl}acetamide; 2-(Dimethylamino)-N-{2-

[1-(3-ethoxy-4-methoxyphenyl)-3-oxobutyl]-1,3-dioxoisoindolin-4-yl}acetamide; 4-Amino-2-[1R-(3-ethoxy-4-methoxyphenyl)-3-hydroxybutyl]isoindoline-1,3-dione; 4-Amino-2-[1R-(3-ethoxy-4-methoxyphenyl)-3-oxobutyl]isoindoline-1,3-dione; 2-[1R-(3-ethoxy-4-methoxyphenyl)-3-oxobutyl]-4-pyrrolylisoindoline-1,3-dione; 2-(Dimethylamino)-N-{2-[1R-(3-ethoxy-4-methoxyphenyl)-3-oxobutyl]-1,3-dioxoisoindolin-4-yl}acetamide; Cyclopentyl-N-{2-[1-(3-ethoxy-4-methoxyphenyl)-2-(methylsulfonyl)ethyl]-1,3-dioxoisoindolin-4-yl}carboxamide; 3-(Dimethylamino)-N-{2-[1-(3-ethoxy-4-methoxyphenyl)-2-(methylsulfonyl)ethyl]-1,3-dioxoisoindolin-4-yl}propanamide; 2-(Dimethylamino)-N-{2-[1-(3-ethoxy-4-methoxyphenyl)-2-(methylsulfonyl)ethyl]-1,3-dioxoisoindolin-4-yl}propanamide; N-{2-[(1R)-1-(3-ethoxy-4-methoxyphenyl)-2-(methylsulfonyl)ethyl]-1,3-dioxoisoindolin-4-yl}-2-(dimethylamino)acetamide; N-{2-[(1S)-1-(3-ethoxy-4-methoxyphenyl)-2-(methylsulfonyl)ethyl]-1,3-dioxoisoindolin-4-yl}-2-(dimethylamino)acetamide; 4-{3-[(Dimethylamino)methyl]pyrrolyl}-2-[1-(3-ethoxy-4-methoxyphenyl)-2-(methylsulfonyl)ethyl]isoindoline-1,3-dione; Cyclopropyl-N-{2-[(1S)-1-(3-ethoxy-4-methoxyphenyl)-2-(methylsulfonyl)ethyl]-1,3-dioxoisoindolin-4-yl}carboxamide; 2-[1-(3,4-dimethoxyphenyl)-2-(methylsulfonyl)ethyl]-4-pyrrolylisoindoline-1,3-dione; N-{2-[1-(3,4-dimethoxyphenyl)-2-(methylsulfonyl)ethyl]-1,3-dioxoisoindolin-4-yl}-2-(dimethylamino)acetamide; Cyclopropyl-N-{2-[1-(3,4-dimethoxyphenyl)-2-(methylsulfonyl)ethyl]-1,3-dioxoisoindolin-4-yl}carboxamide; Cyclopropyl-N-{2-[1-(3-ethoxy-4-methoxyphenyl)-2-(methylsulfonyl)ethyl]-3-oxoisoindolin-4-yl}carboxamide; 2-(Dimethylamino)-N-{2-[1-(3-ethoxy-4-methoxyphenyl)-2-(methylsulfonyl)ethyl]-3-oxoisoindolin-4-yl}acetamide; Cyclopropyl-N-{2-[(1S)-1-(3-ethoxy-4-methoxyphenyl)-2-(methylsulfonyl)ethyl]-3-oxoisoindolin-4-yl}carboxamide; Cyclopropyl-N-{2-[(1R)-1-(3-ethoxy-4-methoxyphenyl)-2-(methylsulfonyl)ethyl]-3-oxoisoindolin-4-yl}carboxamide; (3R)-3-[7-(Acetylamino)-1-oxoisoindolin-2-yl]-3-(3-ethoxy-4-methoxyphenyl)-N,N-dimethylpropanamide; (3R)-3-[7-(Cyclopropylcarbonylamino)-1-oxoisoindolin-2-yl]-3-(3-ethoxy-4-methoxyphenyl)-N,N-dimethylpropanamide; 3-{-4-[2-(Dimethylamino)acetylamino]-1,3-dioxoisoindolin-2-yl}-3-(3-ethoxy-4-methoxyphenyl)-N,N-dimethylpropanamide; (3R)-3-[7-(2-Chloroacetylamino)-1-oxoisoindolin-2-yl]-3-(3-ethoxy-4-methoxy-phenyl)-N,N-dimethylpropanamide; (3R)-3-{4-[2-(dimethylamino)acetylamino]-1,3-dioxoisoindolin-2-yl}-3-(3-ethoxy-4-methoxyphenyl)-N,N-dimethylpropanamide; 3-(1,3-Dioxo-4-pyrrolylisoindolin-2-yl)-3-(3-ethoxy-4-methoxyphenyl)-N,N-dimethylpropanamide; 2-[1-(3-Ethoxy-4-methoxyphenyl)-2-(methylsulfonyl)ethyl]-4-(imidazolyl-methyl)isoindoline-1,3-dione; N-({2-[1-(3-Ethoxy-4-methoxyphenyl)-2-(methylsulfonyl)ethyl]-1,3-dioxoisoindolin-4-yl}methyl)acetamide; 2-Chloro-N-({2-[1-(3-ethoxy-4-methoxyphenyl)-2-(methylsulfonyl)ethyl]-1,3-dioxoisoindolin-4-yl}methyl)acetamide; 2-(Dimethylamino)-N-({2-[1-(3-ethoxy-4-methoxyphenyl)-2-(methylsulfonyl)ethyl]-1,3-dioxoisoindolin-4-yl}methyl)acetamide; 4-[Bis(methylsulfonyl)amino]-2-[1-(3-ethoxy-4-methoxyphenyl)-2-(methylsulfonyl)ethyl]isoindoline-1,3-dione; 2-[1-(3-Ethoxy-4-methoxyphenyl)-2-(methylsulfonyl)ethyl]-4-[(methylsulfonyl)amino]isoindoline-1,3-dione; N-{2-[1-(3-Ethoxy-4-methoxyphenyl)-3-hydroxypentyl]-1,3-dioxoisoindolin-4-yl}acetamide; N-{2-[1-(3-Ethoxy-4-methoxyphenyl)-3-oxopentyl]1,3-dioxoisoindolin-4-yl}acetamide; 2-[(1R)-1-(3-Ethoxy-4-methoxyphenyl)-3-hydroxybutyl]-4-(pyrrolyl-methyl)isoindoline-1,3-dione; 2-[(1R)-1-(3-Ethoxy-4-methoxyphenyl)-3-oxobutyl]-4-(pyrrolylmethyl) isoindoline-1,3-dione; N-{2-[1-(3-Cyclopentyloxy-4-methoxyphenyl)-3-hydroxybutyl]-1,3-dioxoisoindolin-4-yl}acetamide; N-{2-[1-(3-Cyclopentyloxy-4-methoxyphenyl)-3-oxobutyl]-1,3-dioxoisoindolin-4-yl}acetamide; 2-[1-(3-Cyclopentyloxy-4-methoxyphenyl)-3-oxobutyl]-4-pyrrolylisoindoline-1,3-dione; 2-[1-(3,4-Dimethoxyphenyl)-3-oxobutyl]-4-[bis(methylsulfonyl)amino]isoindoline-1,3-dione; and pharmaceutically acceptable salts, solvates, hydrates and stereoisomers thereof.

In one embodiment, other specific PDE4 modulators include, but are not limited to, imido and amido substituted acylhydroxamic acids (for example, (3-(1,3-dioxoisoindoline-2-yl)-3-(3-ethoxy-4-methoxyphenyl)propanoylamino) propanoate disclosed in WO 01/45702 and U.S. Pat. No. 6,699,899, which are incorporated herein by reference. In one embodiment, representative compounds are of formula:

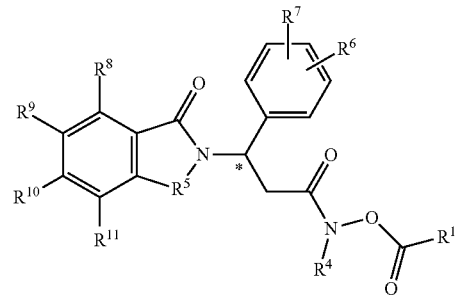

wherein:

the carbon atom designated * constitutes a center of chirality, $R^4$ is hydrogen or —(C=O)—$R^{12}$, each of $R^1$ and $R^{12}$, independently of each other, is alkyl of 1 to 6 carbon atoms, phenyl, benzyl, pyridyl methyl, pyridyl, imidazoyl, imidazolyl methyl, or $CHR*(CH_2)_n NR*R^0$, wherein $R*$ and $R^0$, independently of the other, are hydrogen, alkyl of 1 to 6 carbon atoms, phenyl, benzyl, pyridyl methyl, pyridyl, imidazoyl or imidazolylmethyl, and n=0, 1, or 2;

$R^5$ is C=O, $CH_2$, $CH_2$—CO—, or $SO_2$;

each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 6 carbon atoms, alkoxy of 1 to 6 carbon atoms, cycloalkoxy of 3 to 8 carbon atoms, halo, bicycloalkyl of up to 18 carbon atoms, tricycloalkoxy of up to 18 carbon atoms, 1-indanyloxy, 2-indanyloxy, $C_4$-$C_8$-cycloalkylidenemethyl, or $C_3$-$C_{10}$-alkylidenemethyl;

each of $R^8$, $R^9$, $R^{10}$, and $R^{11}$, independently of the others, is (i) hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, halo, or (ii) one of $R^8$, $R^9$, $R^{10}$, and $R^{11}$ is acylamino comprising a lower alkyl, and the remaining of $R^8$, $R^9$, $R^{10}$, and $R^{11}$ are hydrogen, or (iii) hydrogen if $R^8$ and $R^9$ taken together are benzo, quinoline, quinoxaline, benzimidazole, benzodioxole, 2-hydroxybenzimidazole, methylenedioxy, dialkoxy, or dialkyl, or (iv) hydrogen if $R^{10}$ and $R^{11}$, taken together are benzo, quinoline, quinoxaline, benzimidazole, benzodioxole, 2-hydroxybenzimidazole, methylenedioxy, dialkoxy, or dialkyl, or (v) hydrogen if $R^9$ and $R^{10}$ taken together are benzo.

In one embodiment, specific PDE4 modulators include, but are not limited to, 7-amido-isoindolyl compounds disclosed in U.S. patent application Ser. No. 10/798,317 filed on Mar. 12, 2004, which is incorporated herein by reference. In one embodiment, representative compounds are of formula:

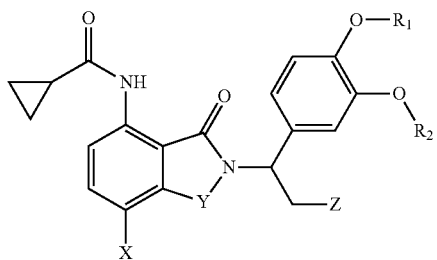

wherein:
Y is —C(O)—, —CH$_2$—, —CH$_2$C(O)— or SO$_2$;
X is H;
Z is (C$_{0-4}$-alkyl)-C(O)R$^3$, C$_{1-4}$-alkyl, (C$_{0-4}$-alkyl)-OH, (C$_{1-4}$-alkyl)-O(C$_{1-4}$-alkyl), (C$_{1-4}$-alkyl)-SO$_2$(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$alkyl)$_2$, (C$_{0-4}$-alkyl)-N(H)(OH), or CH$_2$NSO$_2$(C$_{1-4}$-alkyl);
R$_1$ and R$_2$ are independently C$_{1-8}$-alkyl, cycloalkyl, or (C$_{1-4}$-alkyl)cycloalkyl;
R$^3$ is, NR$^4$R$^5$, OH, or O—(C$_{1-8}$-alkyl);
R$^4$ is H;
R$^5$ is —OH, or —OC(O)R$^6$; and
R$^6$ is C$_{1-8}$-alkyl, amino-(C$_{1-8}$-alkyl), (C$_{1-8}$-alkyl)-(C$_{3-6}$-cycloalkyl), C$_{3-6}$-cycloalkyl, phenyl, benzyl, or aryl;
or formula:

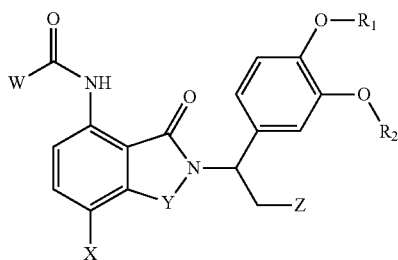

wherein:
Y is —C(O)—, —CH$_2$—, —CH$_2$C(O)—, or SO$_2$;
X is halogen, —CN, —NR$_7$R$_8$, —NO$_2$, or —CF$_3$;
Z is (C$_{0-4}$alkyl)-SO$_2$(C$_{1-4}$-alkyl), —(C$_{0-4}$-alkyl)-CN, —(C$_{0-4}$-alkyl)-C(O)R$^3$, C$_{1-4}$-alkyl, (C$_{0-4}$-alkyl)OH, (C$_{0-4}$-alkyl)O(C$_{1-4}$-alkyl), (C$_{0-4}$-alkyl)SO(C$_{1-4}$-alkyl), (C$_{0-4}$-alkyl)NH$_2$, (C$_{0-4}$-alkyl)N(C$_{1-8}$-alkyl)$_2$, (C$_{0-4}$-alkyl)N(H)(OH), (C$_{0-4}$-alkyl)-dichloropyridine or (C$_{0-4}$-alkyl)NSO$_2$(C$_{1-4}$-alkyl);
W is —C$_{3-6}$-cycloalkyl, —(C$_{1-8}$-alkyl)-(C$_{3-6}$-cycloalkyl), —(C$_{0-8}$-alkyl)-(C$_{3-6}$-cycloalkyl)NR$_7$R$_8$, (C$_{0-8}$-alkyl)-NR$_7$R$_8$, (C$_{0-4}$alkyl)-CHR$_9$—(C$_{0-4}$alkyl)-NR$_7$R$_8$;

R$_1$ and R$_2$ are independently C$_{1-8}$-alkyl, cycloalkyl, or (C$_{1-4}$-alkyl)cycloalkyl;
R$^3$ is C$_{1-8}$-alkyl, NR$^4$R$^5$, OH, or O—(C$_{1-8}$-alkyl);
R$^4$ and R$^5$ are independently H, C$_{1-8}$-alkyl, (C$_{0-8}$-alkyl)-(C$_{3-6}$-cycloalkyl), OH, or —OC(O)R$^6$;
R$^6$ is C$_{1-8}$-alkyl, (C$_{0-8}$-alkyl)-(C$_{3-6}$-cycloalkyl), amino-(C$_{1-8}$-alkyl), phenyl, benzyl, or aryl;
R$_7$ and R$_8$ are each independently H, C$_{1-8}$-alkyl, (C$_{0-8}$-alkyl)-(C$_{3-6}$-cycloalkyl), phenyl, benzyl, aryl, or can be taken together with the atom connecting them to form a 3 to 7 membered heterocycloalkyl or heteroaryl ring; and
R$_9$ is C$_{1-4}$alkyl, (C$_{0-4}$alkyl)aryl, (C$_{0-4}$alkyl)-(C$_{3-6}$-cycloalkyl), (C$_{0-4}$alkyl)-heterocycle.

In another embodiment, W is

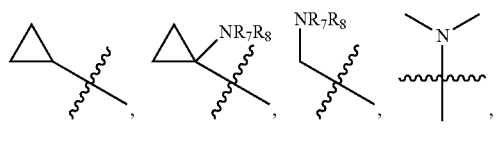

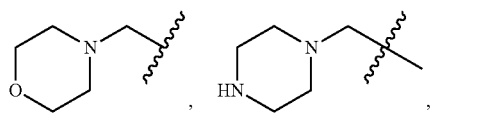

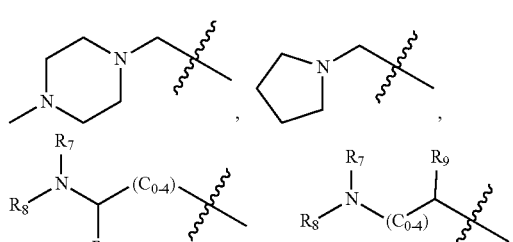

In another embodiment, representative compounds are of formula:

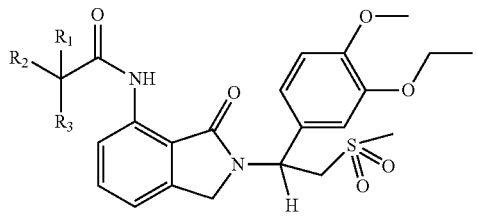

wherein:
R$_1$, R$_2$ and R$_3$ are independently H or C$_{1-8}$-alkyl, with the proviso that at least one of R$_1$, R$_2$ and R$_3$ is not H.

In one embodiment, specific PDE4 modulators include, but are not limited to, isoindoline compounds disclosed in U.S. patent application Ser. No. 10/900,332 filed on Jul. 28, 2004, which is incorporated herein by reference. In one embodiment, representative compounds are listed in Table 1 below, and pharmaceutically acceptable prodrugs, salts, solvates, hydrates, and stereoisomers thereof:

TABLE 1

| No. | Structure |
|---|---|
| 1 | 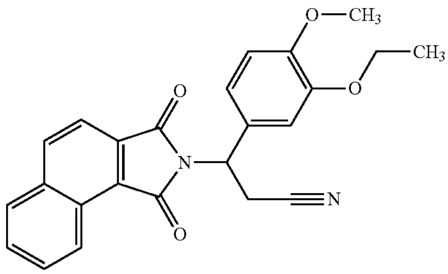 [SMILES: CCOc1cc(C(CC#N)N2C(=O)c3ccc4ccccc4c3C2=O)ccc1OC] |
| 2 | 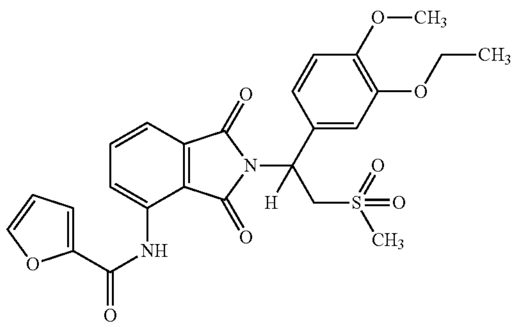 [SMILES: CCOc1cc(C(CS(C)(=O)=O)N2C(=O)c3cccc(NC(=O)c4ccco4)c3C2=O)ccc1OC] |
| 3 | 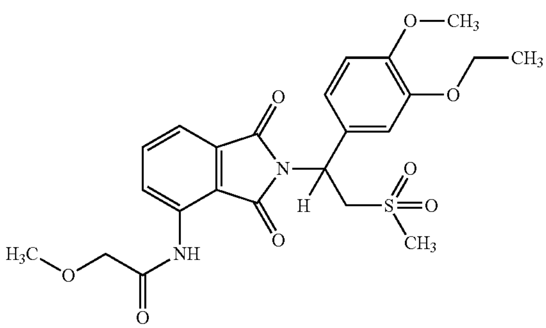 [SMILES: CCOc1cc(C(CS(C)(=O)=O)N2C(=O)c3cccc(NC(=O)COC)c3C2=O)ccc1OC] |
| 4 | 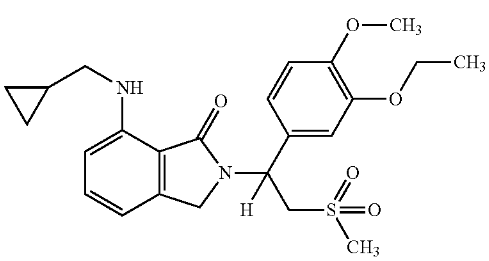 [SMILES: CCOc1cc(C(CS(C)(=O)=O)N2Cc3cccc(NCC4CC4)c3C2=O)ccc1OC] |
| 5 | 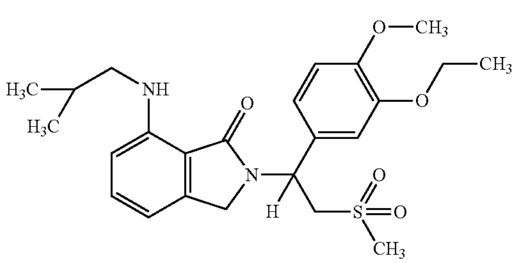 [SMILES: CCOc1cc(C(CS(C)(=O)=O)N2Cc3cccc(NCC(C)C)c3C2=O)ccc1OC] |
| 6 | |
| 7 | |
| 8 | |
| 9 | |
| 10 | |

TABLE 1-continued

| No. | Structure |
|---|---|
| 11 | 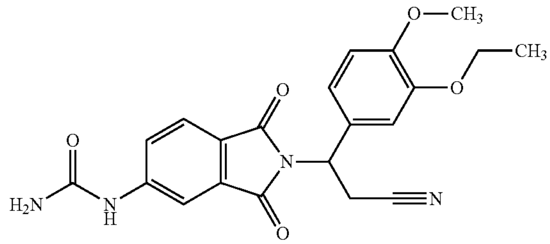 [SMILES: CCOc1cc(C(CC#N)N2C(=O)c3ccc(NC(N)=O)cc3C2=O)ccc1OC] |
| 12 | 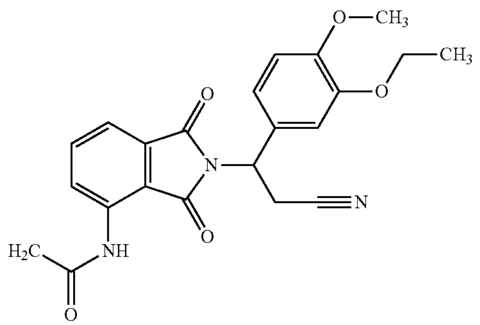 [SMILES: CCOc1cc(C(CC#N)N2C(=O)c3cccc(NC(C)=O)c3C2=O)ccc1OC] |
| 13 | 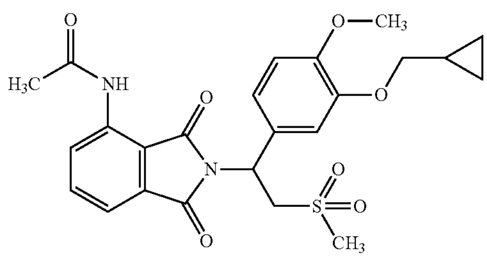 [SMILES: COc1ccc(C(CS(C)(=O)=O)N2C(=O)c3cccc(NC(C)=O)c3C2=O)cc1OCC1CC1] |
| 14 | 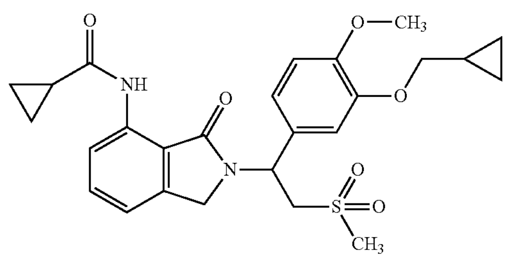 [SMILES: COc1ccc(C(CS(C)(=O)=O)N2Cc3cccc(NC(=O)C4CC4)c3C2=O)cc1OCC1CC1] |
| 15 | 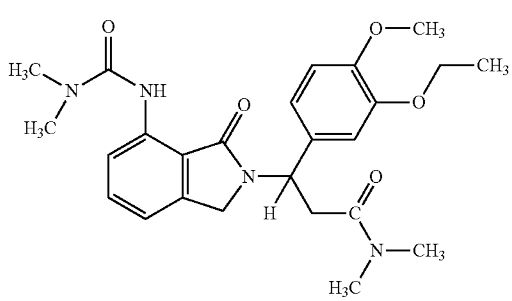 [SMILES: CCOc1cc(C(CC(=O)N(C)C)N2Cc3cccc(NC(=O)N(C)C)c3C2=O)ccc1OC] |
| 16 | |

In another embodiment, provided herein is 2-[1-(3-ethoxy-4-methoxyphenyl)-2-methylsulfonylethyl]-4,5-dinitroisoindoline-1,3-dione and its acid addition salts. In one embodiment, provided herein is a hydrochloride salt of 2-[1-(3-ethoxy-4-methoxyphenyl)-2-methylsulfonylethyl]-4,5-dinitroisoindoline-1,3-dione.

In one embodiment, specific PDE4 modulators include, but are not limited to, isoindoline compounds disclosed in U.S. patent application Ser. No. 10/900,270 filed on Jul. 28, 2004, which is incorporated herein by reference. In one embodiment, representative compounds are cyclopropanecarboxylic acid {2-[1-(3-ethoxy-4-methoxy-phenyl)-2-[1,3,4]oxadiazol-2-yl-ethyl]-3-oxo-2,3-dihydro-1H-isoindol-4-yl}-amide, which has the following chemical structure, and pharmaceutically acceptable salts, solvates, hydrates, prodrugs, and stereoisomers thereof:

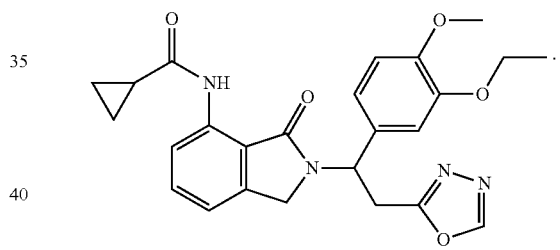

In one embodiment, specific PDE4 modulators include, but are not limited to, N-alkyl-hydroxamic acid-isoindolyl compounds disclosed in U.S. provisional application No. 60/454,149 filed on Mar. 12, 2003, and its U.S. non-provisional application entitled "N-alkyl-hydroxamic acid-isoindolyl compounds and their pharmaceutical uses" which was filed on Mar. 12, 2004 by Man et al. under U.S. Ser. No. 10/798,372, each of which is incorporated herein by reference. In one embodiment, representative compounds are of formula:

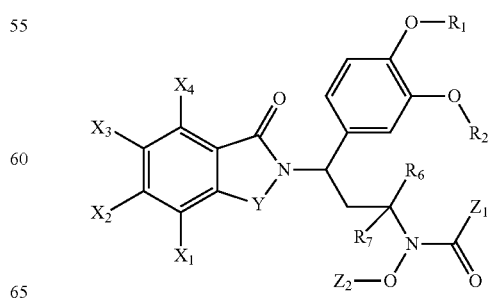

wherein:

Y is —C(O)—, —CH$_2$, —CH$_2$C(O)— or SO$_2$;

R$_1$ and R$_2$ are independently C$_{1-8}$-alkyl, CF$_2$H, CF$_3$, CH$_2$CHF$_2$, cycloalkyl, or (C$_{1-8}$-alkyl)cycloalkyl;

Z$_1$ is H, C$_{1-6}$-alkyl, —NH$_2$—NR$_3$R$_4$ or OR$_5$;

Z$_2$ is H or C(O)R$_5$;

X$_1$, X$_2$, X$_3$ and X$_4$ are each independent H, halogen, NO$_2$, OR$_3$, CF$_3$, C$_{1-6}$-alkyl, (C$_{0-4}$ alkyl)-(C$_{3-6}$-cycloalkyl), (C$_{0-4}$-alkyl)-N—(R$_8$R$_9$), (C$_{0-4}$-alkyl)-NHC(O)—(R$_8$), (C$_{0-4}$-alkyl)-NHC(O)CH(R$_8$)(R$_9$), (C$_{0-4}$-alkyl)-NHC(O)N(R$_8$R$_9$), (C$_{0-4}$-alkyl)-NHC(O)O(R$_8$), (C$_{0-4}$-alkyl)-O—R$_8$, (C$_{0-4}$-alkyl)-imidazolyl, (C$_{0-4}$-alkyl)-pyrrolyl, (C$_{0-4}$-alkyl) oxadiazolyl, (C$_{0-4}$-alkyl)-triazolyl or (C$_{0-4}$-alkyl)-heterocycle;

R$_3$, R$_4$, and R$_5$ are each independently H, C$_{1-6}$-alkyl, O—C$_{1-6}$-alkyl, phenyl, benzyl, or aryl;

R$_6$ and R$_7$ are independently H or C$_{1-6}$-alkyl; and

R$_8$ and R$_9$ are each independently H, C$_{1-9}$-alkyl, C$_{3-6}$-cycloalkyl, (C$_{1-6}$-alkyl)-(C$_{3-6}$cycloalkyl), (C$_{0-6}$-alkyl)-N(R$_4$R$_5$), (C$_{1-6}$-alkyl)-OR$_5$, phenyl, benzyl, aryl, piperidinyl, piperizinyl, pyrrolidinyl, morpholino, or C$_{3-7}$-heterocycloalkyl.

In one embodiment, specific PDE4 modulators include, but are not limited to, diphenylethylene compounds disclosed in U.S. patent application Ser. No. 10/794,931, filed on Mar. 5, 2004, which is incorporated herein by reference. In one embodiment, representative compounds are of formula:

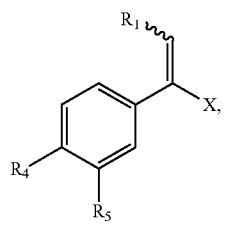

wherein:

R$_1$ is —CN, lower alkyl, —COOH, —C(O)—N(R$_9$)$_2$, —C(O)-lower alkyl, —C(O)-benzyl, —C(O)O-lower alkyl, —C(O)O-benzyl;

R$_4$ is —H, —NO$_2$, cyano, substituted or unsubstituted lower alkyl, substituted or unsubstituted alkoxy, halogen, —OH, —C(O)(R$_{10}$)$_2$, —COOH, —NH$_2$, —OC(O)—N(R$_{10}$)$_2$;

R$_5$ is substituted or unsubstituted lower alkyl, substituted or unsubstituted alkoxy, or substituted or unsubstituted alkenyl;

X is substituted or unsubstituted phenyl, substituted or unsubstituted pyridine, substituted or unsubstituted pyrrolidine, substituted or unsubstituted imidazole, substituted or unsubstituted naphthalene, substituted or unsubstituted thiophene, or substituted or unsubstituted cycloalkyl;

each occurrence of R$_9$ is independently —H or substituted or unsubstituted lower alkyl; and each occurrence of R$_{10}$ is independently —H or substituted or unsubstituted lower alkyl. In another embodiment, representative compounds are of formula:

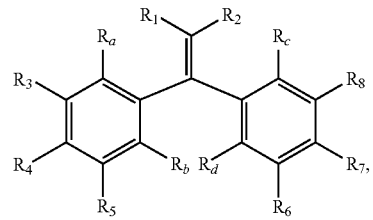

wherein:

R$_1$ and R$_2$ are independently —H, —CN, substituted or unsubstituted lower alkyl, substituted or unsubstituted alkenyl, substituted or unsubstituted alkynyl, —COOH, —C(O)-lower alkyl, —C(O)O-lower alkyl, —C(O)—N(R$_9$)$_2$, substituted or unsubstituted aryl, or substituted or unsubstituted heterocycle;

each occurrence of R$_a$, R$_b$, R$_c$ and R$_d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_3$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$, or R$_3$ with either R$_a$ or with R$_4$, together form —O—C(R$_{16}$R$_{17}$)—O— or —O—(C(R$_{16}$R$_{17}$))$_2$—O—;

R$_4$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_5$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_6$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N (R₁₀)₂, —NHC(O)NHSO₂—R₁₀, —NHC(O)—R₁₀—N(R₁₀)₂, —NHC(O)CH(R₁₀)(N(R₉)₂) or —NHC(O)—R₁₀—NH₂;

R₇ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R₉)₂, —OC(O)—R₁₀, —OC(O)—R₁₀—N(R₁₀)₂, —C(O)N(R₁₀)₂, —NHC(O)—R₁₀, —NHS(O)₂—R₁₀, —S(O)₂—R₁₀, —NHC(O)NH—R₁₀, —NHC(O)N(R₁₀)₂, —NHC(O)NHSO₂—R₁₀, —NHC(O)—R₁₀—N(R₁₀)₂, —NHC(O)CH(R₁₀)(N(R₉)₂) or —NHC(O)—R₁₀—NH₂;

R₈ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R₉)₂, —OC(O)—R₁₀, —OC(O)—R₁₀—N(R₁₀)₂, —C(O)N(R₁₀)₂, —NHC(O)—R₁₀, —NHS(O)₂—R₁₀, —S(O)₂—R₁₀, —NHC(O)NH—R₁₀, —NHC(O)N(R₁₀)₂, —NHC(O)NHSO₂—R₁₀, —NHC(O)—R₁₀—N(R₁₀)₂, —NHC(O)CH(R₁₀)(N(R₉)₂) or —NHC(O)—R₁₀—NH₂, or R₈ with either R_c or with R₇, together form —O—C(R₁₆R₁₇)—O— or —O—(C(R₁₆R₁₇))₂—O—;

each occurrence of R₉ is independently —H, substituted or unsubstituted lower alkyl, or substituted or unsubstituted cycloalkyl;

each occurrence of R₁₀ is independently substituted or unsubstituted lower alkyl, substituted or unsubstituted cycloalkyl, substituted or unsubstituted aryl, substituted or unsubstituted lower hydroxyalkyl, or R₁₀ and a nitrogen to which it is attached form a substituted or unsubstituted heterocycle, or R₁₀ is —H where appropriate; and each occurrence of R₁₆ and R₁₇ is independently —H or halogen.

In one embodiment, the compounds provided herein are 2-[1-(3-ethoxy-4-methoxyphenyl)-2-methylsulfonylethyl]-4-acetylaminoisoindoline-1,3-dione and cyclopropyl-N-{2-[1-(3-ethoxy-4-methoxyphenyl)-2-(methylsulfonyl)ethyl]-3-oxoisoindolin-4-yl}carboxamide, which respectively have the following structures:

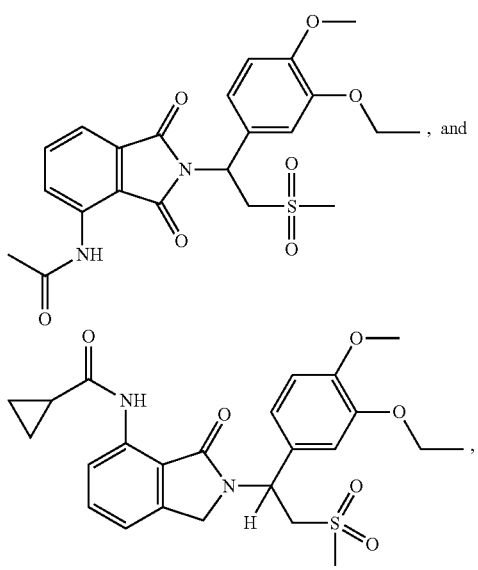

or a pharmaceutically acceptable salt, solvate, hydrate, stereoisomer or prodrug thereof. In another embodiment, stereoisomers of these compounds are also encompassed.

In one embodiment, provided herein is a compound having the following structure:

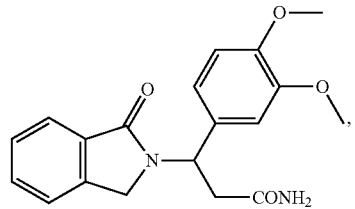 [SMILES: COc1ccc(C(CC(N)=O)N2Cc3ccccc3C2=O)cc1OC]

or a pharmaceutically acceptable salt, solvate, hydrate, stereoisomer or prodrug thereof. In another embodiment, the stereoisomers of the compound are also provided herein. In one embodiment, provided herein is a compound having the following structure:

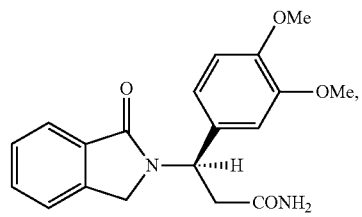 [SMILES: COc1ccc([C@@H](CC(N)=O)N2Cc3ccccc3C2=O)cc1OC]

or a pharmaceutically acceptable salt, solvate, hydrate, stereoisomer or prodrug thereof. In one embodiment, provided herein is a compound having the following structure:

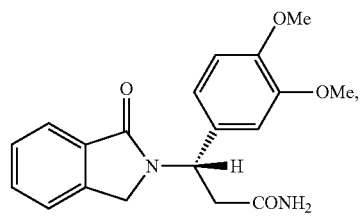 [SMILES: COc1ccc([C@H](CC(N)=O)N2Cc3ccccc3C2=O)cc1OC]

or a pharmaceutically acceptable salt, solvate, hydrate, stereoisomer or prodrug thereof.

In one embodiment, provided herein is a compound having the following structure:

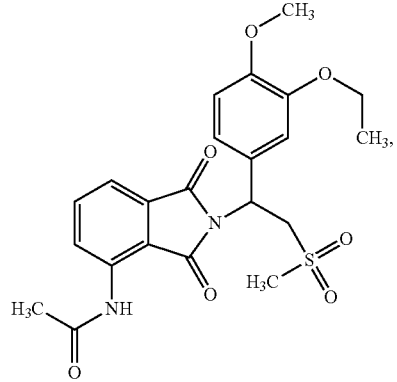 [SMILES: CCOc1cc(C(CS(C)(=O)=O)N2C(=O)c3cccc(NC(C)=O)c3C2=O)ccc1OC]

or a pharmaceutically acceptable salt, solvate, hydrate, stereoisomer or prodrug thereof. In another embodiment, the stereoisomers of the compound are also provided herein. In one embodiment, provided herein is a compound having the following structure:

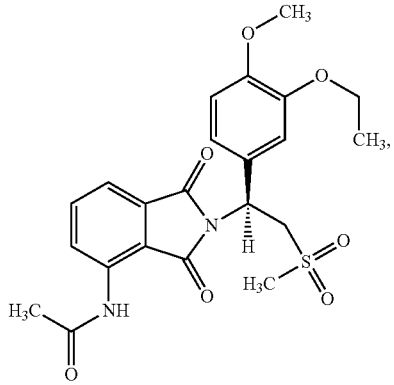

or a pharmaceutically acceptable salt, solvate, hydrate, stereoisomer or prodrug thereof. In one embodiment, provided herein is a compound having the following structure:

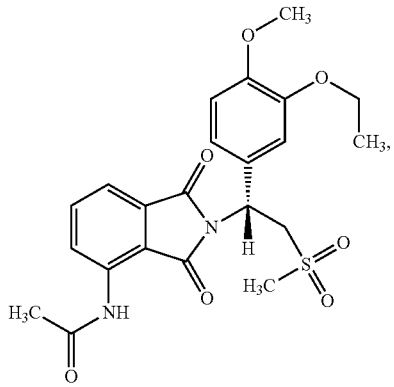

or a pharmaceutically acceptable salt, solvate, hydrate, stereoisomer or prodrug thereof.

In one embodiment, provided herein is a compound having the following structure:

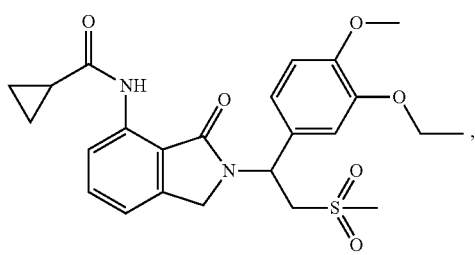 [SMILES: CCOc1cc(C(CS(C)(=O)=O)N2Cc3cccc(NC(=O)C4CC4)c3C2=O)ccc1OC]

or a pharmaceutically acceptable salt, solvate, hydrate, stereoisomer or prodrug thereof. In another embodiment, the stereoisomers of the compound are also provided herein. In one embodiment, provided herein is a compound having the following structure:

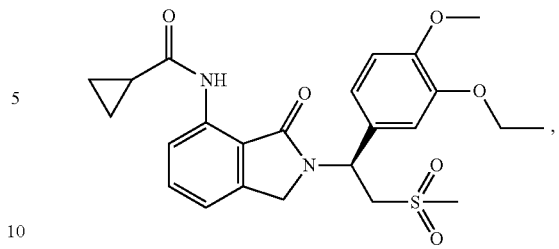

or a pharmaceutically acceptable salt, solvate, hydrate, stereoisomer or prodrug thereof. In one embodiment, provided herein is a compound having the following structure:

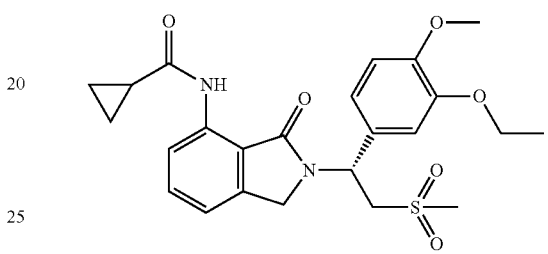

or a pharmaceutically acceptable salt, solvate, hydrate, stereoisomer or prodrug thereof.

In one embodiment, provided herein provided herein are immunomodulatory compounds, and pharmaceutically acceptable salts, solvates, hydrates, stereoisomers, and/or prodrugs thereof. In one embodiment, provided herein is the pharmaceutically acceptable salt, solvate, hydrate, stereoisomer, and prodrug of a compound provided herein.

As used herein and unless otherwise indicated, the term "immuno-modulatory compounds" encompasses certain small organic molecules that inhibit LPS induced monocyte TNF-α, IL-1β, IL-12, IL-6, MIP-1α, MCP-1, GM-CSF, G-CSF, and/or COX-2 production. Specific immunomodulatory compounds are discussed herein elsewhere.

In one embodiment, TNF-α is an inflammatory cytokine produced by macrophages and monocytes during acute inflammation. TNF-α is responsible for a diverse range of signaling events within cells. Without being limited by a particular theory, one of the biological effects exerted by the immunomodulatory compounds provided herein is the reduction of myeloid cell TNF-α production. Immunomodulatory compounds provided herein may enhance the degradation of TNF-α mRNA.

In one embodiment, without being limited by theory, immunomodulatory compounds provided herein may also be potent co-stimulators of T cells and increase cell proliferation dramatically in a dose dependent manner. In one embodiment, immunomodulatory compounds provided herein may also have a greater co-stimulatory effect on the CD8+ T cell subset than on the CD4+ T cell subset. In one embodiment, the compounds have anti-inflammatory properties against myeloid cell responses, yet efficiently co-stimulate T cells to produce greater amounts of IL-2, IFN-γ, and to enhance T cell proliferation and CD8+ T cell cytotoxic activity. In one embodiment, without being limited by a particular theory, immunomodulatory compounds provided herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

In one embodiment, specific examples of immunomodulatory compounds include, but are not limited to, cyano and carboxy derivatives of substituted styrenes such as those disclosed in U.S. Pat. No. 5,929,117; 1-oxo-2-(2,6-dioxo-3-fluoropiperidin-3-yl)isoindolines and 1,3-dioxo-2-(2,6-dioxo-3-fluoropiperidine-3-yl)isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl)isoindolines (e.g., 4-methyl derivatives of thalidomide), substituted 2-(2,6-dioxopiperidin-3-yl)phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. patent publication no. 2003/0096841 published on May 22, 2003, and International Application No. PCT/US01/50401 (International Publication No. WO 02/059106). The entireties of each of the patents and patent applications identified herein are incorporated herein by reference. In one embodiment, immunomodulatory compounds do not include thalidomide.

In one embodiment, various immunomodulatory compounds provided herein contain one or more chiral centers, and can exist as racemic mixtures of enantiomers or mixtures of diastereomers. Provided herein is the use of stereomerically pure forms of such compounds, as well as the use of mixtures of those forms. For example, mixtures comprising equal or unequal amounts of the enantiomers of a immunomodulatory compound provided herein may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In one embodiment, the immunomodulatory compounds provided herein include, but are not limited to, 1-oxo- and 1,3dioxo-2-(2,6-dioxopiperidin-3-yl)isoindolines substituted with amino in the benzo ring as described in U.S. Pat. No. 5,635,517 which is incorporated herein by reference. These compounds have the structure I:

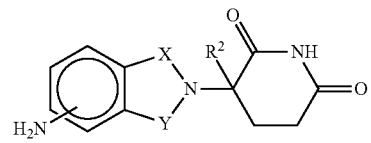

in which one of X and Y is C=O, the other of X and Y is C=O or $CH_2$, and $R^2$ is hydrogen or lower alkyl, in one embodiment, methyl.

In one embodiment, specific immunomodulatory compounds include, but are not limited to:

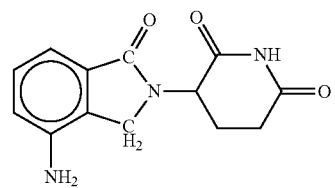

1-oxo-2-(2,6-dioxopiperidin-3-yl)-4-aminoisoindoline;

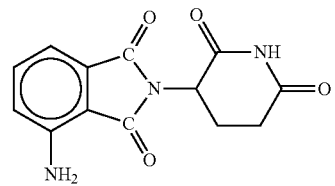

1,3-dioxo-2-(2,6-dioxopiperidin-3-yl)-4-aminoisoindoline; and

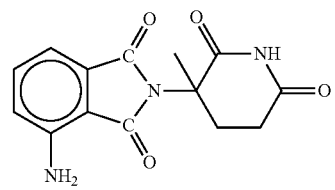

1,3-dioxo-2-(3-methyl-2,6-dioxopiperidin-3-yl)-4-aminoisoindole, and optically pure isomers thereof. The compounds can be obtained via standard, synthetic methods (see e.g., U.S. Pat. No. 5,635,517, incorporated herein by reference). The compounds are also available from Celgene Corporation, Warren, N.J.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, greater than about 90% by weight of one enantiomer of the compound and less than about 10% by weight of the other enantiomers of the compound, greater than about 95% by weight of one enantiomer of the compound and less than about 5% by weight of the other enantiomers of the compound, greater than about 97% by weight of one enantiomer of the compound and less than about 3% by weight of the other enantiomers of the compound, or greater than about 99% by weight of one enantiomer of the compound and less than about 1% by weight of the other enantiomers of the compound.

In one embodiment, other specific immunomodulatory compounds provided herein belong to a class of substituted 2-(2,6-dioxopiperidin-3-yl)phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. In one embodiment, representative compounds are of formula:

in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzyl, or halo;
provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

In one embodiment, compounds representative of this class are of the formulas:

wherein $R^1$ is hydrogen or methyl. In a separate embodiment, provided herein is the use of enantiomerically pure forms (e.g. optically pure (R) or (S) enantiomers) of these compounds.

In one embodiment, other specific immunomodulatory compounds provided herein belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. In one embodiment, representative compounds are of formula II:

wherein:
one of X and Y is C=O and the other is $CH_2$ or C=O;
$R^1$ is H, $(C_1$-$C_8)$alkyl, $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $C(O)R^3$, $C(S)R^3$, $C(O)OR^4$, $(C_1$-$C_8)$alkyl-$N(R^6)_2$, $(C_1$-$C_8)$alkyl-$OR^5$, $(C_1$-$C_8)$alkyl-$C(O)OR^5$, $C(O)NHR^3$, $C(S)NHR^3$, $C(O)NR^3R^{3'}$, $C(S)NR^3R^{3'}$ or $(C_1$-$C_8)$alkyl-$O(CO)R^5$;
$R^2$ is H, F, benzyl, $(C_1$-$C_8)$alkyl, $(C_2$-$C_8)$alkenyl, or $(C_2$-$C_8)$alkynyl;
$R^3$ and $R^{3'}$ are independently $(C_1$-$C_8)$alkyl, $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $(C_0$-$C_8)$alkyl-$N(R^6)_2$, $(C_1$-$C_8)$alkyl-$OR^5$, $(C_1$-$C_8)$alkyl-$C(O)OR^5$, $(C_1$-$C_8)$alkyl-$O(CO)R^5$, or $C(O)OR^5$;
$R^4$ is $(C_1$-$C_8)$alkyl, $(C_2$-$C_8)$alkenyl, $(C_2$-$C_8)$alkynyl, $(C_1$-$C_4)$alkyl-$OR^5$, benzyl, aryl, $(C_0$-$C_4)$alkyl-$(C_1$-$C_6)$heterocycloalkyl, or $(C_0$-$C_4)$alkyl-$(C_2$-$C_5)$heteroaryl;
$R^5$ is $(C_1$-$C_8)$alkyl, $(C_2$-$C_8)$alkenyl, $(C_2$-$C_8)$alkynyl, benzyl, aryl, or $(C_2$-$C_5)$heteroaryl;
each occurrence of $R^6$ is independently H, $(C_1$-$C_8)$alkyl, $(C_2$-$C_8)$alkenyl, $(C_2$-$C_8)$alkynyl, benzyl, aryl, $(C_2$-$C_5)$heteroaryl, or $(C_0$-$C_8)$alkyl-$C(O)O$—$R^5$ or the $R^6$ groups can join to form a heterocycloalkyl group;
n is 0 or 1; and
* represents a chiral-carbon center.

In one embodiment, provided herein are specific compounds of formula II, wherein when n is 0 then $R^1$ is $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $C(O)R^3$, $C(O)OR^4$, $(C_1$-$C_8)$alkyl-$N(R^6)_2$, $(C_1$-$C_8)$alkyl-$OR^5$, $(C_1$-$C_8)$alkyl-$C(O)OR^5$, $C(S)NHR^3$, or $(C_1$-$C_8)$alkyl-$O(CO)R^5$;
$R^2$ is H or $(C_1$-$C_8)$alkyl; and
$R^3$ is $(C_1$-$C_8)$alkyl, $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $(C_5$-$C_8)$alkyl-$N(R^6)_2$; $(C_0$-$C_8)$alkyl-$NH$—$C(O)O$—$R^5$; $(C_1$-$C_8)$alkyl-$OR^5$, $(C_1$-$C_8)$alkyl-$C(O)OR^5$, $(C_1$-$C_8)$alkyl-$O(CO)R^5$, or $C(O)OR^5$; and the other variables have the same definitions.

In one embodiment, provided herein are specific compounds of formula II, wherein $R^2$ is H or $(C_1$-$C_4)$alkyl.

In one embodiment, provided herein are specific compounds of formula II, wherein $R^1$ is $(C_1$-$C_8)$alkyl or benzyl.

In one embodiment, provided herein are specific compounds of formula II, wherein $R^1$ is H, $(C_1$-$C_8)$alkyl, benzyl, $CH_2OCH_3$, $CH_2CH_2OCH_3$, or

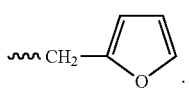

In one embodiment, provided herein are the compounds of formula II, wherein R¹ is

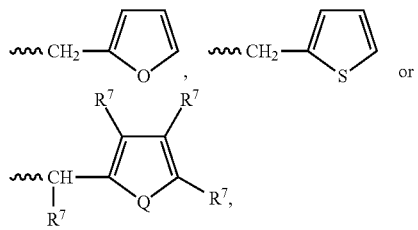

wherein Q is O or S, and each occurrence of R⁷ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of R⁷ can be taken together to form a bicyclic alkyl or aryl ring.

In one embodiment, provided herein are specific compounds of formula II, wherein R¹ is $C(O)R^3$.

In one embodiment, provided herein are specific compounds of formula II, wherein R³ is (C0-C4)alkyl-(C2-C5)heteroaryl, (C1-C8)alkyl, aryl, or (C0-C4)alkyl-$OR^5$.

In one embodiment, provided herein are specific compounds of formula II, wherein the heteroaryl is pyridyl, furyl, or thienyl.

In one embodiment, provided herein are specific compounds of formula II, wherein R¹ is $C(O)OR^4$.

In one embodiment, provided herein are specific compounds of formula II, wherein the H of C(O)NHC(O) can be replaced with $(C_1-C_4)$alkyl, aryl, or benzyl.

In one embodiment, further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

In one embodiment, other specific immunomodulatory compounds provided herein belong to a class of isoindole-imides disclosed in U.S. Patent Application Publication Nos. US 2002/0045643, International Publication No. WO 98/54170, and U.S. Pat. No. 6,395,754, each of which is incorporated herein by reference. In one embodiment, representative compounds are of formula III:

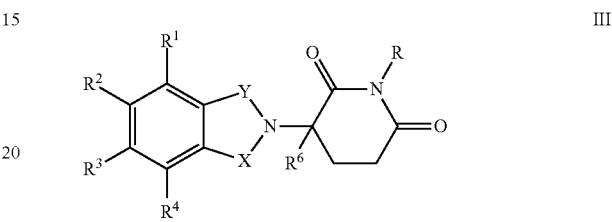

wherein:
one of X and Y is C=O and the other is $CH_2$ or C=O;
R is H or $CH_2OCOR'$;
(i) each of R¹, R², R³, or R⁴, independently of the others, is halo, alkyl of 1 to 4 carbon atoms, or alkoxy of 1 to 4 carbon atoms or (ii) one of R¹, R², R³, or R⁴ is nitro or —NHR⁵ and the remaining of R¹, R², R³, or R⁴ are hydrogen;
R⁵ is hydrogen or alkyl of 1 to 8 carbons
R⁶ hydrogen, alkyl of 1 to 8 carbon atoms, benzo, chloro, or fluoro;
R' is $R^7$—$CHR^{10}$—$N(R^8R^9)$;
R⁷ is m-phenylene or p-phenylene or —$(C_nH_{2n})$— in which n has is 0, 1, 2, 3, or 4;
each of R⁸ and R⁹ taken independently of the other is hydrogen or alkyl of 1 to 8 carbon atoms, or R⁸ and R⁹ taken together are tetramethylene, pentamethylene, hexamethylene, or —$CH_2CH_2X_1CH_2CH_2$— in which $X_1$ is —O—, —S—, or —NH—;
R¹⁰ is hydrogen, alkyl of to 8 carbon atoms, or phenyl; and
* represents a chiral-carbon center.

In one embodiment, other representative compounds are of formula:

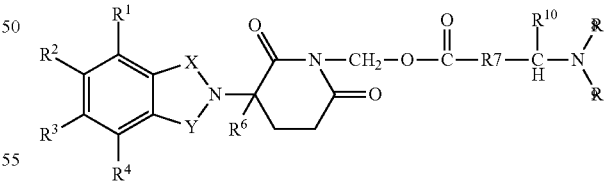

wherein:
one of X and Y is C=O and the other of X and Y is C=O or $CH_2$;
(i) each of R¹, R², R³, or R⁴, independently of the others, is halo, alkyl of 1 to 4 carbon atoms, or alkoxy of 1 to 4 carbon atoms or (ii) one of R¹, R², R³, and R⁴ is —NHR⁵ and the remaining of R¹, R², R³, and R⁴ are hydrogen;
R⁵ is hydrogen or alkyl of 1 to 8 carbon atoms;
R⁶ is hydrogen, alkyl of 1 to 8 carbon atoms, benzo, chloro, or fluoro;

$R^7$ is m-phenylene or p-phenylene or —$(C_nH_{2n})$— in which n is 0, 1, 2, 3, or 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—; and $R^{10}$ is hydrogen, alkyl of to 8 carbon atoms, or phenyl.

In one embodiment, other representative compounds are of formula:

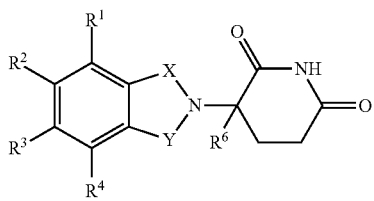

in which one of X and Y is C═O and the other of X and Y is C═O or $CH_2$;

each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and $R^6$ is hydrogen, alkyl of 1 to 8 carbon atoms, benzo, chloro, or fluoro.

In one embodiment, other representative compounds are of formula:

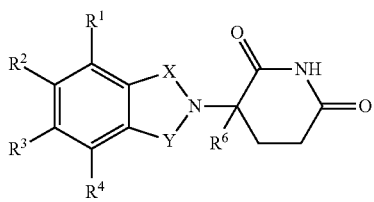

in which:

one of X and Y is C═O and the other of X and Y is C═O or $CH_2$;

(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen, alkyl of 1 to 8 carbon atoms, or CO—$R^7$—CH($R^{10}NR^8R^9$ in which each of $R^7$, $R^8$, $R^9$, and $R^{10}$ is as herein defined; and $R^6$ is alkyl of 1 to 8 carbon atoms, benzo, chloro, or fluoro.

In one embodiment, specific examples of the compounds are of formula:

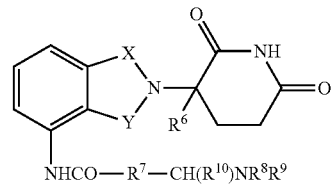

in which:

one of X and Y is C═O and the other of X and Y is C═O or $CH_2$;

$R^6$ is hydrogen, alkyl of 1 to 8 carbon atoms, benzyl, chloro, or fluoro;

$R^7$ is m-phenylene, p-phenylene or —$(C_nH_{2n})$— in which n is 0, 1, 2, 3, or 4; each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S— or —NH—; and $R^{10}$ is hydrogen, alkyl of 1 to 8 carbon atoms, or phenyl.

In one embodiment, other specific immunomodulatory compounds provided herein include, but are not limited to, 1-oxo-2-(2,6-dioxo-3-fluoropiperidin-3-yl isoindolines and 1,3-dioxo-2-(2,6-dioxo-3-fluoropiperidine-3-yl)isoindolines such as those described in U.S. Pat. Nos. 5,874,448 and 5,955,476, each of which is incorporated herein by reference. In one embodiment, representative compounds are of formula:

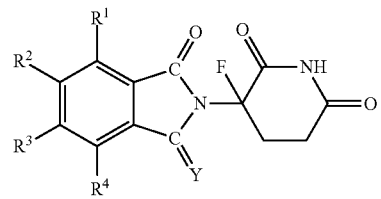

wherein:

Y is oxygen or $H^2$ and each of $R^1$, $R^2$, $R^3$, and $R^4$, independently of the others, is hydrogen, halo, alkyl of 1 to 4 carbon atoms, alkoxy of 1 to 4 carbon atoms, or amino.

In one embodiment, other specific immunomodulatory compounds provided herein include, but are not limited to, the tetra substituted 2-(2,6-dioxopiperidin-3-yl)-1-oxoisoindolines described in U.S. Pat. No. 5,798,368, which is incorporated herein by reference. In one embodiment, representative compounds are of formula:

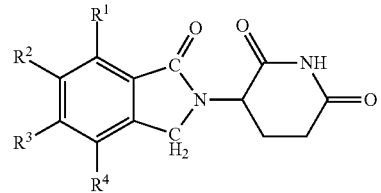

wherein each of $R^1$, $R^2$, $R^3$, and $R^4$, independently of the others, is halo, alkyl of 1 to 4 carbon atoms, or alkoxy of 1 to 4 carbon atoms.

In one embodiment, other specific immunomodulatory compounds provided herein include, but are not limited to, 1-oxo and 1,3-dioxo-2-(2,6-dioxopiperidin-3-yl)isoindolines disclosed in U.S. Pat. No. 6,403,613, which is incorporated herein by reference. In one embodiment, representative compounds are of formula:

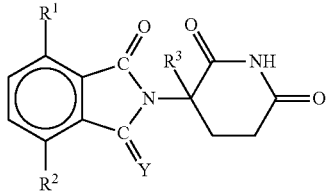

in which
Y is oxygen or H$_2$,
a first of R$^1$ and R$^2$ is halo, alkyl, alkoxy, alkylamino, dialkylamino, cyano, or carbamoyl, the second of R$^1$ and R$^2$, independently of the first, is hydrogen, halo, alkyl, alkoxy, alkylamino, dialkylamino, cyano, or carbamoyl, and
R$^3$ is hydrogen, alkyl, or benzyl.
In one embodiment, specific examples of the compounds are of formula:

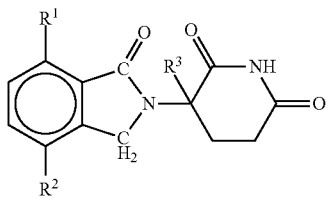

wherein
a first of R$^1$ and R$^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;
the second of R$^1$ and R$^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
R$^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.
In one embodiment, other representative compounds are of formula:

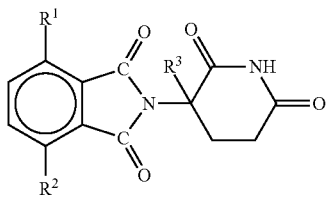

wherein:
a first of R$^1$ and R$^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;
the second of R$^1$ and R$^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
R$^3$ is hydrogen, alkyl of from 1 to 4 carbon atoms, or benzyl.

In one embodiment, other specific immunomodulatory compounds provided herein include, but are not limited to, 1-oxo and 1,3-dioxoisoindolines substituted in the 4- or 5-position of the indoline ring described in U.S. Pat. No. 6,380,239 and co-pending U.S. application Ser. No. 10/900,270, filed Jul. 28, 2004, which are incorporated herein by reference. In one embodiment, representative compounds are of formula:

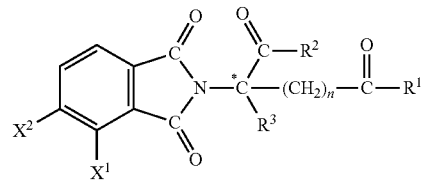

in which the carbon atom designated C* constitutes a center of chirality (when n is not zero and R$^1$ is not the same as R$^2$); one of X$^1$ and X$^2$ is amino, nitro, alkyl of one to six carbons, or NH—Z, and the other of X$^1$ or X$^2$ is hydrogen; each of R$^1$ and R$^2$ independent of the other, is hydroxy or NH—Z; R$^3$ is hydrogen, alkyl of one to six carbons, halo, or haloalkyl; Z is hydrogen, aryl, alkyl of one to six carbons, formyl, or acyl of one to six carbons; and n is 0, 1, or 2; provided that if X$^1$ is amino, and n is 1 or 2, then R$^1$ and R$^2$ are not both hydroxy; and the salts thereof.

In one embodiment, further representative compounds are of formula:

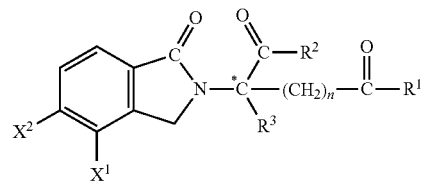

in which the carbon atom designated C* constitutes a center of chirality when n is not zero and R$^1$ is not R$^2$; one of X$^1$ and X$^2$ is amino, nitro, alkyl of one to six carbons, or NH—Z, and the other of X$^1$ or X$^2$ is hydrogen; each of R$^1$ and R$^2$ independent of the other, is hydroxy or NH—Z; R$^3$ is alkyl of one to six carbons, halo, or hydrogen; Z is hydrogen, aryl or an alkyl or acyl of one to six carbons; and n is 0, 1, or 2.

In one embodiment, specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-carbamoyl-butyric acid, which have the following structures, respectively, and pharmaceutically acceptable salts, solvates, hydrates, prodrugs, and stereoisomers thereof:

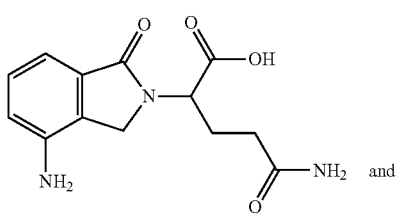

and

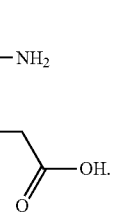

In one embodiment, other representative compounds are of formula:

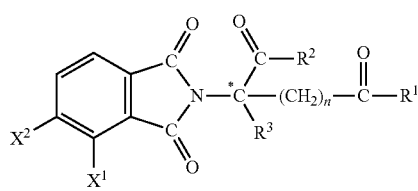

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n is 0, 1, or 2; and the salts thereof.

In one embodiment, specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvates, hydrates, prodrugs, and stereoisomers thereof:

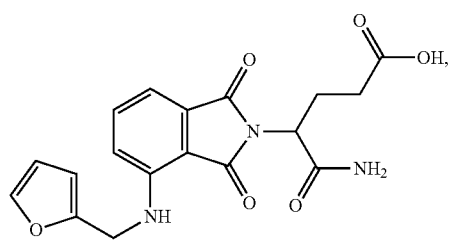

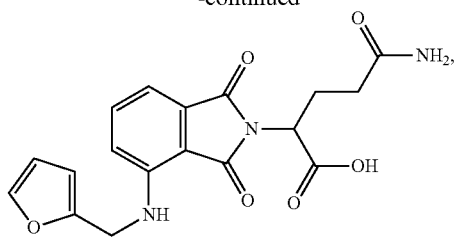

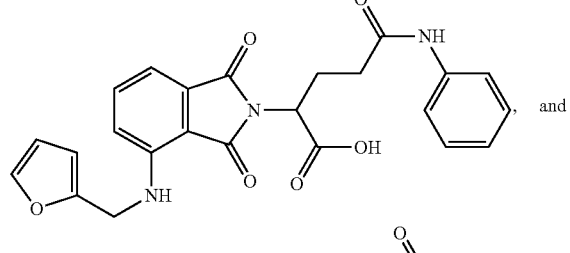

and

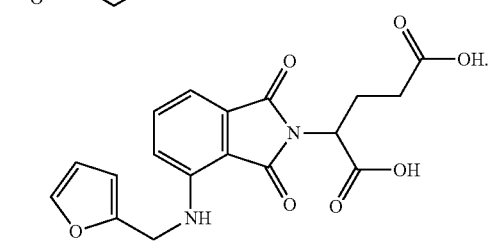

In one embodiment, other specific examples of the compounds are of formula:

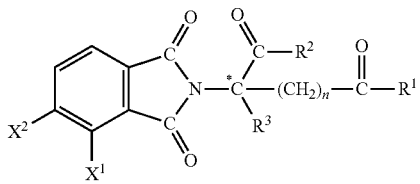

wherein:

one of $X^1$ and $X^2$ is nitro, or NH—Z, and the other of $X^1$ or $X^2$ is hydrogen;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n is 0, 1, or 2; and if —$COR^2$ and —$(CH_2)_nCOR^1$ are different, the carbon atom designated C* constitutes a center of chirality.

In one embodiment, other representative compounds are of formula:

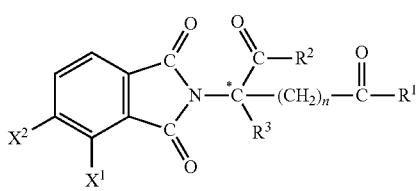

wherein:

one of $X^1$ and $X^2$ is alkyl of one to six carbons;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n is 0, 1, or 2; and if —$COR^2$ and —$(CH_2)_nCOR^1$ are different, the carbon atom designated C* constitutes a center of chirality.

In one embodiment, other specific immunomodulatory compounds provided herein include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. In one embodiment, representative compounds are of formula:

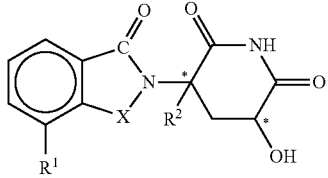

wherein:

the carbon atoms designated * constitute centers of chirality;

X is —C(O)— or —$CH_2$—;

$R^1$ is alkyl of 1 to 8 carbon atoms or —$NHR^3$;

$R^2$ is hydrogen, alkyl of 1 to 8 carbon atoms, or halogen; and $R^3$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which $R^4$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

In certain embodiments, the compound is:

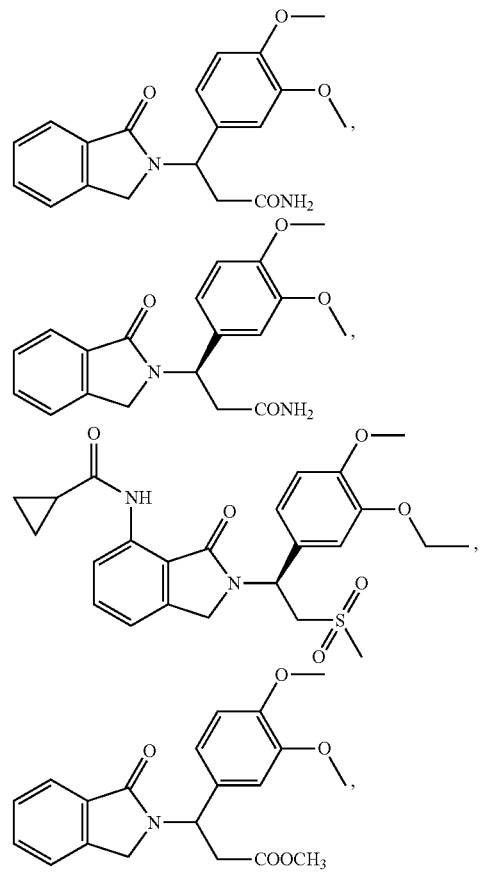

or a pharmaceutically acceptable salt, solvate or stereoisomer thereof.

In one embodiment, the compounds described herein can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

In one embodiment, the compounds used herein may be small organic molecules having a molecular weight less than about 1,000 g/mol, and are not proteins, peptides, oligonucleotides, oligosaccharides or other macromolecules.

In one embodiment, various PDE4 modulators or immunomodulatory compounds provided herein contain one or more chiral centers, and can exist as racemic mixtures of enantiomers or mixtures of diastereomers. In one embodiment, provided herein is the use of stereomerically pure forms of such compounds, as well as the use of mixtures of those forms. For example, mixtures comprising equal or unequal amounts of the enantiomers of PDE4 modulators or immunomodulatory compounds may be used in methods and compositions provided herein. The purified (R) or (S) enantiomers of the specific compounds disclosed herein may be used substantially free of its other enantiomer.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, e.g., Berge et al., *J. Pharm. Sci.* 1977, 66, 1-19; and *Handbook of Pharmaceutical Salts, Properties, and Use*, Stahl and Wermuth, ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, e.g., Harper, *Progress in Drug Research* 1962, 4, 221-294; Morozowich et al. in Design of Biopharmaceutical Properties through Prodrugs and Analogs, Roche ed., APHA Acad. Pharm. Sci. 1977; Bioreversible Carriers in Drug in Drug Design, Theory and Application, Roche ed., APHA Acad. Pharm. Sci. 1987; Design of Prodrugs, Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in Transport Processes in Pharmaceutical Systems, Amidon et al., ed., Marcell Dekker, 185-218, 2000; Balant et al., *Eur. J. Drug Metab. Pharmacokinet.* 1990, 15, 143-53; Balimane & Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. Pharmaceutical Compositions

In one embodiment, provided herein is a pharmaceutical composition for use in the modulation of immune responses to a respiratory viral infection in a subject. In one embodiment, provided herein is a single unit dosage form for use in the modulation of immune responses to a respiratory viral infection in a subject. In one embodiment, provided herein is a kit for use in the modulation of immune responses to a respiratory viral infection in a subject. In one embodiment, provided herein is a pharmaceutical composition, a single unit dosage form, or a kit for modulating immune responses to a respiratory viral infection in a subject.

In one embodiment, provided herein is a pharmaceutical composition for use in the treatment, prevention, amelioration, and/or delay of the onset of one or more symptoms associated with or resulting from a respiratory viral infection in a subject. In one embodiment, provided herein is a single unit dosage form for use in the treatment, prevention, amelioration, and/or delay of the onset of one or more symptoms associated with or resulting from a respiratory viral infection in a subject. In one embodiment, provided herein is a kit for use in the treatment, prevention, amelioration, and/or delay of the onset of one or more symptoms associated with or resulting from a respiratory viral infection in a subject. In one embodiment, provided herein is a pharmaceutical composition, a single unit dosage form, or a kit for treating, preventing, ameliorating, and/or delaying the onset of one or more symptoms associated with or resulting from a respiratory viral infection in a subject.

In one embodiment, the pharmaceutical composition provided herein comprise a compound provided herein, or a pharmaceutically acceptable salt, solvate, hydrate, stereoisomer, or prodrug thereof. In one embodiment, the single unit dosage form provided herein comprise a compound provided herein, or a pharmaceutically acceptable salt, solvate, hydrate, stereoisomer, or prodrug thereof. In one embodiment, the kit provided herein comprise a compound provided herein, or a pharmaceutically acceptable salt, solvate, hydrate, stereoisomer, or prodrug thereof.

In one embodiment, the pharmaceutical composition provided herein comprises a PDE4 modulator, or a pharmaceutically acceptable salt, solvate, hydrate, stereoisomer, or prodrug thereof. In one embodiment, the pharmaceutical composition provided herein comprises an immunomodulatory compound, or a pharmaceutically acceptable salt, solvate, hydrate, stereoisomer, or prodrug thereof. In one embodiment, the single unit dosage form provided herein comprises a PDE4 modulator, or a pharmaceutically acceptable salt, solvate, hydrate, stereoisomer, or prodrug thereof. In one embodiment, the single unit dosage form provided herein comprises an immunomodulatory compound, or a pharmaceutically acceptable salt, solvate, hydrate, stereoisomer, or prodrug thereof. In one embodiment, the kit provided herein comprises a PDE4 modulator, or a pharmaceutically acceptable salt, solvate, hydrate, stereoisomer, or prodrug thereof. In one embodiment, the kit provided herein comprises an immunomodulatory compound, or a pharmaceutically acceptable salt, solvate, hydrate, stereoisomer, or prodrug thereof.

In one embodiment, provided herein are pharmaceutical compositions, which comprise one or more compounds provided herein, or a pharmaceutically acceptable salt, solvate, hydrate, stereoisomer, or prodrug thereof, as an active ingredient, in combination with one or more pharmaceutically acceptable carrier. In one embodiment, the pharmaceutical composition comprises at least one nonrelease controlling excipient or carrier. In one embodiment, the pharmaceutical composition comprises at least one release controlling and at least one nonrelease controlling excipients or carriers.

In one embodiment, the pharmaceutical composition provided herein comprises an immunomodulatory compound, or a pharmaceutically acceptable salt, solvate, hydrate, stereoisomer, or prodrug thereof. In one embodiment, the single unit dosage form provided herein comprises an immunomodulatory compound, or a pharmaceutically acceptable salt, solvate, hydrate, stereoisomer, or prodrug thereof. In one embodiment, the kit provided herein comprises an immunomodulatory compound, or a pharmaceutically acceptable salt, solvate, hydrate, stereoisomer, or prodrug thereof.

In certain embodiments, the compound, or a pharmaceutically acceptable salt, solvate, hydrate, stereoisomer, or prodrug thereof, used in the pharmaceutical compositions provided herein is in a solid form. Suitable solid forms include, but are not limited to, solid forms comprising the free base of the compound, and solid forms comprising salts of the compound. In certain embodiments, solid forms provided herein include polymorphs, solvates (including hydrates), and cocrystals comprising the compound and/or salts thereof. In certain embodiments, the solid form is a crystal form of the compound, or a pharmaceutically acceptable salt or solvate thereof.

In one embodiment, the pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, e.g., Remington, *The Science and Practice of Pharmacy,* 21st Edition; Lippincott Williams & Wilkins: Philadelphia, Pa., 2005; *Modified-Release Drug Delivery Technology*, Rathbone et al., eds., Drugs and the Pharmaceutical Science, Marcel Dekker, Inc.: New York, N.Y., 2003; Vol. 126).

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration. In one embodiment, the pharmaceutical compositions are provided in a dosage form for intra-nasal administration. In one embodiment, the pharmaceutical compositions are provided in a dosage form as an inhalant.

In one embodiment, the pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In one embodiment, the pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

1. Oral Administration

In one embodiment, the pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

In one embodiment, binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

In one embodiment, suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

In one embodiment, suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

In one embodiment, suitable lubricants include, but are not limited to, calcium stearate; magnesium stearate; mineral oil; light mineral oil; glycerin; sorbitol; mannitol; glycols, such as glycerol behenate and polyethylene glycol (PEG) (e.g., PEG400 and PEG6000); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica (silicone dioxide) or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

In one embodiment, suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (e.g., TWEEN® 20), poloxamers (e.g., PLURONIC® F68), polyoxyethylene sorbitan monooleate 80 (e.g., TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, polyvinylpyrrolidone, and lauroyl polyoxylglycerides (e.g., GELUCIRE® 44/14). Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

In one embodiment, suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

It should be understood that many carriers and excipients may serve several functions, even within the same formulation.

In one embodiment, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. In one embodiment, enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. In one embodiment, film coating imparts the same general characteristics as sugar coating. Multiple compressed tablets are compressed tablets made by more than one compression cycle, including layered tablets, and press-coated or dry-coated tablets.

In one embodiment, the tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

In one embodiment, the pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In one embodiment, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

In one embodiment, other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

In one embodiment, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

In one embodiment, the pharmaceutical compositions provided herein may be formulated as immediate or modified release dosage forms, including delayed-, sustained, pulsed-, controlled, targeted-, and programmed-release forms.

In one embodiment, the pharmaceutical compositions provided herein may be co-formulated with other active ingredients which do not impair the desired therapeutic action, or with substances that supplement the desired action.

In one embodiment, active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

2. Parenteral Administration

In one embodiment, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In one embodiment, the pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington, *The Science and Practice of Pharmacy*, supra).

In one embodiment, the pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, the pharmaceutical compositions provided herein may be formulated for single or multiple dosage administration. The single dosage formulations are packaged in an ampoule, a vial, or a syringe. The multiple dosage parenteral formulations may contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein may be formulated as immediate or modified release dosage forms, including delayed-, sustained, pulsed-, controlled, targeted-, and programmed-release forms.

In one embodiment, the pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyloxyethanol copolymer, and ethylene/vinyl acetate/vinyl alcohol terpolymer.

3. Topical Administration

In one embodiment, the pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in, e.g., Remington, *The Science and Practice of Pharmacy*, supra.

In one embodiment, rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

In one embodiment, the pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

In one embodiment, solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

In one embodiment, the pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

In one embodiment, capsules, blisters and cartridges for use in an inhaler or insufflator may be formulated to contain a powder mix of the pharmaceutical compositions provided herein; a suitable powder base, such as lactose or starch; and a performance modifier, such as L-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

In one embodiment, the pharmaceutical compositions provided herein for topical administration may be formulated to be immediate release or modified release, including delayed-, sustained-, pulsed-, controlled-, targeted, and programmed release.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

In one embodiment, kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

D. Methods of Use

In one embodiment, provided herein is a method for modulating immune responses to a respiratory viral infection in a subject, comprising administering a compound provided herein, or pharmaceutically acceptable salt, solvate, hydrate, stereoisomer, and prodrug thereof. In one embodiment, provided herein is a method for treating, preventing, ameliorating, and/or delaying the onset of one or more symptoms associated with or resulting from a respiratory viral infection in a subject, comprising administering a compound provided herein, or pharmaceutically acceptable salt, solvate, hydrate, stereoisomer, and prodrug thereof. In one embodiment, provided herein is a method for treating one or more symptoms associated with or resulting from a respiratory viral infection in a subject, comprising administering a compound provided herein, or pharmaceutically acceptable salt, solvate, hydrate, stereoisomer, and prodrug thereof. In one embodiment, provided herein is a method for preventing one or more symptoms associated with or resulting from a respiratory viral infection in a subject, comprising administering a compound provided herein, or pharmaceutically acceptable salt, solvate, hydrate, stereoisomer, and prodrug thereof. In one embodiment, provided herein is a method for ameliorating one or more symptoms associated with or resulting from a respiratory viral infection in a subject, comprising administering a compound provided herein, or pharmaceutically acceptable salt, solvate, hydrate, stereoisomer, and prodrug thereof. In one embodiment, provided herein is a method for delaying the onset of one or more symptoms associated with or resulting from a respiratory viral infection in a subject, comprising administering a compound provided herein, or pharmaceutically acceptable salt, solvate, hydrate, stereoisomer, and prodrug thereof. In certain embodiments, the methods provided herein comprise co-administering two or more active agents. In certain embodiments, the methods provided herein comprise co-administering a compound provided herein, or pharmaceutically acceptable salt, solvate, hydrate, stereoisomer, and prodrug thereof, with an anti-viral vaccine. In certain embodiments, the methods provided herein comprise administering a compound provided herein, or pharmaceutically acceptable salt, solvate, hydrate, stereoisomer, and prodrug thereof, in a subject after the subject receives anti-viral vaccine for a respiratory viral infection. In certain embodiments, the methods provided herein comprise administering a compound provided herein, or pharmaceutically acceptable salt, solvate, hydrate, stereoisomer, and prodrug thereof, in a subject before the subject receives anti-viral vaccine for a respiratory viral infection. In certain embodiments, the subject is a mammal. In certain embodiments, the subject is a human.

In one embodiment, the respiratory viral infection includes, but is not limited to, influenza viral infection (e.g., seasonal flu), rhinovirus infection (e.g., common cold), coronavirus infection (e.g., Severe Acute Respiratory Syndrome and common cold), and/or paramyxovirus infection (e.g., measles). In one embodiment, the respiratory viral infection is an influenza viral infection (e.g., seasonal flu), including but not limited to, Influenza A, Influenza B, and Influenza C viral infections. In one embodiment, the respiratory viral infection is In one embodiment, the respiratory viral infection is a rhinovirus infection (e.g., common cold), including various serotypes of rhinovirus. In one embodiment, the respiratory viral infection is a coronavirus infection (e.g., Severe Acute Respiratory Syndrome and common cold), including various types of coronavirus. In one embodiment, the respiratory viral infection is a paramyxovirus infection (e.g., measles), including various types of paramyxovirus (e.g., measles virus).

In one embodiment, the respiratory viral infection is the infection by a certain subtype of Influenza A virus. In one embodiment, the respiratory viral infection is the infection by a certain subtype of Influenza B virus. In one embodiment, the respiratory viral infection is the infection by a certain subtype of Influenza C virus. In one embodiment, the respiratory viral infection is the infection by a certain serotype of rhinovirus. In one embodiment, the respiratory viral infection is the infection by a certain type of coronavirus. In one embodiment, the respiratory viral infection is the infection by a certain type of paramyxovirus.

In one embodiment, the symptoms associated with or resulting from the respiratory viral infection provided herein include, but are not limited to, fever (in one embodiment, high fever), chills, sweating, headache, fatigue (in one embodiment, extreme fatigue), tiredness (in one embodiment, extreme tiredness), exhaustion (in one embodiment, extreme exhaustion), cough (in one embodiment, dry cough; in one embodiment, cough with mucus), runny nose, stuffy nose, sneezing, sore throat, body aches, muscle aches, joint pains, sinus pains, ear aches, chest pains, chest discomfort, sinus congestion, diarrhea, vomiting, abdominal pains, dehydration, shortness of breath, and/or any of the symptoms provided herein elsewhere. In one embodiment, the symptoms associated with or resulting from the respiratory viral infection provided herein relate to complications caused by the primary viral infections, such as, e.g., pneumonia (viral or bacterial), asthma, bronchitis, ear infection, sinus infection (sinusitis), muscle inflammation (myositis), infection of the central nervous system, pericarditis, dehydration, congestive heart failure, worsening of diabetes, and/or any of the complications provided herein elsewhere.

In one embodiment, provided herein is a method for treating, preventing, ameliorating, and/or delaying the onset of one or more symptoms associated with or resulting from an Influenza A viral infection in a subject, comprising administering a compound provided herein, or pharmaceutically acceptable salt, solvate, hydrate, stereoisomer, and prodrug thereof. In one embodiment, provided herein is a method for treating, preventing, ameliorating, and/or delaying the onset of one or more symptoms associated with or resulting from viral infection by one or more subtype(s) of Influenza A virus, comprising administering a compound provided herein, or pharmaceutically acceptable salt, solvate, hydrate, stereoisomer, and prodrug thereof. In one embodiment, the subtype of Influenza A virus includes, but is not limited to, H1N1, H2N2, H3N2, H5N1, H7N7, H1N2, H9N2, H7N2, H7N3, and H10N7 subtypes. In one embodiment, the subtype of Influenza A virus includes, but is not limited to, all combinations of H1 to H16 and N1 to N9 subtypes. In one embodiment, the subtype of Influenza A virus includes, but is not limited to, a new strain of Influenza A virus derived from, for example, viral mutation, antigenic shift, antigenic drift, and/or viral reassortment.

In one embodiment, provided herein is a method for treating, preventing, ameliorating, and/or delaying the onset of one or more symptoms associated with or resulting from an Influenza B viral infection in a subject, comprising administering a compound provided herein, or pharmaceutically acceptable salt, solvate, hydrate, stereoisomer, and prodrug thereof. In one embodiment, provided herein is a method for treating, preventing, ameliorating, and/or delaying the onset of one or more symptoms associated with or resulting from viral infection by one or more subtype(s) of Influenza B virus, comprising administering a compound provided herein, or pharmaceutically acceptable salt, solvate, hydrate, stereoisomer, and prodrug thereof. In one embodiment, the subtype of Influenza B virus includes, but is not limited to, Hong Kong/330/2001.

In one embodiment, provided herein is a method for treating, preventing, ameliorating, and/or delaying the onset of one or more symptoms associated with or resulting from an Influenza C viral infection in a subject, comprising administering a compound provided herein, or pharmaceutically acceptable salt, solvate, hydrate, stereoisomer, and prodrug thereof. In one embodiment, provided herein is a method for treating, preventing, ameliorating, and/or delaying the onset of one or more symptoms associated with or resulting from viral infection by one or more subtype(s) of Influenza C virus, comprising administering a compound provided herein, or pharmaceutically acceptable salt, solvate, hydrate, stereoisomer, and prodrug thereof. In one embodiment, the subtype of Influenza A virus includes, but is not limited to, California/78.

In one embodiment, provided herein is a method for treating, preventing, ameliorating, and/or delaying the onset of one or more symptoms associated with or resulting from the primary infection of a respiratory viral infection in a subject, comprising administering a compound provided herein, or pharmaceutically acceptable salt, solvate, hydrate, stereoisomer, and prodrug thereof. In one embodiment, provided herein is a method for treating, preventing, ameliorating, and/or delaying the onset of one or more symptoms associated with or resulting from the secondary infection of a respiratory viral infection in a subject, comprising administering a compound provided herein, or pharmaceutically acceptable salt, solvate, hydrate, stereoisomer, and prodrug thereof. In one embodiment, the secondary infection is caused by a virus of the same type as the virus causing the primary infection. In one embodiment, the secondary infection is caused by a virus of a different type as the virus causing the primary infection. In one embodiment, the secondary infection is a bacterial infection. In one embodiment, the secondary infection is a fungal infection. In one embodiment, the symptom associated with or resulting from the respiratory viral infection includes, but is not limited to, one or more symptoms associated with the viral infection, and one or more symptoms associated with complications resulting from the viral infection.

In one embodiment, provided herein is a method for treating, preventing, ameliorating, and/or delaying the onset of one or more symptoms associated with or resulting from a respiratory viral infection in a subject, comprising administering a compound provided herein, or pharmaceutically acceptable salt, solvate, hydrate, stereoisomer, and prodrug thereof, within one, two, three, four, five, six, seven, eight, nine, ten, eleven, twelve, thirteen, fourteen, fifteen, sixteen, seventeen, eighteen, nineteen, twenty, or greater than twenty days from the initial onset or diagnosis of the viral infection. In one embodiment, provided herein is a method for treating, preventing, ameliorating, and/or delaying the onset of one or more symptoms associated with or resulting from a respiratory viral infection in a subject, comprising administering a compound provided herein, or pharmaceutically acceptable salt, solvate, hydrate, stereoisomer, and prodrug thereof, prior to the appearance of the initial symptom of or diagnosis of viral infection. In one embodiment, provided herein is a method for treating, preventing, ameliorating, and/or delaying the onset of one or more symptoms associated with or resulting from a respiratory viral infection in a subject, comprising administering a compound provided herein, or pharmaceutically acceptable salt, solvate, hydrate, stereoisomer, and prodrug thereof, wherein the subject belongs to a high-risk sub-population, including but not limited to, young children, school-age children, pregnant women, smokers, the elderly, the immuno-compromised (e.g., HIV patients or transplant patient), the chronically ill (e.g., those diagnosed with or suffering from chronic obstructive pulmonary disease, asthma, bronchitis, or emphysema, among others), and/or healthcare workers (e.g., doctors and nurses). For example, respiratory viral infection, such as influenza, rhinovirus, coronavirus, and/or paramyxovirus infection, may cause complications, such as pneumonia, bronchitis, sinus or ear infection, coronary heart disease, congestive heart failure, or Guillain-Barre syndrome, in certain patient groups. In one embodiment, the methods provided herein treat, prevent, ameliorate, and/or delay the onset of one or more symptoms associated with the complications caused by or associated with a respiratory viral infection. In one embodiment, the methods provided herein treat, prevent, ameliorate, and/or delay the onset of one or more symptoms associated with or resulting from a respiratory viral infection in a subject, wherein the subject is over 50-year-old or less than 5-year-old. In one embodiment, the methods provided herein treat, prevent, ameliorate, and/or delay the onset of one or more symptoms associated with or resulting from a respiratory viral infection in a subject, wherein the subject has one or more chronic medical conditions and is more likely to develop complications as a result of the respiratory viral infection.

In one embodiment, the method provided herein comprises administering a compound provided herein, or a pharmaceutically acceptable salt, solvate, hydrate, and/or stereoisomer thereof. In one embodiment, the method provided herein comprises administering a pharmaceutical composition provided herein, comprising a compound provided herein, or a pharmaceutically acceptable salt, solvate, hydrate, and/or stereoisomer thereof. In one embodiment, the method provided herein comprises administering a therapeutically effect amount of a compound provided herein, or a pharmaceutically acceptable salt, solvate, hydrate, and/or stereoisomer thereof. In one embodiment, the method provided herein comprises administering a prophylactically effect amount of a compound provided herein, or a pharmaceutically acceptable salt, solvate, hydrate, and/or stereoisomer thereof.

In one embodiment, the method provided herein comprises administering a PDE4 modulator, or a pharmaceutically acceptable salt, solvate, hydrate, stereoisomer, or prodrug thereof. In one embodiment, the method provided herein comprises administering an immunomodulatory compound, or a pharmaceutically acceptable salt, solvate, hydrate, stereoisomer, or prodrug thereof.

In one embodiment, provided herein is the use of one or more PDE4 modulators in combination with other therapeutics presently used to treat, prevent, ameliorate, and/or delay the onset of one or more symptoms associated with or resulting from a respiratory viral infection in a subject. In another embodiment, provided herein is the use of one or more PDE4 modulators in combination with conventional therapies used to treat, prevent, ameliorate, and/or delay the onset of one or more symptoms associated with or resulting from a respiratory viral infection in a subject.

In one embodiment, the method provided herein comprises administering an immunomodulatory compound, or a pharmaceutically acceptable salt, solvate, hydrate, stereoisomer, or prodrug thereof. In one embodiment, provided herein is the use of one or more immuno-modulatory compound in combination with other therapeutics presently used to treat, prevent, ameliorate, and/or delay the onset of one or more symptoms associated with or resulting from a respiratory viral infection in a subject. In another embodiment, provided herein is the use of one or more immunomodulatory compounds in combination with conventional therapies used to treat, prevent, ameliorate, and/or delay the onset of one or more symptoms associated with or resulting from a respiratory viral infection in a subject.

In one embodiment, the methods provided herein comprise administration of a compound provided herein, or a pharmaceutically acceptable salt, solvate, hydrate, stereoisomer, or prodrug thereof, by, e.g., oral, intranasal (IN), intravenous (IV), and/or subcutaneous (SC) routes of administration. In one embodiment, the methods provided herein comprise co-administration of a compound provided herein, or a pharmaceutically acceptable salt, solvate, hydrate, stereoisomer, or prodrug thereof, with one or more additional active agents to provide a synergistic therapeutic effect in subjects in need thereof. In one embodiment, the co-administered agent(s) may be an agent to treat one or more symptoms of the respiratory viral infection. In one embodiment, the co-administered agent(s) may be an anti-viral vaccine of a respiratory viral infection. In certain embodiments, the co-administered agent(s) may be dosed, e.g., orally, intranasally, intravenously, and/or subcutaneously.

In certain embodiments, the methods provided herein comprise administering a combination of two or more active agents, wherein at least one of the active agents is a PDE4 modulator or an immunomodulatory compound provided herein elsewhere.

In one embodiment, the second active agent includes, but is not limited to, an anti-viral compound (e.g., Tamiflu® and Relenza®), an antibiotics (e.g., antibiotics used to treat or prevent bacterial pneumonitis), a decongestant, an antihistamine, a pain reliever, a fever reducer, and/or a cough suppressant. For available therapies, see, e.g., http://www.fda.gov/, The Merck Manual, 18th Ed. 2006, and PDR: Physician Desk Reference 2010, 64th Ed. 2009; the contents of each of which are hereby incorporated by reference in their entireties.

In certain embodiments, the methods provided herein comprise administering a PDE4 modulator or an immunomodulatory compound in conjunction with an anti-viral vaccine.

In one embodiment, the methods provided herein optionally comprise the step of identifying in a subject the presence of a certain type, subtype or strain of respiratory virus, including but not limited to, the types, subtypes, or strains of a respiratory virus provided herein elsewhere. In one embodiment, the methods provided herein comprise the step of administering a compound provided herein, or a pharmaceutically acceptable salt, solvate, hydrate, stereoisomer, or prodrug thereof, in a subject having a certain type, subtype, or strain of a respiratory virus, after the diagnosis of the viral infection.

In one embodiment, the $EC_{50}$ of the compound provided herein against a certain type of respiratory virus is less than 0.001 µM, about 0.001 µM, about 0.005 µM, about 0.01 µM, about 0.05 µM, about 0.1 µM, about 0.2 µM, about 0.3 µM, about 0.4 µM, about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM, about 10 µM, or greater than 10 µM.

In one embodiment, provided herein are methods comprising the step of contacting a compound provided herein, or a pharmaceutically acceptable salt, solvate, hydrate, stereoisomer, or prodrug thereof, with one or more cells infected with a respiratory virus, e.g., a certain type, subtype, or strain of a respiratory virus provided herein elsewhere. In certain embodiments, the methods may be conducted in vivo, in vitro, and/or ex vivo, e.g., as a cell based assay or an animal model. In certain embodiments, the methods may be conducted in an animal, e.g., mouse or rat. In certain embodiments, the methods further comprise the step of infecting an animal (e.g., mouse or rat) with a certain type, subtype, or strain of a respiratory virus, using a method known in the art, followed by the step of treating the animal with one or more compounds provided herein. In certain embodiments, the methods further comprise the step of infecting an animal (e.g., mouse or rat) with a certain type, subtype, or strain of a respiratory virus, using a method known in the art, subsequent to the step of treating the animal with one or more compounds provided herein. The time and sequence between the infection step and the treatment step may vary.

In one embodiment, provided herein is a murine model of respiratory viral infection (e.g., influenza infection) that can be used to assess potential treatments for the respiratory viral infection (e.g., influenza infection). In one embodiment, provided herein is a mouse model of respiratory viral infection (e.g., influenza infection) that can be used to assess potential treatments for the respiratory viral infection (e.g., influenza infection). In one embodiment, the murine model or the mouse model can be used to assess potential treatments for a pandemic H5N1 viral infection.

In one embodiment, standard laboratory mice or other sensitive species such as Ferrets are infected with a respiratory virus (e.g., a certain type, subtype or strain of influenza A, influenza B, or influenza C virus) by intranasal or aerosol administration, culminating in virus entry into respiratory epithelial cells and alveolar macrophages. In one embodiment, the viral strain is mouse-adapted. In one embodiment, the viral strain is not mouse-adapted. In one embodiment, the viral strains (e.g., either mouse-adapted or not mouse-adapted) can induce a toxic pneumonitis that can be reduced by early treatment with antivirals, such as, e.g., amantidine and ribavirin. In one embodiment, the virus (e.g., influenza virus) is readily recovered from the lungs and the infection follows a similar kinetics of infection in humans. In one embodiment, virus titers in the lungs peak from about 4 to about 6 days after infection and then decline. In one embodiment, the virus cannot be recovered by plaque assay at about day 14. In one embodiment, the symptoms of the disease, similar to the symptoms in humans, are dependent on the viral strain (e.g., the influenza strain) and the dose of virus administered.

In one embodiment, without being limited by a particular theory, during the first 3 days of the respiratory viral infection, infected epithelial cells and macrophages produce type-I IFN and TNFα, respectively. In one embodiment, without being limited by a particular theory, NK cells, in addition to their cytotoxic function, contribute to the cytokine milieu releasing IFNγ, TNFα and GM-CSF, all of which activate APCs. In one embodiment, without being limited by a particular theory, this innate phase of the immune response contributes to the magnitude of subsequent T and B cell accumulation. In one embodiment, without being limited by a particular theory, neutrophils are also prominent, and their numbers reflect the virulence and dose of virus. In one embodiment, without being limited by a particular theory, the cytokines produced in the murine model (e.g., a mouse model) replicate those observed during infection of humans. In one embodiment, without being limited by a particular theory, the composition of cells infiltrating the lung in the murine model (e.g., a mouse model) replicate those observed during infection of humans. In one embodiment, without being limited by a particular theory, the disease parameters in the murine model (e.g., a mouse model) replicate those observed during infection of humans. In one embodiment, without being limited by a particular theory, multiple disease parameters are measurable in the murine model (e.g., a mouse model) of infection, wherein the parameters include, but are not limited to, mean time to death, arterial oxygen saturation, pulmonary gas exchange, lung score, lung weight, host change in weight, host change in temperature, lung virus titer, histological consolidation score, and infiltrating cellular phenotype and function.

In one embodiment, without being limited by a particular theory, the murine model (e.g., mouse model) of the respiratory viral infection (e.g., seasonal influenza virus infection) is used to dissect correlations of protection and pathology. In one embodiment, for example, mice of about 6 to about 10 weeks of age are infected intranasally with an influenza virus while under inhaled anesthetic with 50 µL PBS (phosphate buffered saline) containing up to about 50 HA units of the virus. In one embodiment, without being limited by a particular theory, the administration of up to about 50 HA units of the virus ensures exposure of the lower airways with the viral inoculates, with minimal and infrequent viral entry into the gastrointestinal tract. In one embodiment, without being limited by a particular theory, the dose of the virus administered determines the pathological outcome. For example, in one embodiment, about 50 HA units of strain X31 (H3N2) induces rapid weight loss, maximal at about day 5, with recovery by about day 7 to about day 9 depending on the viral dose. In one embodiment, without being limited by a particular theory, higher doses of virus may lead to mortality in the murine model. In one embodiment, the APR8 strain (H1N1) is more virulent than strain X31 (H3N2), causing mortality at lower doses.

In one embodiment, without being limited by a particular theory, the administration of a compound provided herein in a subject having respiratory viral infection results in a reduction in weight loss as compared to that in an untreated subject.

In one embodiment, without being limited by a particular theory, the administration of a compound provided herein in a subject having respiratory viral infection modulates the production, function or receptor binding of chemotactic factors. In one embodiment, without being limited by a particular theory, the administration of a compound provided herein in a subject having respiratory viral infection facilitate the recruitment of early immune cells to the airspace, but not the lung. In one embodiment, without being limited by a particular theory, the administration of a compound provided herein in a subject having respiratory viral infection results in reduced early detrimental effect of the immune cells. In one embodiment, without being limited by a particular theory, the administration of a compound provided herein in a subject having respiratory viral infection modulates the effects of toxic products produced by the immune cells. In one embodiment, without being limited by a particular theory, the administration of a compound provided herein in a subject having respiratory viral infection modulates the respiratory burst and propagation of the immune cells (e.g., neutrophiles).

Reactive oxygen intermediates and nitrogen species contribute to influenza induced pathology. In one embodiment, without being limited by a particular theory, the administration of a compound provided herein in a subject having respiratory viral infection results in a reduced inflammatory microenvironment, resulting in, for example, less weight loss and reduced lung damage.

In one embodiment, without being limited by a particular theory, the administration of a compound provided herein in a subject having respiratory viral infection does not affect adaptive immunity. In one embodiment, without being limited by a particular theory, the administration of a compound provided herein in a subject having respiratory viral infection results in a decreased viral load. In one embodiment, without being limited by a particular theory, the administration of a compound provided herein in a subject having respiratory viral infection reduces peak viral load. In one embodiment, without being limited by a particular theory, the administration of a compound provided herein in a subject having respiratory viral infection results in a reduced inflammatory environment at an early time point. In one embodiment, without being limited by a particular theory, the administration of a compound provided herein in a subject having respiratory viral infection results in reduced T-cell recruitment in the airway. In one embodiment, without being limited by a particular theory, the administration of a compound provided herein in a subject having respiratory viral infection results in reduced neutrophils in the airway. In one embodiment, the reduction in cell numbers in the airway occurs at an early time point after viral infection.

In one embodiment, without being limited by a particular theory, the administration of a compound provided herein activates beta interferon. In one embodiment, without being limited by a particular theory, the administration of a compound provided herein modulates the RIG-1-like receptor pathway. In one embodiment, without being limited by a particular theory, the administration of a compound provided herein modulates the activity of the RIG-1-like receptor pathway. In one embodiment, without being limited by a particular theory, the administration of a compound provided herein modulates the activity of RIG-1-like receptors. In one embodiment, without being limited by a particular theory, the administration of a compound provided herein activates the activity of RIG-1-like receptors.

In certain embodiments, the subject to be treated with one of the methods provided herein has not been treated with other therapy prior to the administration of the compound provided herein, or a pharmaceutically acceptable salt, solvate, hydrate, stereoisomer, or prodrug thereof. In certain embodiments, the subject to be treated with one of the methods provided herein has been treated with one or more therapies (e.g., antiviral medication or over-the-counter medication) prior to the administration of the compound provided herein, or a pharmaceutically acceptable salt, solvate, hydrate, stereoisomer, or prodrug thereof. In one embodiment, the subject to be treated with one of the methods provided herein is infected with a type, subtype, or strain of a respiratory virus that is resistant to certain antiviral therapy.

In one embodiment, the methods provided herein encompass treating a subject regardless of patient's age, although some diseases or disorders are more common or severe in certain age groups. Further provided herein is a method for treating a hospitalized subject. Further provided herein is a method for treating a subject who has not been hospitalized. Because the subjects with a respiratory viral infection may have heterogeneous clinical manifestations and varying clinical outcomes, the treatment given to a particular subject may vary, depending on his/her physical condition, disease progression, among others. The skilled clinician will be able to readily determine, without undue experimentation, specific dosing regimens, secondary agents, and types of non-drug based standard therapy that can be effectively used to treat an individual subject with a respiratory viral infection.

In each embodiment provided herein, the method may further comprise one or more diagnostic steps, to determine, e.g., the type, subtype, or strain of the respiratory virus, and/or the symptoms and severity of the infection.

In each embodiment provided herein, the method may further comprise one or more disease evaluation steps, after the subject receives one or more doses of the compound provided herein, to determine, e.g., changes in the physical condition and prognosis of the subject.

In one embodiment, the methods provided herein comprise administering a compound provided herein, or a pharmaceutically acceptable salt, solvate, hydrate, stereoisomer, or prodrug thereof, by, e.g., intravenous (IV), subcutaneous (SC) or oral routes administration. Certain embodiments herein provide co-administration of a compound provided herein, or a pharmaceutically acceptable salt, solvate, hydrate, stereoisomer, or prodrug thereof, with one or more additional active agents to provide a synergistic therapeutic effect in subjects in need thereof. In certain embodiments, the co-administered agent(s) may be dosed, e.g., orally or by injection (e.g., IV or SC).

In one embodiment, the methods provided herein comprise administering a compound provided herein, or a pharmaceutically acceptable salt, solvate, hydrate, stereoisomer, or prodrug thereof, using, e.g., IV, SC and/or oral administration methods. In certain embodiments, the treatment cycles comprise multiple doses administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, or greater than 14 days). Suitable dosage amounts for the methods provided herein include, e.g., therapeutically effective amounts and prophylactically effective amounts. For example, in certain embodiments, the amount of the compound administered in the methods provided herein may range, e.g., between about 50 mg/m$^2$/day and about 2,000 mg/m$^2$/day, between about 100 mg/m$^2$/day and about 1,000 mg/m$^2$/day, between about 100 mg/m$^2$/day and about 500 mg/m$^2$/day, or between about 120 mg/m$^2$/day and about 250 mg/m$^2$/day. In certain embodiments, particular dosages are, e.g., about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day. In certain embodiments, particular dosages are, e.g., up to about 120 mg/m$^2$/day, up to about 140 mg/m$^2$/day, up to about 150 mg/m$^2$/day, up to about 180 mg/m$^2$/day, up to about 200 mg/m$^2$/day, up to about 220 mg/m$^2$/day, up to about 240 mg/m$^2$/day, up to about 250 mg/m$^2$/day, up to about 260 mg/m$^2$/day, up to about 280 mg/m$^2$/day, up to about 300 mg/m$^2$/day, up to about 320 mg/m$^2$/day, up to about 350 mg/m$^2$/day, up to about 380 mg/m$^2$/day, up to about 400 mg/m$^2$/day, up to about 450 mg/m$^2$/day, up to about 500 mg/m$^2$/day, up to about 750 mg/m$^2$/day, or up to about 1000 mg/m$^2$/day.

In one embodiment, the amount of the compound administered in the methods provided herein may range, e.g., between about 5 mg/day and about 2,000 mg/day, between about 10 mg/day and about 2,000 mg/day, between about 20 mg/day and about 2,000 mg/day, between about 50 mg/day and about 1,000 mg/day, between about 100 mg/day and about 500 mg/day, between about 150 mg/day and about 500 mg/day, or between about 150 mg/day and about 250 mg/day. In certain embodiments, particular dosages are, e.g., about 10 mg/day, about 20 mg/day, about 50 mg/day, about 75 mg/day, about 100 mg/day, about 120 mg/day, about 150 mg/day, about 200 mg/day, about 250 mg/day, about 300 mg/day, about 350 mg/day, about 400 mg/day, about 450 mg/day, about 500 mg/day, about 600 mg/day, about 700 mg/day, about 800 mg/day, about 900 mg/day, about 1,000 mg/day, about 1,200 mg/day, or about 1,500 mg/day. In certain embodiments, particular dosages are, e.g., up to about 10 mg/day, up to about 20 mg/day, up to about 50 mg/day, up to about 75 mg/day, up to about 100 mg/day, up to about 120 mg/day, up to about 150 mg/day, up to about 200 mg/day, up to about 250 mg/day, up to about 300 mg/day, up to about 350 mg/day, up to about 400 mg/day, up to about 450 mg/day, up to about 500 mg/day, up to about 600 mg/day, up to about 700 mg/day, up to about 800 mg/day, up to about 900 mg/day, up to about 1,000 mg/day, up to about 1,200 mg/day, or up to about 1,500 mg/day.

In one embodiment, the amount of the compound in the pharmaceutical composition or dosage form provided herein may range, e.g., between about 5 mg and about 2,000 mg, between about 10 mg and about 2,000 mg, between about 20 mg and about 2,000 mg, between about 50 mg and about 1,000 mg, between about 100 mg and about 500 mg, between about 150 mg and about 500 mg, or between about 150 mg and about 250 mg. In certain embodiments, particular amounts are, e.g., about 10 mg, about 20 mg, about 50 mg, about 75 mg, about 100 mg, about 120 mg, about 150 mg, about 200 mg, about 250 mg, about 300 mg, about 350 mg, about 400 mg, about 450 mg, about 500 mg, about 600 mg, about 700 mg, about 800 mg, about 900 mg, about 1,000 mg, about 1,200 mg, or about 1,500 mg. In certain embodiments, particular amounts are, e.g., up to about 10 mg, up to about 20 mg, up to about 50 mg, up to about 75 mg, up to about 100 mg, up to about 120 mg, up to about 150 mg, up to about 200 mg, up to about 250 mg, up to about 300 mg, up to about 350 mg, up to about 400 mg, up to about 450 mg, up to about 500 mg, up to about 600 mg, up to about 700 mg, up to about 800 mg, up to about 900 mg, up to about 1,000 mg, up to about 1,200 mg, or up to about 1,500 mg.

In one embodiment, depending on the disease to be treated and the subject's condition, the compound may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound may be formulated, alone or together with one or more active agent(s), in suitable dosage unit with pharmaceutically acceptable excipients, carriers, adjuvants and vehicles, appropriate for each route of administration. In one embodiment, the compound is administered orally. In another embodiment, the compound is administered parenterally. In yet another embodiment, the compound is administered intravenously.

In one embodiment, the compound can be delivered as a single dose such as, e.g., a single bolus injection, or oral tablets or pills; or over time such as, e.g., continuous infusion over time or divided bolus doses over time. In one embodiment, the compound can be administered repetitively if necessary, for example, until the patient experiences stable disease. Stable disease or lack thereof is determined by methods known in the art such as evaluation of patient's symptoms and physical examination.

In one embodiment, the compound can be administered once daily (QD), or divided into multiple daily doses such as twice daily (BID), three times daily (TID), and four times daily (QID). In one embodiment, the administration can be continuous (i.e., daily for consecutive days or every day), intermittent, e.g., in cycles (i.e., including days, weeks, or months of rest when no drug is administered). In one embodiment, the compound is administered daily, for example, once or more than once each day for a period of time. In one embodiment, the compound is administered daily for an uninterrupted period of at least 7 days, in some embodiments, up to 52 weeks. In one embodiment, the compound is administered intermittently, i.e., stopping and starting at either regular or irregular intervals. In one embodiment, the compound is administered for one to six days per week. In one embodiment, the compound is administered on alternate days. In one embodiment, the compound is administered in cycles (e.g., administered daily or continuously for a certain period interrupted with a rest period).

In one embodiment, the frequency of administration ranges from about daily to about monthly. In certain embodiments, the compound is administered once a day, twice a day, three times a day, four times a day, once every other day, twice a week, once every week, once every two weeks, once every three weeks, or once every four weeks. In one embodiment, the compound is administered once a day. In another embodiment, the compound is administered twice a day. In yet another embodiment, the compound is administered three times a day. In still another embodiment, the compound is administered four times a day.

In one embodiment, the compound is administered once per day from one day to six months, from one week to three months, from one week to four weeks, from one week to three weeks, or from one week to two weeks. In certain embodiments, the compound is administered once per day for one week, two weeks, three weeks, or four weeks. In one embodiment, the compound is administered once per day for one week. In another embodiment, the compound is administered once per day for two weeks. In yet another embodiment, the compound is administered once per day for three weeks. In still another embodiment, the compound is administered once per day for four weeks.

In one embodiment, the compound is administered once per day for about 1 week, about 2 weeks, about 3 weeks, about 4 weeks, about 6 weeks, about 9 weeks, about 12 weeks, about 15 weeks, about 18 weeks, about 21 weeks, or about 26 weeks. In certain embodiments, the compound is administered intermittently. In certain embodiments, the compound is administered intermittently in the amount of between about 50 mg/m$^2$/day and about 2,000 mg/m$^2$/day. In certain embodiments, the compound is administered continuously. In certain embodiments, the compound is administered continuously in the amount of between about 50 mg/m$^2$/day and about 1,000 mg/m$^2$/day.

In certain embodiments, the compound is administered to a patient in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In certain embodiments, the compound is administered continuously for between about 1 and about 52 weeks. In certain embodiments, the compound is administered continuously for about 1, 2, 3, 4, 5, 6, 7, 8, 9, 10, 11, or 12 months. In certain embodiments, the compound is administered continuously for about 14, about 28, about 42, about 84, or about 112 days.

In certain embodiments, the compound is administered within 2 days of the patient's exposure to the virus. In these embodiments, the compound is administered twice daily for at least 5 consecutive days. In particular aspects of these embodiments, the compound is orally administered.

In other embodiments, the compound is administered within 2 days of the patient's exposure to the virus. In these embodiments, the compound is administered once daily for at least 10 consecutive days. In particular aspects of these embodiments, the compound is orally administered.

It is understood that the duration of the treatment may vary with the age, weight, and condition of the subject being treated, and may be determined empirically using known testing protocols or according to the professional judgment of the person providing or supervising the treatment. The skilled clinician will be able to readily determine, without undue experimentation, an effective drug dose and treatment duration, for treating an individual subject having a particular type of respiratory viral infection.

VI. EXAMPLES

Certain embodiments are illustrated by the following non-limiting examples.

1 Study Design: Influenza Virus Infected Mice and Effects of Compound Treatment

Groups of 10 mice were used. Each mouse was given a unique experimental number and analyzed individually. Bronchoalveolar lavage (BAL), nasal tissue/washes and serum were collected and stored with their corresponding experimental number. One lobe of lung was homogenized for Plaque assay to determine pathogen titer. A separate lung lobe per mouse was fixed in formalin for histological analysis. The remainder of the lung was digested to a single cell suspension for analysis of cell subtypes by flow cytometry. This method generated 5 individual data points per experiment, which can be used to quantify the reproducibility of the data.

Correlation of protection and pathology were determined as follows.

a. Pathogen clearance was monitored by virus plaque assay. The effect of infection or treatment on viral dissemination was examined in homogenates of lung tissue.

b. Pathology was monitored by weight loss and illness daily, using a standard scoring system based on degree of cachexia, mobility and/or weight.

Immunity was monitored by the quantification of, (1) T, B and NK cells determined by flow cytometry; and (2) the frequency of T cells (both CD4+ and CD8+) expressing intracellular cytokines (e.g., IL2, TNFα, and IFNγ) or surface markers of activation (e.g., CD69) determined by flow cytometry. When the results appear positive, cytokine concentrations in lavage fluid, serum and nasal wash are analyzed by ELISA.

Compound 1, having the following structure, was administered in the mice as described in the examples herein.

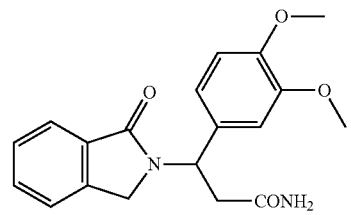 [SMILES: COc1ccc(C(CC(N)=O)N2Cc3ccccc3C2=O)cc1OC]

Ten mice per group were infected intranasally on day 0 with 50 HA Units of the influenza X31 strain (H3N2) in a 50 µL volume. On days 0, 1, 2, 3, 4, 5 and 6, Compound 1 was administered intraperitoneally. Five mice per group were culled on days 3 and 7 post the influenza infection.

The vehicle (0.5% CMC/0.25% Tween 80 in water) was prepared in distilled water and dissolved overnight by stirring on a magnetic stirrer (e.g., 0.5 g CMC and 0.25 mL Tween 80 to 99.75 mL water to make a total of 100 mL 0.5% CMC/0.25% Tween 80 vehicle). Compound 1 was dissolved in the vehicle. 100 µg of this solution was injected into each mouse, for a daily dose of 0.1 mg per day.

The animals were divided into three groups. Group 1 received no treatment. Group 2 received vehicle control (diluent without Compound 1). Group 3 received Compound 1 in vehicle.

| Group | Drug | Dosage | Route |
|---|---|---|---|
| 1 | No treatment | N/A | N/A |
| 2 | Vehicle control (diluent) | 100 µL/mice | Intraperitoneal injection |
| 3 | Compound 1 | 100 µg/mice | Intraperitoneal injection |

Mouse weights before and after the influenza infection were recorded. On day 3 and day 7, mice were culled and analyzed for cellular infiltrate into the airways, the lung, and the lymph nodes, including, intracellular cytokine production, T cell subtypes, macrophages, B cells, NK cells, and neutrophils.

Sera was stored for analysis of influenza-specific antibody. One lobe of the lung was snap frozen for viral titers analysis (plaque assay) and one placed in formalin for histology analysis.

In one embodiment, without being limited by a particular theory, the potential a cytokine blockade compound, such as Compound 1, to treat seasonal influenza infection is evaluated.

2. Weight Loss

Weight loss can be a direct indication of the severity of infection in the lung and can correlate with the extent of cellular infiltrate, particularly T cells. In influenza infected mice, the percent original weight was calculated from the day 0 weight prior to viral infection (FIG. 1). Weight loss occurred after the peak viral load at day 4 of infection. By day 5 and 6, viral titers were low, but T cell infiltrate was maximal. Thus, the weight loss appeared to occur via occlusion of the airspaces and damages caused by cytotoxic T cell and natural killer cell lysis of infected respiratory epithelium and pyrogenic cytokines such as IL-6 and TNF.

The administration of Compound 1 (diamonds in FIG. 1) to influenza infected mice resulted in significantly reduced weight loss compared to vehicle control (squares in FIG. 1) and untreated mice (triangles in FIG. 1). Compound 1 treated mice appeared visibly in better health. The controls and untreated mice appeared hunched and cachexic on day 5.

3. Total Viable Cell Counts in the Airway (BAL) and Lung Tissue

Total viable cell counts were enumerated by trypan blue exclusion and light microscopy. About $1 \times 10^5$ cells were recovered from the airway of uninfected animals comprising almost entirely of alveolar macrophages ($CD11c^+$, $CD11b^+$, $F4/80^+$). The lung of uninfected animals liberated about $5 \times 10^5$ cells upon digest.

Treatment with Compound 1 significantly reduced the cellular infiltrate into the airway (BAL) on day 3 of infection (FIG. 2), which likely accounted for the reduction in weight loss as compared to untreated animals. This effect was not observed at the later time point of day 7 or in the lung parenchyma at either day 3 or day 7 (FIG. 2). The cell counts in the airway (BAL fluid) of Compound 1 treated mice on day 3 was less than half of that found in the infected mice not treated with Compound 1.

4. Macrophages in the Airspaces

In uninfected mice, the airspaces contain predominantly macrophages and their reduction is a reliable indication of infiltration of other cell types into the airspaces.

Five mice per group were harvested at day 3 of infection and macrophages were enumerated by flow cytometry. Results were shown as mean+/−SEM (FIG. 3). In Compound 1 treated mice, at day 3 of infection, a higher proportion of the cells recovered from the airspaces were macrophages.

The reduction in total cells at day 3 in the airspaces of Compound 1 treated mice appeared to be primarily associated with neutrophils (CD11c+ and Ly6g+) (FIG. 4). Neutrophils are usually prominent in influenza-infected mice due to viral replication in the epithelium that in turn releases the chemotactic factors KC (IL-8) and MIP2.

At 7 day, no significant differences were observed on the number of both macrophage and neutrophils in all sites between the animal groups.

5. Effect on T Cell Recruitment

In mice infected with the influenza virus, treatment with Compound 1 reduced T cell recruitment. T cell recruitment was assessed by analyzing the surface markers CD4 and CD8 by flow cytometry. Early CD4+ T cell recruitment to the airways (BAL) was reduced in Compound 1 treated mice with a corresponding accumulation of them in the lung parenchyma. This implies that Compound 1 affected chemotactic factors produced by cells in the airspaces, presumably those elicited from the epithelium. This is similar to the results of previous studies showing that immune mediated pathology occurs in the airspaces and enhanced cells are not pathogenic in the lung tissue.

By day 7, no differences in T cell recruitment were observed between the animal groups. The reduced cellularity at the early time points did not appear to affect the development of acquired immunity. Thus, it is expected that virus elimination will be about equal in all groups and immunological memory will be intact.

FIG. 5 shows that treatment with Compound 1 affected early T cell recruitment. Mice that had received daily treatment with Compound 1 or vehicle, or untreated mice were culled at day 3 after infection. Bronchoalveolar lavage (BAL) was performed and the lung tissue was processed to harvest cells. Airway (A, B) and lung (C, D) cells were stained for CD4. The left panels represent the percentage of CD4+ cells and the right panels represent the actual cell number. The data is represented as the mean±SE from 5 individual mice per group.

FIG. 6 shows that treatment with Compound 1 did not affect later T cell populations. Mice that had received daily treatment with Compound 1 or vehicle, or untreated mice were culled at day 7 after infection. Bronchoalveolar lavage (BAL) was performed and the lung tissue was processed to harvest cells. Airway (A, B) and lung (C, D) cells were staining for CD4. The left panels represent the percentage of CD4+ cells and the right panels represent the actual cell number. The data is represented as the mean±SE from 5 individual mice per group.

No difference in CD8+ T cells was observed at any time point analyzed.

6. Effect on Lung T Cell Cytokine Production

A partial reduction of CD4+ T cells producing IFNγ was observed at day 7 in the lung tissue but not in the airways (BAL) of Compound 1 treated mice as compared to untreated mice and vehicle controls (FIG. 7). This effect was observed in the CD4+ population. CD8+ T cells cytokine expression remained unchanged.

T cell IFNγ expression was analyzed by flow cytometry. Lung cells were first stained for CD4 and CD8 and then permeabilized using saponin before adding the antibodies to the relevant cytokine. Percent positive CD4 T cells (Column A) or CD8 T cells (Column B) were determined by flow cytometry. The proportions expressing the cytokines shown were then calculated (FIG. 7).

T cell IFNγ expression was analyzed by flow cytometry. Airway cells were first stained for CD4 and CD8 and then permeabilized using saponin before adding the antibodies to the relevant cytokine. Percent positive CD4 T cells (Column A) or CD8 T cells (Column B) were determined by flow cytometry. The proportions expressing the cytokines shown were then calculated (FIG. 8).

7. Effect on Peak Viral Load

In mice infected with the influenza virus, treatment with Compound 1 reduced peak viral load. To characterize the effect of treatment on viral clearance, a plaque assay on lung homogenates was performed. Mice were harvested on day 3 (A) and day 7 (B). A lobe of lung was homogenized for plaque assay to establish the viral titer. Data represented the mean values±SEM, n=5 per time point (FIG. 9).

In general, the viral titers of all groups decreased from day 3 to day 7 (note the scale change between A and B in FIG. 9). At the early stages of viral replication, Compound 1 treatment blunted the recovered viral titer. At day 7, the Compound 1 treated group displayed similar viral titers to the two control groups.

8. Evaluation of PDE-4 Inhibitors for Treatment of an Influenza A/CA/04/2009 (Pandemic H1N1) Virus Infection in BALB/c Mice Compounds 1, 2, 3 and 4, respectively having structures shown below, are evaluated for their efficacy in treating Influenza A/CA/04/2009 (H1N1) virus infection in BALB/c mice:

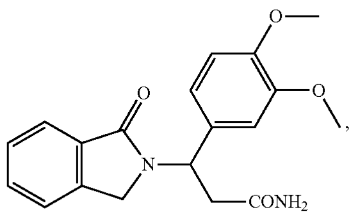

,

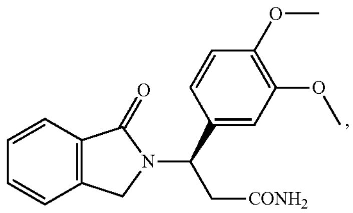

,

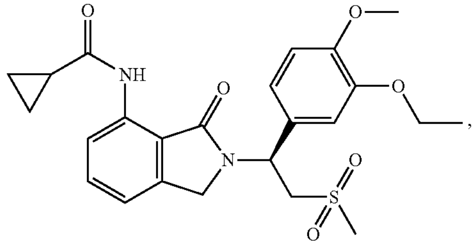

,

-continued

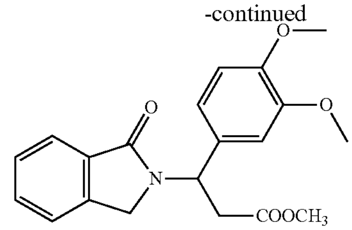

.

Influenza virus is intranasally administered to BALB/c mice weighing 18 to 20 g. Compound 1, 2, 3 or 4, each in 0.5% CMC/0.25% Tween 80, is administered to the infected mice with or without ampicillin according to the experimental design as shown in the below tables. As controls, placebo, ampicillin and ribavirin are each administered to the infected mice without the test compounds. In addition, ininfected normal mice, without administration of any of the compounds, are included as a positive control for weight gain observation. Ten (10) mice for each treatment group, 20 mice for each placebo group, and 5 for each normal control group are included for the testing.

The treatments start at 4 hours post-infection. Compounds 1-4 and ampicillin are administered i.p. once a day for 7 days. Ribavirin is administered p.o. twice a day for 5 days. Parameters such as percent survivors, mean day of death determination, body weight change measured every other day during the infection, and lung parameters (e.g., score, weight and virus titers) are recorded and evaluated.

Study Design I

| No./ Cage | Group No. | Infected | Cpds | Dosage | Treatment Schedule | Observation/ Testing |
|---|---|---|---|---|---|---|
| 20 | 1 | Yes | Placebo | 0.5% CMC/0.25% Tween 80 | i.p., qd × 7 days, beg. day 0, 4 hr post-infection | Observed for weight loss and death |
| 10 | 2 | Yes | Cpd 1 | 50 mg/kg/day | i.p., qd × 7 days, beg. day 0, 4 hr post-infection | through day 21 |
| 10 | 3 | Yes | Cpd 1 + ampicillin | 50 mg/kg/day each | i.p., qd × 7 days, beg. day 0, 4 hr post-infection | |
| 10 | 4 | Yes | Cpd 2 | 50 mg/kg/day | i.p., qd × 7 days, beg. day 0, 4 hr post-infection | |
| 10 | 5 | Yes | Cpd 2 + ampicillin | 50 mg/kg/day each | i.p., qd × 7 days, beg. day 0, 4 hr post-infection | |
| 10 | 6 | Yes | Cpd 3 | 50 mg/kg/day | i.p., qd × 7 days, beg. day 0, 4 hr post-infection | |
| 10 | 7 | Yes | Cpd 3 + ampicillin | 50 mg/kg/day each | i.p., qd × 7 days, beg. day 0, 4 hr post-infection | |
| 10 | 8 | Yes | Cpd 2 | 50 mg/kg/day | i.p., qd × 7 days, beg. day 0, 4 hr post-infection | |
| 10 | 9 | Yes | Cpd 2 + ampicillin | 50 mg/kg/day each | i.p., qd × 7 days, beg. day 0, 4 hr post-infection | |
| 10 | 10 | Yes | ampicillin | 50 mg/kg/day | i.p., qd × 7 days, beg. day 0, 4 hr post-infection | |
| 10 | 11 | Yes | Ribavirin | 75 mg/kg/day | p.o, bid × 5, 12 hrs apart, beg. day 0, 4 hr post-infection | |
| 5 | 12 | No | Normal Mice Obsreved for Weight Gain | | | |

Study Design II

| No./Cage | Group No. | Infected | Cpds | Dosage | Treatment Schedule | Observation/Testing |
|---|---|---|---|---|---|---|
| 10 | 1a | Yes | Placebo | 0.5% CMC/0.25% Tween 80 | i.p., qd × 7 days, beg. day 0, 4 hr post-infection | 5 mice sacrificed on days 3 and 6 for lung parameters: score, weight and virus titers |
| 10 | 2a | Yes | Cpd 1 | 50 mg/kg/day | i.p., qd × 7 days, beg. day 0, 4 hr post-infection | |
| 10 | 3a | Yes | Cpd 1 + ampicillin | 50 mg/kg/day each | i.p., qd × 7 days, beg. day 0, 4 hr post-infection | |
| 10 | 4a | Yes | Cpd 2 | 50 mg/kg/day | i.p., qd × 7 days, beg. day 0, 4 hr post-infection | |
| 10 | 5a | Yes | Cpd 2 + ampicillin | 50 mg/kg/day each | i.p., qd × 7 days, beg. day 0, 4 hr post-infection | |
| 10 | 6a | Yes | Cpd 3 | 50 mg/kg/day | i.p., qd × 7 days, beg. day 0, 4 hr post-infection | |
| 10 | 7a | Yes | Cpd 3 + ampicillin | 50 mg/kg/day each | i.p., qd × 7 days, beg. day 0, 4 hr post-infection | |
| 10 | 8a | Yes | Cpd 2 | 50 mg/kg/day | i.p., qd × 7 days, beg. day 0, 4 hr post-infection | |
| 10 | 9a | Yes | Cpd 2 + ampicillin | 50 mg/kg/day each | i.p., qd × 7 days, beg. day 0, 4 hr post-infection | |
| 10 | 10a | Yes | ampicillin | 50 mg/kg/day | i.p., qd × 7 days, beg. day 0, 4 hr post-infection | |
| 10 | 11a | Yes | Ribavirin | 75 mg/kg/day | p.o. bid × 5, 12 hrs apart, beg. day 0, 4 hr post-infection | |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein by reference in their entireties. Citation or identification of any reference in this application is not an admission that such reference is available as prior art to this application. The full scope of the disclosure is better understood with reference to the appended claims.

What is claimed is:

1. A method of treating, ameliorating, or delaying the onset of one or more symptoms associated with or resulting from a respiratory viral infection in a subject, comprising administering to the subject a compound, or a pharmaceutically acceptable salt, solvate, hydrate, or stereoisomer thereof, wherein the compound is

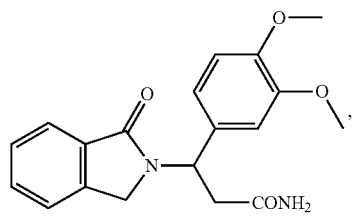

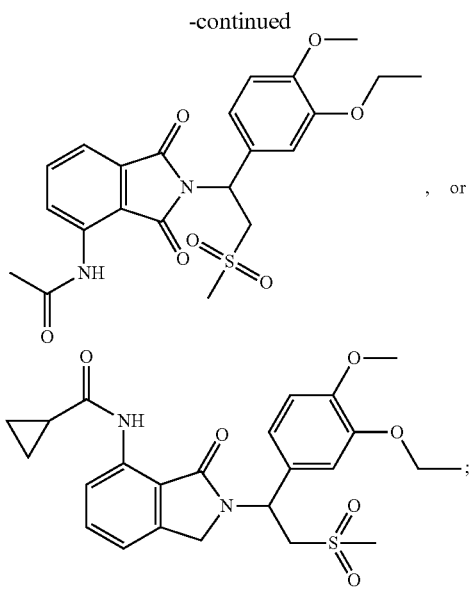

and wherein the respiratory viral infection is influenza infection, rhinovirus infection, coronavirus infection, or paramyxovirus infection.

2. The method of claim 1, further comprising administering at least one second active agent.

3. The method of claim 2, wherein the second active agent is an antiviral agent or an antibiotic agent.

4. The method of claim 1, wherein the respiratory viral infection is influenza infection.

5. The method of claim 4, wherein the influenza is type A influenza.

6. The method of claim 5, wherein the type A influenza is of a subtype, selected from the group consisting of: H1N1, H2N2, H3N2, H5N1, H7N7, H1N2, H9N2, H7N2, H7N3, and H10N7 subtypes.

7. The method of claim 4, wherein the influenza is type B influenza.

8. The method of claim 4, wherein the influenza is type C influenza.

9. The method of claim 1, wherein the respiratory viral infection is rhinovirus infection.

10. The method of claim 1, wherein the respiratory viral infection is coronavirus infection.

11. The method of claim 1, wherein the respiratory viral infection is paramyxovirus infection.

12. The method of claim 1, wherein the compound, or a pharmaceutically acceptable salt, solvate, hydrate, or stereoisomer thereof, is administered orally, parenterally, intranasally, or topically.

13. The method of claim 1, wherein the subject is a human.

14. The method of claim 1, wherein the stereoisomer of the compound is enantiomerically pure.

15. The method of claim 1, wherein the compound is

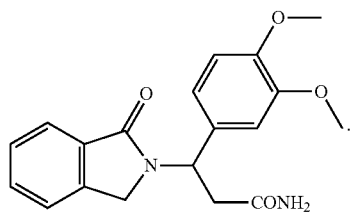 [SMILES: COc1ccc(C(CC(N)=O)N2Cc3ccccc3C2=O)cc1OC]

16. The method of claim 15, wherein the compound is enantiomerically pure.

17. The method of claim 1, wherein the compound is

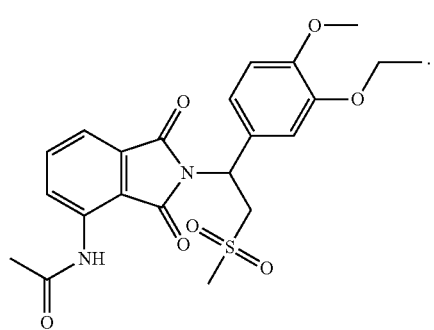 [SMILES: CCOc1cc(C(CS(C)(=O)=O)N2C(=O)c3cccc(NC(C)=O)c3C2=O)ccc1OC]

18. The method of claim 17, wherein the compound is enantiomerically pure.

19. The method of claim 1, wherein the compound is

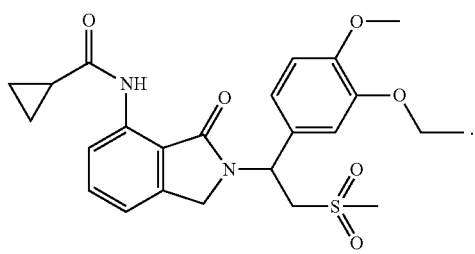 [SMILES: CCOc1cc(C(CS(C)(=O)=O)N2Cc3cccc(NC(=O)C4CC4)c3C2=O)ccc1OC]

20. The method of claim 19, wherein the compound is enantiomerically pure.

21. The method of claim 1, wherein the symptom associated with or resulting from the respiratory viral infection is fever, chills, sweating, headache, fatigue, tiredness, exhaustion, cough, runny nose, stuffy nose, sneezing, sore throat, body aches, muscle aches, joint pains, sinus pains, ear aches, chest pains, chest discomfort, sinus congestion, diarrhea, vomiting, abdominal pains, dehydration, or shortness of breath.

22. The method of claim 1, wherein the treating, ameliorating, or delaying the onset of one or more symptoms associated with or resulting from a respiratory viral infection results in a reduction in weight loss as compared to that in an untreated subject.

23. The method of claim 1, wherein the treating, ameliorating, or delaying the onset of one or more symptoms associated with or resulting from a respiratory viral infection results in reduced lung damage as compared to that in an untreated subject.

24. The method of claim 1, wherein the treating, ameliorating, or delaying the onset of one or more symptoms associated with or resulting from a respiratory viral infection results in a decreased viral load as compared to that in an untreated subject.

* * * * *